US006831053B1

(12) United States Patent
Ghosh et al.

(10) Patent No.: US 6,831,053 B1
(45) Date of Patent: Dec. 14, 2004

(54) BLEACHING COMPOSITIONS COMPRISING MULTIPLY-SUBSTITUTED PROTEASE VARIANTS

(75) Inventors: Chanchal Kumar Ghosh, West Chester, OH (US); André Cesar Baeck, Bonheiden (BE); Ryohei Ohtani, Naka-machi (JP); Alfred Busch, Londerzeel (BE); Michael Stanford Showell, Cincinnati, OH (US); Ayrookaran J. Poulose, Belmont, CA (US); Volker Schellenberger, Palo Alto, CA (US); James T. Kellis, Jr., Portola Valley, CA (US); Christian Paech, Daly City, CA (US); Joanne Nadherny, San Francisco, CA (US); Donald P. Naki, San Francisco, CA (US); Katherine D. Collier, Redwood City, CA (US); Robert M. Caldwell, San Carlos, CA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/529,904
(22) PCT Filed: Oct. 23, 1998
(86) PCT No.: PCT/US98/22482
§ 371 (c)(1), (2), (4) Date: Apr. 20, 2000
(87) PCT Pub. No.: WO99/20726
PCT Pub. Date: Apr. 29, 1999

(51) Int. Cl.[7] .................................................. C11D 3/00
(52) U.S. Cl. ........................ 510/392; 392/305; 392/300; 435/221; 435/219; 435/222
(58) Field of Search .................................. 510/306, 311, 510/312, 313, 392; 435/219, 221, 222

(56) References Cited
U.S. PATENT DOCUMENTS
4,914,031 A    4/1990 Zukowski et al. ........... 435/222
(List continued on next page.)

FOREIGN PATENT DOCUMENTS
EP    0 328 229    8/1989    ............ C12N/9/50
(List continued on next page.)

*Primary Examiner*—Yogendra N. Gupta
*Assistant Examiner*—Eisa Elhilo
(74) *Attorney, Agent, or Firm*—Julie A. McConihay; Frank Taffy; C. Brant Cook

(57) ABSTRACT

The present invention relates to bleaching compositions comprising a protease variant. One bleaching composition comprises a protease variant including a substitution of an amino acid residue with another naturally occurring amino acid residue at an amino acid residue position corresponding to position 103 of *Bacillus amyloliquefaciens* subtilisin in combination with a substitution of an amino acid residue with another naturally occurring amino acid residue at one or more amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274, and 275 of *Bacillus amyloliquefaciens* subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265, or 274 of *Bacillus amyloliquefaciens* subtilisin, a bleaching agent; and one or more cleaning adjunct materials. Another bleaching composition comprises a protease variant including a substitution of an amino acid residue with another naturally occurring amino acid residue at one or more amino acid residue positions corresponding to positions 62, 212, 230, 232, 252 and 257 of *Bacillus amyloliquefaciens* subtilisin; a bleaching agent; and one or more cleaning adjunct materials. Methods for using the bleaching compositions are also provided.

49 Claims, 6 Drawing Sheets

U.S. PATENT DOCUMENTS

| | | | |
|---|---|---|---|
| 5,155,033 A | 10/1992 | Estell et al. | 435/221 |
| 5,182,204 A | 1/1993 | Estell et al. | 435/222 |
| 5,185,258 A | 2/1993 | Caldwell et al. | 435/220 |
| 5,204,015 A | 4/1993 | Caldwell et al. | 252/174.12 |
| RE34,606 E | 5/1994 | Estell et al. | 435/222 |
| 5,677,272 A | 10/1997 | Ghosh et al. | 510/306 |
| 5,679,630 A * | 10/1997 | Baeck et al. | 510/305 |
| 6,066,611 A * | 5/2000 | Ghosh et al. | 510/306 |
| 6,197,567 B1 * | 3/2001 | Aaslyng et al. | 435/221 |

FOREIGN PATENT DOCUMENTS

| | | | |
|---|---|---|---|
| EP | 0 405 901 | 1/1991 | C11D/3/386 |
| WO | WO 89/06279 | 7/1989 | C12N/9/50 |
| WO | WO 92/21760 | 12/1992 | C12N/15/57 |
| WO | WO 9/10591 | 4/1995 | C11D/3/386 |
| WO | WO 95/10591 | 4/1995 | C11D/3/386 |
| WO | WO 96/28566 | 9/1995 | |
| WO | WO 95/30010 | 11/1995 | C12N/15/57 |
| WO | WO 98/55634 | 12/1998 | C12N/15/57 |

* cited by examiner

-1        1                                                                       10
                                                                                                                  MAT   His Val Ala His Ala Tyr Ala Gln Ser Val Pro Tyr Gly Val Ser Gln Ile Lys Ala Pro Ala Leu His Ser Gln
                                                                                                          399          CAC GTA GCA CAT GCG TAC GCG CAG TCC GTG CCT TAC GGC GTA TCA CAA ATT AAA GCC CCT GCT CTG CAC TCT CAA 20                                                                    30                                                                           40
            Gly Tyr Thr Gly Ser Asn Val Lys Val Ala Val Ile Asp Ser Gly Ile Asp Ser Ser His Pro Asn Leu Lys Val
        474 GGC TAC ACT GGA TCA AAT GTT AAA GTA GCG GTT ATC GAC AGC GGT ATC GAT TCT TCT CAT CCT GAT TTA AAG GTA

Pro Asn
            Ala Gly Gly Ala Ser Met Val Pro Ser Glu Thr Asn Pro Phe Gln Asp Asn Asn Ser His Gly Thr His Val Ala
        549 GCA GGT GGA GCC AGC ATG GTT CCT TCT GAA ACA AAT CCT TTC CAA GAC AAC AAC TCT CAC GGA ACT CAC GTT GCC 50                                                 60 Asp
                                                                                                            Ser Ala       90
            Gly Thr Val Ala Ala Leu Asn Asn Ser Ile Gly Val Leu Gly Val Ala Pro Ser Ala Ser Leu Tyr Ala Val Lys
        624 GGC ACA GTT GCG GCT CTT AAT AAT TCA ATC GGT GTT TTA GGC GTT GCG CCA AGC GCA TCA CTT TAC GCT GTA AAA

70
            Val Leu Gly Ala Asp Gly Ser Gly Gln Tyr Ser Trp Ile Ile Asn Gly Ile Glu Trp Ala Ile Ala Asn Asn Met
        699 GTT CTC GGT GCT GAC GGT TCC CAA TAC AGC TGG ATC ATT AAC GGA ATC GAG TGG GCG ATC GCA AAC AAT ATG

Asp Ala 100                                                          110
                                                                                                                                    140
            Asp Val Ile Asn Met Ser Leu Gly Gly Pro Ser Gly Ser Ala Ala Leu Lys Ala Ala Val Asp Lys Ala Val Ala
        774 GAC GTT ATT AAC ATG AGC CTC GGC GGA CCT TCT GGT TCT GCT GCT TTA AAA GCG GCA GTT GAT AAA GCC GTT GCA

120                                                Ser Thr 160
            Ser Gly Val Val Val Ala Val Ala Ala Gly Asn Glu Gly Ser Ser Gly Ser Ser Ser Thr Val Gly Tyr Pro Gly
        849 TCC GGT GTC GTA GTC GCG GCA GCC GGT AAC GAA GGC TCC AGC GGA AGC TCA AGC ACA GTG GGC TAC CCT GGT 150                                                130

FIG-1B

```
     170
     Lys Tyr Pro Ser Val Ile Ala Val Gly Ala Val Asp Ser Ser Asn Gln Arg Ala Ser Phe Ser Ser Val Gly Pro
 924 AAA TAC CCT TCT GTC ATT GCA GTT GGC GCT GTT GAC AGC AGC AAC CAA AGA GCA TCT TTC TCA AGC GTA GGA CCT
                                    180                                     190
     Glu Leu Asp Val Met Ala Pro Gly Val Ser Ile Gln Ser Thr Leu Pro Gly Asn Lys Tyr Gly Ala Tyr Asn Gly
 999 GAG CTT GAT GTC ATG GCA CCT GGC GTA TCT ATC CAA AGC ACG CTT CCT GGA AAC AAA TAC GGG GCG TAC AAC GGT
                    200                                     210
     Thr Ser Met Ala Ser Pro His Val Ala Gly Ala Ala Leu Ile Leu Ser Lys His Pro Asn Trp Thr Asn Thr
1074 ACG TCA ATG GCA TCT CCG CAC GTT GCC GGA GCG GCT TTG ATT CTT TCT AAG CAC CCG AAC TGG ACA AAC ACT
         220                                     230                                     240
     Gln Val Arg Ser Ser Leu Glu Asn Thr Thr Thr Lys Leu Gly Asp Ser Phe Tyr Tyr Gly Lys Gly Leu Ile Asn
1149 CAA GTC CGC AGC AGT TTA GAA AAC ACC ACT ACA AAA CTT GGT GAT TCT TTG TAC TAT GGA AAA GGG CTG ATC AAC
                                250    Gln                           260
     Val Gln Ala Ala Ala Gln Ala Ala Gln  OC
1224 GTA CAA GCG GCA GCT CAG TAA    AACATAAAAACGGGCCTTGGCCCCGCGGTTTTTATTATTTTCTCCTCCGCATGTTCAATCCGCTCC
         270       275                    TERM
1316 ATAATCGACGGATGGCTCCCTCTGAAAATTTTAACGAGAAACGGGGTTGACCCGGCTCAGTCCGCTAACGGCCAACTCCTGAAACGTCTCAATCGCCG

1416 CTTCCCGGGTTTCCGGGTCAGCTCAATGCCATAACGGGTCGGCGGGGGTTTCCTGATACCGGGAGACGGCATTGTAATCGGATC
```

FIG.-1C

CONSERVED RESIDUES IN SUBTILISINS FROM
BACILLUS AMYLOLIQUEFACIENS

Comparison of subtilisin sequences from:

B.amyloliquefaciens
B.subtilis
B.licheniformis
B.lentus

```
                10         20         30
01  AQSVPYGVSQIKAPALHSQGYTGSNVKVAVIDSGIDSSHP
    AQSVPYGVSQIKAPALHSQGYTGSNVKVAVIDSGIDSSHP
    AQTVPYGIPLIKADKVQAQGFKGANVKVAVLDTGIQASHP
    AQSVPWGISRVQAPAAHNRGLTGSGVKVAVLDTGIST*HP 50         60         70
41  DLKVAGGASMVPSETNPFQDNNSHGTHVAGTVAALNNSIG
    DLNVRGGASFVPSETNPYQDGSSHGTHVAGTIAALNNSIG
    DLNVVGGASFVAGEAYNTDGNGHGTHVAGTVAALDNTTG
    DLNIRGGASFVPGE*PSTQDGNGHGTHVAGTIAALNNSIG 90        100        110
81  VLGVAPSASLYAVKVLGADGSGQYSWIINGIEWAIANNMD
    VLGVSPSASLYAVKVLDSTGSGQYSWIINGIEWAIANNMD
    VLGVAPSVSLYAVKVLNSSGSGSYSGIVSGIEWATTNGMD
    VLGVAPSAELYAVKVLGASGSGSVSSIAQGLEWAGNNGMH 130        140        150
121 VINMSLGGPSGSAALKAAVDKAVASGVVVVAAAGNEGTSG
    VINMSLGGPSGSTAMKQAVDKAVSSGIVVVAAAGNEGSSG
    VINMSLGGASGSTAMKQAVDNAYARGVVVVAAAGNSGAGS
    VANLSLGSPSPSATLEQAVNSATSRGVLVVAASGNSGAGS
```

BLEACHING COMPOSITIONS COMPRISING MULTIPLY-SUBSTITUTED PROTEASE VARIANTS

FIELD OF THE INVENTION

The present invention relates to bleaching compositions, especially laundry detergents, which comprise one or more protease enzymes which are multiply-substituted protease variants and a bleaching system with one or more bleaching agents, especially bleach activators, and methods of using such bleaching compositions.

BACKGROUND OF THE INVENTION

Various types of enzymes have long been conventionally used in laundry detergents to assist in the removal of certain stains from fabrics. These stains are typically associated with lipid and protein soils. The enzymes, however, have proven less effective against other types of soils and stains.

U.S. Pat. No. 5,677,272 to Ghosh et al., issued Oct. 10, 1997, discloses bleaching compositions comprising: 1) a protease variant including substitutions of amino acid residues with other amino acid residues at positions corresponding to positions 76 in combination with one or more of the following positions 99, 101, 103, 104, 107, 123, 27, 105, 109, 126, 128, 135, 156, 166, 195, 197, 204, 206, 210, 216, 217, 218, 222, 260, 265 and/or 274 of *Bacillus amyloliquefaciens* subtilisin; 2) a bleaching agent; and 3) one or more bleaching composition materials compatible with the protease variant and bleaching agent.

However, a need for more effective stain removal and/or dingy cleanup over the conventional bleaching compositions still exists.

By the present invention, it has been found that the combination of novel protease enzymes which are multiply-substituted protease variants and bleaching agents, especially bleach activators, provide enhanced and improved stain removal and/or dingy cleanup benefits over conventional bleaching compositions.

Accordingly, it is an object of the present invention to provide bleaching compositions, especially laundry detergent compositions, having improved stain and/or soil removal and/or dingy cleanup benefits and/or fabric cleaning benefits and/or bleaching properties.

These and other objects of the present invention will be apparent from the detailed description hereinafter.

SUMMARY OF THE INVENTION

The present invention meets the aforementioned needs in that it has been surprisingly discovered that the multiply-substituted protease variants of the present invention, when used in bleaching compositions provide improved and enhanced cleaning benefits, including, but not limited to, stain and/or soil removal and/or reduction and/or whiteness maintenance and/or dingy cleanup and/or spot and/or film removal and/or reduction, over conventional protease-containing bleaching compositions.

The multiply-substituted protease variants of the present invention are suitable for use in high and low density granular, heavy duty and light duty liquids, tablets, powders, gels, foams, sprays, paste, as well as synthetic detergent bar compositions, and other bleaching compositions.

In one aspect of the present invention a bleaching composition comprising:

(a) a protease variant, preferably an effective amount of a protease variant, more preferably from about 0.0001% to about 10% by weight of the bleaching composition of a protease variant, wherein said protease variant includes a substitution of an amino acid residue with another naturally occurring amino acid residue at an amino acid residue position corresponding to position 103 of *Bacillus amyloliquefaciens* subtilisin in combination with a substitution of an amino acid residue with another naturally occurring amino acid residue at one or more amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of *Bacillus amyloliquefaciens* subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 of *Bacillus amyloliquefaciens* subtilisin;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) one or more cleaning adjunct materials.

In yet another aspect of the present invention, a fabric bleaching composition comprising:

(a) an effective amount, preferably from about 0.0001% to about 10% by weight of the fabric bleaching composition, of the protease variant described above;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition;

(c) at least about 5% by weight of the fabric bleaching composition of a surfactant; and (d) at least about 5% by weight of the fabric bleaching composition of a builder, is provided.

In still another aspect of the present invention, a method for cleaning a fabric in need of cleaning comprising contacting the fabric with the fabric bleaching composition of the present invention is provided.

In still yet another aspect of the present invention, a dishwashing bleaching composition comprising:

(a) an effective amount, preferably from about 0.0001% to about 10% by weight of the dishwashing composition, of a protease variant described above;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) from about 0.1% to about 10% by weight of a surfactant, is provided.

In still yet another aspect of the present invention, a method for cleaning a dish in need of cleaning comprising contacting the dish with the dishwashing bleaching composition of the present invention is provided.

In still yet another aspect of the present invention, a personal cleansing composition comprising:

(a) an effective amount, preferably from about 0.001% to about 5% by weight of the personal cleansing composition, of a protease variant described above;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) from about 0.1% to about 95% by weight of the personal cleansing composition of a surfactant system; and (d) optionally, from about 0.05% to about 50% by weight of the personal cleansing composition of an enzyme stabilizer, is provided.

In still yet another aspect of the present invention, a method for personal cleansing of a part of the human or lower animal body in need of cleansing comprising contacting the part with the personal cleansing composition of the present invention is provided.

In still yet another aspect of the present invention, a bleaching composition comprising:

(a) a protease variant, preferably an effective amount of a protease variant, more preferably from about 0.0001% to about 10% by weight of the bleaching composition of a protease variant, wherein said protease variant includes a substitution of an amino acid residue with another naturally occurring amino acid residue at one or more amino acid residue positions corresponding to positions 62, 212, 230, 232, 252 and 257 of *Bacillus amyloliquefaciens* subtilisin;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) one or more cleaning adjunct materials, is provided.

In still yet another aspect of the present invention, a fabric bleaching composition comprising:

(a) an effective amount, preferably from about 0.0001% to about 10% by weight of the fabric bleaching composition, of a protease variant wherein said protease variant includes a substitution of an amino acid residue with another naturally occurring amino acid residue at one or more amino acid residue positions corresponding to positions 62, 212, 230, 232, 252 and 257 of *Bacillus amyloliquefaciens* subtilisin;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition;

(c) at least about 5% by weight of the fabric bleaching composition, of a surfactant; and (d) at least about 5% by weight of the fabric bleaching composition, of a builder, is provided.

In still another aspect of the present invention, a method for cleaning a fabric in need of cleaning comprising contacting the fabric with the fabric bleaching composition of the present invention is provided.

In still yet another aspect of the present invention, a dishwashing bleaching composition comprising:

(a) an effective amount, preferably from about 0.0001% to about 10% by weight of the fabric bleaching composition, of a protease variant wherein said protease variant includes a substitution of an amino acid residue with another naturally occurring amino acid residue at one or more amino acid residue positions corresponding to positions 62, 212, 230, 232, 252 and 257 of *Bacillus amyloliquefaciens* subtilisin;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) from about 0.1% to about 10% by weight of the dishwashing composition, of a surfactant, is provided.

In still yet another aspect of the present invention, a method for cleaning a dish in need of cleaning comprising contacting the dish with the dishwashing bleaching composition of the present invention is provided.

In still yet another aspect of the present invention, a personal cleansing composition comprising:

(a) an effective amount, preferably from about 0.001% to about 5% by weight of the personal cleansing composition, of a protease variant wherein said protease variant includes a substitution of an amino acid residue with another naturally occurring amino acid residue at one or more amino acid residue positions corresponding to positions 62, 212, 230, 232, 252 and 257 of *Bacillus amyloliquefaciens* subtilisin;

(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) from about 0.1% to about 95% by weight of the personal cleansing composition, of a surfactant system; and (d) optionally, from about 0.05% to about 50% by weight of the personal cleansing composition, of an enzyme stabilizer, is provided.

In still yet another aspect of the present invention, a method for personal cleansing of a part of the human or lower animal body in need of cleansing comprising contacting the part with the personal cleansing composition of the present invention is provided.

Accordingly, it is an object of the present invention to provide bleaching compositions having a protease variant capable of providing improved and enhanced cleaning of fabrics, dishware, tableware, kitchenware, cookware and other hard surface substrates. It is a further object of the present invention to provide methods for fabric, dishware, tableware, kitchenware, cookware and other hard surface substrate cleansing via the use of the protease variant-containing bleaching compositions of the present invention.

These and other objects, features and advantages will be clear from the following detailed description, examples and appended claims.

All percentages, ratios and proportions herein are on a weight basis unless otherwise indicated. All documents cited herein are hereby incorporated by reference.

BRIEF DESCRIPTION OF THE DRAWINGS

FIGS. 1A–C depict the DNA and amino acid sequence for *Bacillus amyloliquefaciens* subtilisin and a partial restriction map of this gene.

FIG. 2 depicts the conserved amino acid residues among subtilisins from *Bacillus amyloliquefaciens* (BPN)' and *Bacillus lentus* (wild-type).

FIGS. 3A and 3B depict the amino acid sequence of four subtilisins. The top line represents the amino acid sequence of subtilisin from *Bacillus amyloliquefaciens* subtilisin (also sometimes referred to as subtilisin BPN'). The second line depicts the amino acid sequence of subtilisin from *Bacillus subtilis*. The third line depicts the amino acid sequence of subtilisin from *B. licheniformis*. The fourth line depicts the amino acid sequence of subtilisin from *Bacillus lentus* (also referred to as subtilisin 309 in PCT WO89/06276). The symbol * denotes the absence of specific amino acid residues as compared to subtilisin BPN'.

DETAILED DESCRIPTION OF THE INVENTION

Figure 1A:
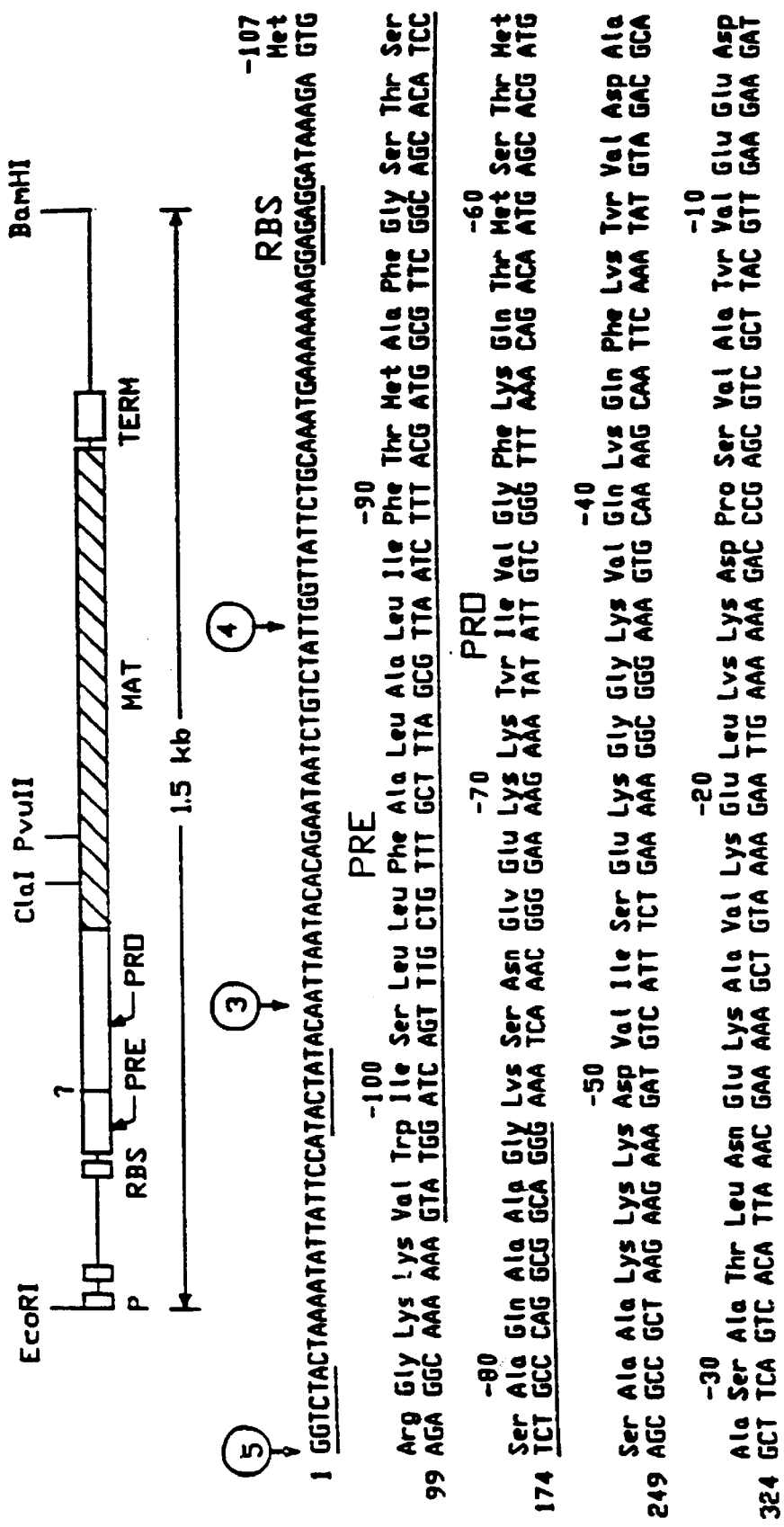

The bleaching compositions employed in the present invention provide improved and enhanced cleaning of fabrics, dishware, kitchenware, tableware, and other hard surfaces as more fully described herein by removing and/or reducing soils and/or stains from the fabrics and other hard surfaces, and by removing and/or reducing spotting and/or filming from the dishware and other hard surfaces.

The bleaching systems in combination with the protease enzymes of the present invention are particularly efficient and effective at removing most types of soils from fabrics, including protein and lipid soils, dingy soils, and heavy soil loads, especially nucleophilic and body soils.

The protease enzymes, bleaching agents (including peroxyacids and bleaching systems) and cleaning adjunct materials useful herein, including preferred levels, are described in detail hereinafter.

I Proteases

Proteases are carbonyl hydrolases which generally act to cleave peptide bonds of proteins or peptides. As used herein, "protease" means a naturally occurring protease or recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid protease are included, as well as endo and exo-proteases.

The present invention includes protease enzymes which are non-naturally occurring carbonyl hydrolase variants (protease variants) having a different proteolytic activity, stability, substrate specificity, pH profile and/or performance characteristic as compared to the precursor carbonyl hydrolase from which the amino acid sequence of the variant is derived. Specifically, such protease variants have an amino acid sequence not found in nature, which is derived by replacement of a plurality of amino acid residues of a precursor protease with different amino acids. The precursor protease may be a naturally-occurring protease or recombinant protease. As stated earlier, the protease variants are designed to have trypsin-like specificity and preferably also be bleach stable.

The protease variants useful herein encompass the substitution of any of the nineteen naturally occurring L-amino acids at the designated amino acid residue positions. Such substitutions can be made in any precursor subtilisin (procaryotic, eucaryotic, mammalian, etc.). Throughout this application reference is made to various amino acids by way of common one- and three-letter codes. Such codes are identified in Dale, M. W. (1989), *Molecular Genetics of Bacteria,* John Wiley & Sons, Ltd., Appendix B.

The protease variants useful herein are preferably derived from a Bacillus subtilisin. More preferably, the protease variants are derived from *Bacillus lentus* subtilisin and/or subtilisin 309.

Carbonyl Hydrolases

Carbonyl hydrolases are protease enzymes which hydrolyze compounds containing

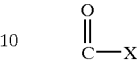

bonds in which X is oxygen or nitrogen. They include naturally-occurring carbonyl hydrolases and recombinant carbonyl hydrolases. Naturally-occurring carbonyl hydrolases principally include hydrolases, e.g., peptide hydrolases such as subtilisins or metalloproteases. Peptide hydrolases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid protease's are included, as well as endo and exo-proteases.

Subtilisins

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases share a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include, but are not limited to, the subtilisins identified in FIG. 3 herein. Generally, and for purposes of the present invention, numbering of the amino acids in proteases corresponds to the numbers assigned to the mature *Bacillus amyloliquefaciens* subtilisin sequence presented in FIG. 1.

Protease Variants

A "protease variant" has an amino acid sequence which is derived from the amino acid sequence of a "precursor protease." The precursor proteases include naturally-occurring proteases and recombinant proteases. The amino acid sequence of the protease variant is "derived" from the precursor protease amino acid sequence by substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods know to those skilled in the art (see, for example, EP 0 328 299, WO 89/06279 and the U.S. patents and applications already referenced herein).

In a preferred embodiment, the protease variants which are protease enzymes useful in the present invention bleaching compositions comprise protease variants including a substitution of an amino acid residue with another naturally occurring amino acid residue at an amino acid residue position corresponding to position 103 of *Bacillus amyloliquefaciens* subtilisin in combination with a substitution of an amino acid residue with another naturally occurring amino acid residue at one or more amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of *Bacillus amyloliquefaciens* subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 of *Bacillus amyloliquefaciens* subtilisin; and one or more cleaning adjunct materials.

While any combination of the above listed amino acid substitutions may be employed, the preferred protease variant enzymes useful for the present invention comprise the substitution, deletion or insertion of amino acid residues in the following combinations:

(1) a protease variant including substitutions of the amino acid residues at position 103 and at one or more of the following positions 236 and 245;

(2) a protease variant including substitutions of the amino acid residues at positions 103 and 236 and at one or more of the following positions 12, 61, 62, 68, 76, 97, 98, 101, 102, 104, 109, 130, 131, 159, 183, 185, 205, 209, 210, 211, 212, 213, 215, 217, 230, 232, 248, 252, 257, 260, 270 and 275;

(3) a protease variant including substitutions of the amino acid residues at positions 103 and 245 and at one or more of the following positions 12, 61, 62, 68, 76, 97, 98, 101, 102, 104, 109, 130, 131, 159, 170, 183, 185, 205, 209, 210, 211, 212, 213, 215, 217, 222, 230, 232, 248, 252, 257, 260, 261, 270 and 275; and (4) a protease variant including substitutions of the amino acid residues at positions 103, 236 and 245 and at one or more of the following positions 12, 61, 62, 68, 76, 97, 98, 101, 102, 104, 109, 130, 131, 159, 183, 185, 205, 209, 210, 211, 212, 213, 215, 217, 230, 232, 243, 248, 252, 257, 260, 270 and 275.

A more preferred protease variant useful in the cleaning compositions of the present invention include a substitution set (one substitution set per row in the following Table I) selected from the group consisting of:

TABLE I

| | | | | |
|---|---|---|---|---|
| 76 | 98 | 103 | 104 | |
| 76 | 78 | 103 | 104 | |
| 76 | 103 | 104 | 107 | |
| 4 | 76 | 103 | 104 | |
| 76 | 103 | 104 | 246 | |
| 76 | 77 | 103 | 104 | |
| 76 | 103 | 104 | 183 | 218 |
| 16 | 76 | 103 | 104 | 248 |
| 1 | 76 | 103 | 104 | |
| 76 | 103 | 104 | 261 | |
| 76 | 103 | 104 | 160 | |
| 76 | 103 | 104 | 216 | |
| 17 | 76 | 103 | 104 | |
| 37 | 76 | 103 | 104 | |
| 76 | 77 | 103 | 104 | 174 |
| 38 | 76 | 103 | 104 | |
| 38 | 76 | 103 | 104 | 237 |
| 8 | 76 | 103 | 104 | |
| 76 | 103 | 104 | 183 | |
| 19 | 76 | 103 | 104 | |
| 13 | 76 | 103 | 104 | |
| 19 | 76 | 103 | 104 | |
| 76 | 103 | 104 | 184 | |
| 76 | 103 | 104 | 252 | |
| 76 | 103 | 104 | 259 | |
| 76 | 103 | 104 | 251 | |
| 76 | 86 | 103 | 104 | |
| 72 | 76 | 103 | 104 | 185 |
| 76 | 103 | 104 | 237 | 274 |
| 76 | 103 | 104 | 160 | |
| 76 | 103 | 104 | 228 | |
| 55 | 76 | 103 | 104 | 240 |
| 76 | 103 | 104 | 254 | |
| 76 | 103 | 104 | 204 | |
| 76 | 103 | 104 | 204 | |
| 43 | 76 | 103 | 104 | |
| 76 | 103 | 104 | 159 | |
| 10 | 76 | 103 | 104 | 177 |
| 58 | 76 | 103 | 104 | |
| 76 | 103 | 104 | 270 | |
| 76 | 103 | 104 | 185 | |
| 27 | 76 | 103 | 104 | |

TABLE I-continued

|    |    |     |     |     |     |     |     |
|----|----|-----|-----|-----|-----|-----|-----|
|    | 76 | 103 | 104 | 262 |     |     |     |
|    | 76 | 78  | 103 | 104 |     |     |     |
| 24 | 76 | 103 | 104 |     |     |     |     |
|    | 76 | 103 | 104 | 166 | 236 | 251 |     |
| 17 | 76 | 103 | 104 | 237 |     |     |     |
|    | 76 | 103 | 104 | 130 |     |     |     |
|    | 76 | 103 | 104 | 109 |     |     |     |
|    | 76 | 99  | 103 | 104 | 204 |     |     |
|    | 76 | 103 | 104 | 181 |     |     |     |
| 12 | 76 | 103 | 104 |     |     |     |     |
|    | 76 | 103 | 104 | 212 | 271 |     |     |
|    | 76 | 103 | 104 | 252 | 261 |     |     |
|    | 76 | 103 | 104 | 242 |     |     |     |
|    | 76 | 103 | 104 | 271 |     |     |     |
| 12 | 76 | 103 | 104 | 242 |     |     |     |
| 43 | 76 | 103 | 104 | 116 | 183 |     |     |
|    | 76 | 103 | 104 | 258 |     |     |     |
|    | 76 | 103 | 104 | 271 |     |     |     |
| 61 | 76 | 103 | 104 |     |     |     |     |
| 38 | 76 | 103 | 104 | 182 | 263 |     |     |
|    | 76 | 103 | 104 | 182 | 272 |     |     |
|    | 76 | 103 | 104 | 109 | 246 |     |     |
|    | 76 | 87  | 103 | 104 | 206 | 249 | 265 |
|    | 76 | 103 | 104 | 137 | 238 | 271 |     |
|    | 103| 104 | 228 |     |     |     |     |
|    | 76 | 103 | 104 | 182 | 198 |     |     |
| 21 | 76 | 103 | 104 | 182 |     |     |     |
|    | 76 | 103 | 104 | 119 | 137 |     |     |
|    | 76 | 103 | 104 | 137 | 248 |     |     |
| 13 | 76 | 103 | 104 | 206 |     |     |     |
|    | 76 | 103 | 104 | 206 |     |     |     |
|    | 76 | 103 | 104 | 212 | 258 |     |     |
| 58 | 76 | 103 | 104 | 271 |     |     |     |
|    | 76 | 103 | 104 | 206 | 261 |     |     |
| 4  | 76 | 103 | 104 | 206 |     |     |     |
|    | 76 | 77  | 103 | 104 | 206 |     |     |
|    | 76 | 103 | 104 | 158 |     |     |     |
|    | 76 | 103 | 104 | 206 |     |     |     |
| 4  | 76 | 103 | 104 | 159 | 217 | 251 |     |
| 4  | 76 | 103 | 104 | 159 | 217 | 252 |     |
|    | 76 | 77  | 103 | 104 | 133 | 185 | 251 |
|    | 76 | 103 | 104 | 159 | 206 | 244 |     |
| 4  | 76 | 103 | 104 | 188 |     |     |     |
| 4  | 76 | 103 | 104 | 158 |     |     |     |
|    | 76 | 77  | 103 | 104 | 185 |     |     |
|    | 76 | 103 | 104 | 206 | 251 |     |     |
| 48 | 76 | 103 | 104 | 111 | 159 |     |     |
| 68 | 76 | 103 | 104 | 159 | 236 |     |     |
| 42 | 76 | 103 | 104 | 159 |     |     |     |
| 12 | 62 | 76  | 103 | 104 | 159 |     |     |
| 42 | 76 | 103 | 104 | 159 |     |     |     |
|    | 76 | 103 | 104 | 146 | 159 |     |     |
|    | 76 | 103 | 104 | 159 | 238 |     |     |
|    | 76 | 103 | 104 | 159 | 224 |     |     |
|    | 76 | 103 | 104 | 212 | 268 | 271 |     |
|    | 76 | 89  | 103 | 104 |     |     |     |
|    | 76 | 87  | 103 | 104 | 212 | 271 |     |
|    | 76 | 103 | 104 | 212 | 245 | 271 |     |
|    | 76 | 103 | 104 | 134 | 141 | 212 | 271 |
|    | 76 | 103 | 104 | 212 | 236 | 243 | 271 |
|    | 76 | 103 | 104 | 109 | 245 |     |     |
|    | 76 | 103 | 104 | 109 | 210 |     |     |
| 20 | 62 | 76  | 103 | 104 |     |     |     |
| 68 | 76 | 103 | 104 | 236 |     |     |     |
| 68 | 76 | 103 | 104 | 159 | 236 | 271 |     |
| 68 | 76 | 103 | 104 | 159 | 236 | 245 |     |
| 68 | 76 | 103 | 104 | 159 | 217 | 236 | 271 |
| 17 | 68 | 76  | 103 | 104 |     |     |     |
| 68 | 76 | 103 | 104 |     |     |     |     |
| 68 | 76 | 103 | 104 | 159 | 236 |     |     |
| 68 | 75 | 76  | 103 | 104 | 159 | 236 |     |
| 68 | 76 | 76  | 103 | 114 | 121 | 159 | 236 | 245 |
| 12 | 68 | 76  | 103 | 104 | 159 | 236 |     |
| 68 | 76 | 103 | 104 | 159 | 209 | 236 | 253 |
| 68 | 76 | 103 | 104 | 117 | 159 | 184 | 236 |
| 68 | 76 | 103 | 104 | 159 | 236 | 243 |     |
| 68 | 76 | 103 | 104 | 159 | 236 | 245 |     |
| 68 | 76 | 103 | 104 | 142 | 159 |     |     |
| 68 | 76 | 103 | 104 | 123 | 159 | 236 | 249 |

TABLE I-continued

| | | | | | | | | |
|---|---|---|---|---|---|---|---|---|
| 68 | 76 | 103 | 104 | 159 | 236 | 249 | | |
| 76 | 103 | 104 | 222 | 245 | | | | |
| 12 | 76 | 103 | 104 | 222 | 249 | | | |
| 76 | 103 | 104 | 173 | 222 | | | | |
| 76 | 103 | 104 | 222 | 263 | | | | |
| 21 | 76 | 103 | 104 | 222 | 237 | 263 | | |
| 76 | 103 | 104 | 109 | 222 | | | | |
| 76 | 103 | 104 | 109 | 222 | 271 | | | |
| 61 | 76 | 103 | 104 | 222 | | | | |
| 76 | 103 | 104 | 137 | 222 | | | | |
| 76 | 103 | 104 | 109 | 222 | 248 | | | |
| 76 | 103 | 104 | 222 | 249 | | | | |
| 68 | 76 | 103 | 104 | 159 | 236 | 245 | 261 | |
| 68 | 76 | 103 | 104 | 141 | 159 | 236 | 245 | 255 |
| 68 | 76 | 103 | 104 | 159 | 236 | 245 | 247 | |
| 68 | 76 | 103 | 104 | 159 | 174 | 204 | 236 | 245 |
| 68 | 76 | 103 | 104 | 159 | 204 | 236 | 245 | |
| 68 | 76 | 103 | 104 | 133 | 159 | 218 | 236 | 245 |
| 68 | 76 | 103 | 104 | 159 | 232 | 236 | 245 | |
| 68 | 76 | 103 | 104 | 159 | 194 | 203 | 236 | 245 |
| 12 | 76 | 103 | 104 | 222 | 245 | | | |
| 76 | 103 | 104 | 232 | 245 | | | | |
| 24 | 68 | 76 | 103 | 104 | 159 | 232 | 236 | 245 |
| 68 | 103 | 104 | 159 | 232 | 236 | 245 | 252 | |
| 68 | 76 | 103 | 104 | 159 | 213 | 232 | 236 | 245 | 260 |
| 12 | 76 | 103 | 104 | 222 | 244 | 245 | | |
| 12 | 76 | 103 | 222 | 210 | 245 | | | |
| 12 | 76 | 103 | 104 | 130 | 222 | 245 | | |
| 22 | 68 | 76 | 103 | 104 | | | | |
| 68 | 76 | 103 | 104 | 184 | | | | |
| 68 | 103 | 104 | 159 | 232 | 236 | 245 | 248 | 252 |
| 68 | 103 | 104 | 159 | 232 | 236 | 245 | | |
| 68 | 103 | 104 | 140 | 159 | 232 | 236 | 245 | 252 |
| 43 | 68 | 103 | 104 | 159 | 232 | 236 | 245 | |
| 43 | 68 | 103 | 104 | 159 | 232 | 236 | 245 | 252 |
| 68 | 87 | 103 | 104 | 159 | 232 | 236 | 245 | 252 | 275 |
| 12 | 76 | 103 | 104 | 130 | 222 | 245 | 248 | 262 |
| 12 | 76 | 103 | 104 | 130 | 215 | 222 | 245 | |
| 12 | 76 | 103 | 104 | 130 | 222 | 227 | 245 | 262 |
| 12 | 76 | 103 | 104 | 130 | 222 | 245 | 261 | |
| 76 | 103 | 104 | 130 | 222 | 245 | | | |
| 12 | 76 | 103 | 104 | 130 | 218 | 222 | 245 | 262 | 269 |
| 12 | 57 | 76 | 103 | 104 | 130 | 222 | 245 | 251 |
| 12 | 76 | 103 | 104 | 130 | 170 | 185 | 222 | 243 | 245 |
| 12 | 76 | 103 | 104 | 130 | 222 | 245 | 268 | |
| 12 | 76 | 103 | 104 | 130 | 222 | 210 | 245 | |
| 68 | 103 | 104 | 159 | 232 | 236 | 245 | 257 | |
| 68 | 103 | 104 | 116 | 159 | 232 | 236 | 245 | |
| 68 | 103 | 104 | 159 | 232 | 236 | 245 | 248 | |
| 10 | 68 | 103 | 104 | 159 | 232 | 236 | 245 | |
| 68 | 103 | 104 | 159 | 203 | 232 | 236 | 245 | |
| 68 | 103 | 104 | 159 | 232 | 236 | 237 | 245 | |
| 68 | 76 | 79 | 103 | 104 | 159 | 232 | 236 | 245 |
| 68 | 103 | 104 | 159 | 183 | 232 | 236 | 245 | |
| 68 | 103 | 104 | 159 | 174 | 206 | 232 | 236 | 245 |
| 68 | 103 | 104 | 159 | 188 | 232 | 236 | 245 | |
| 68 | 103 | 104 | 159 | 230 | 232 | 236 | 245 | |
| 68 | 98 | 103 | 104 | 159 | 232 | 236 | 245 | |
| 68 | 103 | 104 | 159 | 215 | 232 | 236 | 245 | |
| 68 | 103 | 104 | 159 | 232 | 236 | 245 | 248 | |
| 68 | 76 | 103 | 104 | 159 | 232 | 236 | 245 | |
| 68 | 76 | 103 | 104 | 159 | 210 | 232 | 236 | 245 |
| 68 | 76 | 103 | 104 | 159 | 232 | 236 | 245 | 257 |
| 76 | 103 | 104 | 232 | 236 | 245 | 257 | | |
| 68 | 103 | 104 | 159 | 232 | 236 | 245 | 257 | 275 |
| 76 | 103 | 104 | 257 | 275 | | | | |
| 68 | 103 | 104 | 159 | 224 | 232 | 236 | 245 | 257 |
| 76 | 103 | 104 | 159 | 232 | 236 | 245 | 257 | |
| 68 | 76 | 103 | 104 | 159 | 209 | 232 | 236 | 245 |
| 68 | 76 | 103 | 104 | 159 | 211 | 232 | 236 | 245 |
| 12 | 68 | 76 | 103 | 104 | 159 | 214 | 232 | 236 | 245 |
| 68 | 76 | 103 | 104 | 159 | 215 | 232 | 236 | 245 |
| 12 | 68 | 76 | 103 | 104 | 159 | 232 | 236 | 245 |
| 20 | 68 | 76 | 103 | 104 | 159 | 232 | 236 | 245 | 259 |
| 68 | 87 | 76 | 103 | 104 | 159 | 232 | 236 | 245 | 260 |
| 68 | 76 | 103 | 104 | 159 | 232 | 236 | 245 | 261 |
| 76 | 103 | 104 | 232 | 236 | 242 | 245 | | |
| 68 | 76 | 103 | 104 | 159 | 210 | 232 | 236 | 245 |

TABLE I-continued

| | | | | | | | | | | | |
|---|---|---|---|---|---|---|---|---|---|---|---|
| 12 | 48 | 68 | 76 | 103 | 104 | 159 | 232 | 236 | 245 | | |
| 76 | 103 | 104 | 232 | 236 | 245 | | | | | | |
| 76 | 103 | 104 | 159 | 192 | 232 | 236 | 245 | | | | |
| 76 | 103 | 104 | 147 | 159 | 232 | 236 | 245 | 248 | 251 | | |
| 12 | 68 | 76 | 103 | 104 | 159 | 232 | 236 | 245 | 272 | | |
| 68 | 76 | 103 | 104 | 159 | 183 | 206 | 232 | 236 | 245 | | |
| 68 | 76 | 103 | 104 | 159 | 232 | 236 | 245 | 256 | | | |
| 68 | 76 | 103 | 104 | 159 | 206 | 232 | 236 | 245 | | | |
| 27 | 68 | 76 | 103 | 104 | 159 | 232 | 236 | 245 | | | |
| 68 | 76 | 103 | 104 | 116 | 159 | 170 | 185 | 232 | 236 | 245 | |
| 61 | 68 | 103 | 104 | 159 | 232 | 236 | 245 | 248 | 252 | | |
| 43 | 68 | 103 | 104 | 159 | 232 | 236 | 245 | 248 | 252 | | |
| 68 | 103 | 104 | 159 | 212 | 232 | 236 | 245 | 248 | 252 | | |
| 68 | 103 | 104 | 99 | 159 | 184 | 232 | 236 | 245 | 248 | 252 | |
| 103 | 104 | 159 | 232 | 236 | 245 | 248 | 252 | | | | |
| 68 | 103 | 104 | 159 | 209 | 232 | 236 | 245 | 248 | 252 | | |
| 68 | 103 | 104 | 109 | 159 | 232 | 236 | 245 | 248 | 252 | | |
| 20 | 68 | 103 | 104 | 159 | 232 | 236 | 245 | 248 | 252 | | |
| 68 | 103 | 104 | 159 | 209 | 232 | 236 | 245 | 248 | 252 | | |
| 68 | 103 | 104 | 159 | 232 | 236 | 245 | 248 | 252 | 261 | | |
| 68 | 103 | 104 | 159 | 185 | 232 | 236 | 245 | 248 | 252 | | |
| 68 | 103 | 104 | 159 | 210 | 232 | 236 | 245 | 248 | 252 | | |
| 68 | 103 | 104 | 159 | 185 | 210 | 232 | 236 | 245 | 248 | 252 | |
| 68 | 103 | 104 | 159 | 212 | 232 | 236 | 245 | 248 | 252 | | |
| 68 | 103 | 104 | 159 | 213 | 232 | 236 | 245 | 248 | 252 | | |
| 68 | 103 | 104 | 213 | 232 | 236 | 245 | 248 | 252 | | | |
| 68 | 103 | 104 | 159 | 215 | 232 | 236 | 245 | 248 | 252 | | |
| 68 | 103 | 104 | 159 | 216 | 232 | 236 | 245 | 248 | 252 | | |
| 20 | 68 | 103 | 104 | 159 | 232 | 236 | 245 | 248 | 252 | | |
| 68 | 103 | 104 | 159 | 173 | 232 | 236 | 245 | 248 | 252 | | |
| 68 | 103 | 104 | 159 | 232 | 236 | 245 | 248 | 251 | 252 | | |
| 68 | 103 | 104 | 159 | 206 | 232 | 236 | 245 | 248 | 252 | | |
| 68 | 103 | 104 | 159 | 232 | 236 | 245 | 248 | 252 | | | |
| 55 | 68 | 103 | 104 | 159 | 232 | 236 | 245 | 248 | 252 | | |
| 68 | 103 | 104 | 159 | 232 | 236 | 245 | 248 | 252 | 255 | | |
| 68 | 103 | 104 | 159 | 232 | 236 | 245 | 248 | 252 | 256 | | |
| 68 | 103 | 104 | 159 | 232 | 236 | 245 | 248 | 252 | 260 | | |
| 68 | 103 | 104 | 159 | 232 | 236 | 245 | 248 | 252 | 257 | | |
| 68 | 103 | 104 | 159 | 232 | 236 | 245 | 248 | 252 | 258 | | |
| 8 | 68 | 103 | 104 | 159 | 232 | 236 | 245 | 248 | 252 | 269 | |
| 68 | 103 | 104 | 116 | 159 | 232 | 236 | 245 | 248 | 252 | 260 | |
| 68 | 103 | 104 | 159 | 232 | 236 | 245 | 248 | 252 | 261 | | |
| 68 | 103 | 104 | 159 | 232 | 236 | 245 | 248 | 252 | 261 | | |
| 68 | 76 | 103 | 104 | 159 | 232 | 236 | 245 | 248 | 252 | | |
| 68 | 103 | 104 | 232 | 236 | 245 | 248 | 252 | | | | |
| 103 | 104 | 159 | 232 | 236 | 245 | 248 | 252 | | | | |
| 68 | 103 | 104 | 159 | 232 | 236 | 245 | 248 | 252 | | | |
| 18 | 68 | 103 | 104 | 159 | 232 | 236 | 245 | 248 | 252 | | |
| 68 | 103 | 104 | 159 | 232 | 236 | 245 | 248 | 252 | | | |
| 68 | 76 | 101 | 103 | 104 | 159 | 213 | 218 | 232 | 236 | 245 | 260 |
| 68 | 103 | 104 | 159 | 228 | 232 | 236 | 245 | 248 | 252 | | |
| 33 | 68 | 76 | 103 | 104 | 159 | 232 | 236 | 245 | 248 | 252 | |
| 68 | 76 | 89 | 103 | 104 | 159 | 210 | 213 | 232 | 236 | 245 | 260 |
| 61 | 68 | 76 | 103 | 104 | 159 | 232 | 236 | 245 | 248 | 252 | |
| 103 | 104 | 159 | 205 | 210 | 232 | 236 | 245 | | | | |
| 61 | 68 | 103 | 104 | 130 | 159 | 232 | 236 | 245 | 248 | 252 | |
| 61 | 68 | 103 | 104 | 133 | 137 | 159 | 232 | 236 | 245 | 248 | 252 |
| 61 | 103 | 104 | 133 | 159 | 232 | 236 | 245 | 248 | 252 | | |
| 68 | 103 | 104 | 159 | 232 | 236 | 245 | 248 | 252 | | | |
| 68 | 103 | 104 | 159 | 218 | 232 | 236 | 245 | 248 | 252 | | |
| 61 | 68 | 103 | 104 | 159 | 160 | 232 | 236 | 245 | 248 | 252 | |
| 3 | 61 | 68 | 76 | 103 | 104 | 232 | 236 | 245 | 248 | 252 | |
| 61 | 68 | 103 | 104 | 159 | 167 | 232 | 236 | 245 | 248 | 252 | |
| 97 | 103 | 104 | 159 | 232 | 236 | 245 | 248 | 252 | | | |
| 98 | 103 | 104 | 159 | 232 | 236 | 245 | 248 | 252 | | | |
| 99 | 103 | 104 | 159 | 232 | 236 | 245 | 248 | 252 | | | |
| 101 | 103 | 104 | 159 | 232 | 236 | 245 | 248 | 252 | | | |
| 102 | 103 | 104 | 159 | 232 | 236 | 245 | 248 | 252 | | | |
| 103 | 104 | 106 | 159 | 232 | 236 | 245 | 248 | 252 | | | |
| 103 | 104 | 109 | 159 | 232 | 236 | 245 | 248 | 252 | | | |
| 103 | 104 | 159 | 232 | 236 | 245 | 248 | 252 | 261 | | | |
| 62 | 103 | 104 | 159 | 232 | 236 | 245 | 248 | 252 | | | |
| 103 | 104 | 159 | 184 | 232 | 236 | 245 | 248 | 252 | | | |
| 103 | 104 | 159 | 166 | 232 | 236 | 245 | 248 | 252 | | | |
| 103 | 104 | 159 | 217 | 232 | 236 | 245 | 248 | 252 | | | |
| 20 | 62 | 103 | 104 | 159 | 213 | 232 | 236 | 245 | 248 | 252 | |
| 62 | 103 | 104 | 159 | 213 | 232 | 236 | 245 | 248 | 252 | | |
| 103 | 104 | 159 | 206 | 217 | 232 | 236 | 245 | 248 | 252 | | |
| 62 | 103 | 104 | 159 | 206 | 232 | 236 | 245 | 248 | 252 | | |

TABLE I-continued

| | | | | | | | | | | |
|---|---|---|---|---|---|---|---|---|---|---|
| 103 | 104 | 130 | 159 | 232 | 236 | 245 | 248 | 252 | | |
| 103 | 104 | 131 | 159 | 232 | 236 | 245 | 248 | 252 | | |
| 27 | 103 | 104 | 159 | 232 | 236 | 245 | 248 | 252 | | |
| 38 | 103 | 104 | 159 | 232 | 236 | 245 | 248 | 252 | | |
| 38 | 76 | 103 | 104 | 159 | 213 | 232 | 236 | 245 | 260 | |
| 68 | 76 | 103 | 104 | 159 | 213 | 232 | 236 | 245 | 260 | 271 |
| 68 | 76 | 103 | 104 | 159 | 209 | 213 | 232 | 236 | 245 | 260 |
| 68 | 76 | 103 | 104 | 159 | 210 | 213 | 232 | 236 | 245 | 260 |
| 68 | 76 | 103 | 104 | 159 | 205 | 213 | 232 | 236 | 245 | 260 |
| 68 | 76 | 103 | 104 | 159 | 210 | 232 | 236 | 245 | 260 | |
| 68 | 103 | 104 | 159 | 213 | 232 | 236 | 245 | 260 | | |
| 76 | 103 | 104 | 159 | 213 | 232 | 236 | 245 | 260 | | |
| 68 | 103 | 104 | 159 | 209 | 232 | 236 | 245 | | | |
| 68 | 103 | 104 | 159 | 210 | 232 | 236 | 245 | | | |
| 68 | 103 | 104 | 159 | 230 | 232 | 236 | 245 | | | |
| 68 | 103 | 104 | 159 | 126 | 232 | 236 | 245 | | | |
| 68 | 103 | 104 | 159 | 205 | 232 | 236 | 245 | | | |
| 68 | 103 | 104 | 159 | 210 | 232 | 236 | 245 | | | |
| 103 | 104 | 159 | 230 | 236 | 245 | | | | | |
| 68 | 103 | 104 | 159 | 232 | 236 | 245 | 260 | | | |
| 103 | 104 | 159 | 232 | 236 | 245 | | | | | |
| 68 | 103 | 104 | 159 | 174 | 232 | 236 | 245 | 257 | | |
| 68 | 103 | 104 | 159 | 194 | 232 | 236 | 245 | 257 | | |
| 68 | 103 | 104 | 159 | 209 | 232 | 236 | 245 | 257 | | |
| 103 | 104 | 159 | 232 | 236 | 245 | 257 | | | | |
| 68 | 76 | 103 | 104 | 159 | 213 | 232 | 236 | 245 | 260 | 261 |
| 68 | 103 | 104 | 159 | 232 | 236 | 245 | 257 | 261 | | |
| 103 | 104 | 159 | 213 | 232 | 236 | 245 | 260 | | | |
| 103 | 104 | 159 | 210 | 232 | 236 | 245 | 248 | 252 | | |
| 103 | 104 | 159 | 209 | 232 | 236 | 245 | 257 | | | |
| 68 | 76 | 103 | 104 | 159 | 210 | 213 | 232 | 236 | 245 | 260 |
| 12 | 103 | 104 | 159 | 209 | 213 | 232 | 236 | 245 | 260 | |
| 103 | 104 | 209 | 232 | 236 | 245 | 257 | | | | |
| 103 | 104 | 159 | 205 | 210 | 213 | 232 | 236 | 245 | 260 | |
| 103 | 104 | 159 | 205 | 209 | 232 | 236 | 245 | 260 | | |
| 68 | 103 | 104 | 159 | 205 | 209 | 210 | 232 | 236 | 245 | |
| 103 | 104 | 159 | 205 | 209 | 210 | 232 | 236 | 245 | 257 | |
| 103 | 104 | 159 | 205 | 209 | 232 | 236 | 245 | 257 | | |
| 68 | 103 | 104 | 159 | 205 | 209 | 210 | 232 | 236 | 245 | 260 |
| 103 | 104 | 159 | 205 | 209 | 210 | 232 | 236 | 245 | | |
| 103 | 104 | 159 | 209 | 210 | 232 | 236 | 245 | | | |
| 103 | 104 | 159 | 205 | 210 | 232 | 236 | 245 | | | |
| 68 | 103 | 104 | 128 | 159 | 232 | 236 | 245 | | | |
| 48 | 103 | 104 | 159 | 230 | 236 | 245 | | | | |
| 48 | 68 | 103 | 104 | 159 | 209 | 232 | 236 | 245 | | |
| 48 | 68 | 103 | 104 | 159 | 232 | 236 | 245 | 248 | 252 | |
| 48 | 68 | 103 | 104 | 159 | 232 | 236 | 245 | 257 | 261 | |
| 102 | 103 | 104 | 159 | 212 | 232 | 236 | 245 | 248 | 252 | |
| 12 | 102 | 103 | 104 | 159 | 212 | 232 | 236 | 245 | 248 | 252 |
| 101 | 102 | 103 | 104 | 159 | 212 | 232 | 236 | 245 | 248 | 252 |
| 98 | 102 | 103 | 104 | 159 | 212 | 232 | 236 | 245 | 248 | 252 |
| 102 | 103 | 104 | 159 | 213 | 232 | 236 | 245 | 248 | 252 | |
| 103 | 104 | 131 | 159 | 232 | 236 | 245 | 248 | 252 | | |
| 103 | 104 | 159 | 184 | 232 | 236 | 245 | 248 | 252 | | |
| 103 | 104 | 159 | 232 | 236 | 244 | 245 | 248 | 252 | | |
| 62 | 103 | 104 | 159 | 213 | 232 | 236 | 245 | 248 | 252 | 256 |
| 12 | 62 | 103 | 104 | 159 | 213 | 232 | 236 | 245 | 248 | 252 |
| 101 | 103 | 104 | 159 | 185 | 232 | 236 | 245 | 248 | 252 | |
| 101 | 103 | 104 | 159 | 206 | 232 | 236 | 245 | 248 | 252 | |
| 101 | 103 | 104 | 159 | 213 | 232 | 236 | 245 | 248 | 252 | |
| 98 | 102 | 103 | 104 | 159 | 232 | 236 | 245 | 248 | 252 | |
| 101 | 102 | 103 | 104 | 159 | 232 | 236 | 245 | 248 | 252 | |
| 98 | 102 | 103 | 104 | 159 | 212 | 232 | 236 | 245 | 248 | 252 |
| 98 | 102 | 103 | 104 | 159 | 212 | 232 | 236 | 245 | 248 | 252 |
| 62 | 103 | 104 | 109 | 159 | 213 | 232 | 236 | 245 | 248 | 252 |
| 62 | 103 | 104 | 159 | 212 | 213 | 232 | 236 | 245 | 248 | 252 |
| 62 | 101 | 103 | 104 | 159 | 212 | 213 | 232 | 236 | 245 | 248 | 252 |
| 103 | 104 | 159 | 232 | 245 | 248 | 252 | | | | |
| 103 | 104 | 159 | 230 | 245 | | | | | | |
| 62 | 103 | 104 | 130 | 159 | 213 | 232 | 236 | 245 | 248 | 252 |
| 101 | 103 | 104 | 130 | 159 | 232 | 236 | 245 | 248 | 252 | |
| 101 | 103 | 104 | 128 | 159 | 232 | 236 | 245 | 248 | 252 | |
| 62 | 101 | 103 | 104 | 159 | 213 | 232 | 236 | 245 | 248 | 252 |
| 62 | 103 | 104 | 128 | 159 | 213 | 232 | 236 | 245 | 248 | 252 |
| 62 | 103 | 104 | 128 | 159 | 213 | 232 | 236 | 245 | 248 | 252 |
| 101 | 103 | 104 | 159 | 232 | 236 | 245 | 248 | 252 | 260 | |
| 101 | 103 | 104 | 131 | 159 | 232 | 236 | 245 | 248 | 252 | |
| 98 | 101 | 103 | 104 | 159 | 232 | 236 | 245 | 248 | 252 | |
| 99 | 101 | 103 | 104 | 159 | 232 | 236 | 245 | 248 | 252 | |

TABLE I-continued

| | | | | | | | | | | | | |
|---|---|---|---|---|---|---|---|---|---|---|---|---|
| 101 | 103 | 104 | 159 | 212 | 232 | 236 | 245 | 248 | 252 | | | |
| 76 | 103 | 104 | 167 | 170 | 194 | | | | | | | |
| 101 | 103 | 104 | 159 | 209 | 232 | 236 | 245 | 248 | 252 | | | |
| 101 | 103 | 104 | 159 | 210 | 232 | 236 | 245 | 248 | 252 | | | |
| 101 | 103 | 104 | 159 | 205 | 232 | 236 | 245 | 248 | 252 | | | |
| 101 | 103 | 104 | 159 | 230 | 236 | 245 | | | | | | |
| 101 | 103 | 104 | 159 | 194 | 232 | 236 | 245 | 248 | 252 | | | |
| 76 | 101 | 103 | 104 | 159 | 194 | 232 | 236 | 245 | 248 | 252 | | |
| 101 | 103 | 104 | 159 | 230 | 232 | 236 | 245 | 248 | 252 | | | |
| 62 | 103 | 104 | 159 | 185 | 206 | 213 | 232 | 236 | 245 | 248 | 252 | 271 |

An even more preferred protease variant useful in the cleaning compositions of the present invention include a substitution set (one substitution set per row in the following Table II) selected from the group consisting of:

TABLE II

| | | | | |
|---|---|---|---|---|
| N76D | A98E | S103A | V104I | |
| N76D | S78T | S103A | V104I | |
| N76D | S103A | V104I | I107V | |
| V4E | N76D | S103A | V104I | |
| N76D | S103A | V104I | I246V | |
| N76D | N77D | 5103A | V104I | |
| N76D | S103A | V104I | N183D | N218I |
| A16T | N76D | S103A | V104I | N248D |
| A1E | N76D | S103A | V104I | |
| N76D | S103A | V104I | N261D | |
| N76D | S103A | V104I | S160T | |
| N76D | S103A | V104I | S216C | |
| H17Q | N76D | S103A | V104I | |
| S37T | N76D | S103A | V104I | |
| N76D | N77D | S103A | V104I | A174V |
| T38S | N76D | S103A | V104I | |
| T38S | N76D | S103A | V104I | K237Q |
| 18V | N76D | S103A | V104I | |
| N76D | S103A | V104I | N183D | |
| R19L | N76D | S103A | V104I | |
| A13V | N76D | S103A | V104I | |
| R19C | N76D | S103A | V104I | |
| N76D | S103A | V104I | N184D | |
| N76D | S103A | V104I | N252D | |
| N76D | S103A | V104I | S259C | |
| N76D | S103A | V104I | K251T | |
| N76D | P86S | S103A | V104I | |
| I72V | N76D | S103A | V104I | N185D |
| N76D | S103A | V104I | K237E | T274A |
| N76D | S103A | V104I | S160L | |
| N76D | S103A | V104J | A228V | |
| P55S | N76D | S103A | V104I | S240T |
| N76D | S103A | V104I | A254T | |
| N76D | S103A | I104N | N204T | |
| N76D | S103A | V104I | N204D | |
| N43S | N76D | S103A | V104I | |
| N76D | S103A | V104I | G159D | |
| R10H | N76D | S103A | V104I | V177A |
| T58S | N76D | S103A | V104I | |
| N76D | S103A | V104I | A270V | |
| N76D | S103A | V104T | N185D | |
| K27N | N76D | S103A | V104I | |
| N76D | S103A | V104I | L262M | |
| N76D | S78P | S103A | V104I | |
| S24P | N76D | S103A | V104I | |
| N76D | S103A | V104I | S166G | Q236R K251R |
| H17L | N76D | S103A | V104I | K237E |
| N76D | S103A | V104I | S130L | |
| N76D | S103A | V104I | Q109R | |
| N76D | S99R | S103A | V104I | N204T |
| N76D | S103A | V104I | D181N | |
| Q12R | N76D | S103A | V104I | |
| N76D | S103A | V104I | S212P | E271V |
| N76D | S103A | V104I | N252K | N261Y |
| N76D | S103A | V104I | S242T | |
| N76D | S103A | V104I | E271Q | |
| Q12R | N76D | S103A | V104I | S242T |
| N43S | N76D | S103A | V104I | N116K N183I |
| N76D | S103A | V104I | G258R | |

TABLE II-continued

| | | | | | | | |
|---|---|---|---|---|---|---|---|
| N76D | S103A | V104I | E271G | | | | |
| G61R | N76D | S103A | V104I | | | | |
| T38S | N76D | S103A | V104I | Q182R | Y263R | | |
| N76D | S103A | V104I | Q182R | A272S | | | |
| N76D | S103A | V104I | Q109R | I246V | | | |
| N76D | S87G | S103A | V104I | Q206R | H249Q | S265G | |
| N76D | S103A | V104I | Q137R | N238Y | E271V | | |
| S103A | V104I | A228T | | | | | |
| N76D | S103A | V104I | Q182R | I198V | | | |
| L21M | N76D | S103A | V104I | Q182R | | | |
| N76D | S103A | V104I | M119I | Q137R | | | |
| N76D | S103A | V104I | Q137R | N248S | | | |
| A13T | N76D | S103A | V104I | Q206R | | | |
| N76D | S103A | V104I | Q206R | | | | |
| N76D | S103A | V104I | S212P | G258R | | | |
| T58S | N76D | S103A | V104I | E271G | | | |
| N76D | S103A | V104I | Q206E | N261D | | | |
| V4E | N76D | S103A | V104I | Q206E | | | |
| N76D | N77D | S103A | V104I | Q206E | | | |
| N76D | S103A | V104I | A158E | | | | |
| N76D | S103A | V104I | Q206E | | | | |
| V4E | N76D | S103A | V104I | G159D | L217E | K251Q | |
| V4E | N76D | S103A | V104I | G159D | L217E | N252D | |
| N76D | N77D | S103A | V104I | A133T | N185D | K251T | |
| N76D | S103A | V104I | G159D | Q206E | V244A | | |
| V4E | N76D | S103A | V104I | S188E | | | |
| V4E | N76D | S103A | V104I | A158E | | | |
| N76D | N77D | S103A | V104I | N185D | | | |
| N76D | S103A | V104I | Q206E | K251T | | | |
| A48T | N76D | S103A | V104I | L111M | G159D | | |
| V68A | N76D | S103A | V104I | G159D | Q236H | | |
| LA2V | N76D | S103A | V104I | G159D | | | |
| Q12H | N62H | N76D | S103A | V104I | G159D | | |
| L42I | N76D | S103A | V104I | G159D | | | |
| N76D | S103A | V104I | G146S | G159D | | | |
| N76D | S103A | V104I | G159D | N238S | | | |
| N76D | S103A | V104I | G159D | T224A | | | |
| N76D | S103A | V104I | S212P | V268F | E271V | | |
| N76D | E89A | S103A | V104I | | | | |
| N76D | S87R | S103A | V104I | S212P | E271V | | |
| N76D | S103A | V104I | S212P | Q245L | E271V | | |
| N76D | S103A | V104I | T134S | S141N | S212P | E271V | |
| N76D | S103A | V104I | S212P | Q236L | N243S | E271V | |
| N76D | S103A | V104I | Q109R | Q245R | | | |
| N76D | S103A | V104I | Q109R | P210L | | | |
| G20V | N62S | N76D | S103A | V104I | | | |
| V68A | N76D | S103A | V104I | Q236H | | | |
| V68A | N76D | S103A | V104I | G159D | Q236H | E271V | |
| V68A | N76D | S103A | V104I | G159D | Q236H | Q245R | |
| V68A | N76D | S103A | V104I | G159D | L217I | Q236H | E271V |
| H17Q | V68A | N76D | S103A | V104I | | | |
| V68A | N76D | S103A | V104I | | | | |
| V68A | N76D | S103A | V104I | G159D | Q236R | | |
| V68A | L75R | N76D | S103A | V104I | G159D | Q236H | |
| V68A | N76D | N76D | S103A | A114V | V121I | G159D | Q236H Q245R |
| Q12R | V68A | N76D | S103A | V104I | G159D | Q236H | |
| V68A | N76D | S103A | V104I | G159D | Y209S | Q236H | T253K |
| V68A | N76D | S103A | V104I | N117K | G159D | N184S | Q236H |
| V68A | N76D | S103A | V104I | G159D | Q236H | N243I | |
| V68A | N76D | S103A | V104I | G159D | Q236H | Q245L | |
| V68A | N76D | S103A | V104I | A142V | G159D | | |
| V68A | N76D | S103A | V104I | N123S | G159D | Q236H | H249Y |
| V68A | N76D | S103A | V104I | G159D | Q236H | H249Q | |
| N76D | S103A | V104I | M222S | Q245R | | | |
| Q12R | N76D | S103A | V104I | M222S | H249R | | |
| N76D | S103A | V104I | N173R | M222S | | | |
| N76D | S103A | V104I | M222S | Y263F | | | |
| L21M | N76D | S103A | V104I | M222S | K237R | Y263F | |
| N76D | S103A | V104I | Q109R | M222S | | | |
| N76D | S103A | V104I | Q109R | M222S | E271D | | |
| G61R | N76D | S103A | V104I | M222S | | | |
| N76D | S103A | V104I | Q137R | M222S | | | |
| N76D | S103A | V104I | Q109R | M222S | N248S | | |
| N76D | S103A | V104I | M222S | H249R | | | |
| V68A | N76D | S103A | V104I | G159D | Q236H | Q245R | N261D |
| V68A | N76D | S103A | V104I | 5141N | G159D | Q236H | Q245R T255S |
| V68A | N76D | S103A | V104I | G159D | Q236H | Q245R | R247H |
| V68A | N76D | S103A | V104I | G159D | A174V | N204D | Q236H Q245R |
| V68A | N76D | S103A | V104I | G159D | N204D | Q236H | Q245R |

TABLE II-continued

| | | | | | | | | | |
|---|---|---|---|---|---|---|---|---|---|
| V68A | N76D | S103A | V104I | A133V | G159D | N215D | Q236H | Q245R | |
| V68A | N76D | S103A | V104I | G159D | A232V | Q236H | Q245R | | |
| V68A | N76D | S103A | V104I | G159D | A194I | V203A | Q236H | Q245R | |
| Q12R | N76D | S103A | V104I | M222S | Q245R | | | | |
| N76D | S103A | V104I | A232V | Q245R | | | | | |
| S24T | V68A | N76D | S103A | V104I | G159D | A232V | Q236H | Q245R | |
| V68A | S103A | V104I | G159D | A232V | Q236H | Q245R | N252K | | |
| V68A | N76D | S103A | V104I | G159D | T213R | A232V | Q236H | Q245R | T260A |
| Q12R | N76D | S103A | I104T | M222S | V244I | Q245R | | | |
| Q12R | N76D | S103A | M222S | P210T | Q245R | | | | |
| Q12R | N76D | S103A | I104T | S130T | M222S | Q245R | | | |
| T22K | V68A | N76D | S103A | V104I | | | | | |
| V68A | N76D | S103A | V104I | N184D | | | | | |
| V68A | S103A | V104I | G159D | A232V | Q236H | Q245R | N248D | N252K | |
| V68A | S103A | V104I | G159D | A232V | Q236H | Q245R | | | |
| V68A | S103A | V104I | N140D | G159D | A232V | Q236H | Q245R | N252K | |
| N43S | V68A | S103A | V104I | G159D | A232V | Q236H | Q245R | N252K | |
| N43K | V68A | S103A | V104I | G159D | A232V | Q236H | Q245R | | |
| N43D | V68A | S103A | V104I | G159D | A232V | Q236H | Q245R | N252K | |
| V6SA | 587G | S103A | V104I | G159D | A232V | Q236H | Q245R | N252K | R275S |
| Q12R | N76D | S103A | I104T | S130T | M222S | Q245R | N248S | L262M | |
| Q12R | N76D | S103A | I104T | S130T | A215V | M222S | Q245R | | |
| Q12R | N76D | S103A | I104T | S130T | M222S | V227A | Q245R | L262S | |
| Q12R | N76D | S103A | I104T | S130T | A215T | M222S | Q245R | | |
| Q12R | N76D | S103A | I104T | S130T | M222S | Q245R | N261D | | |
| N76D | S103A | I104T | S130T | M222S | Q245R | | | | |
| Q12R | N76D | S103A | I104T | S130T | N218D | M222S | Q245R | L262S | N269D |
| Q12R | S57P | N76D | S103A | I104T | S130T | M222S | Q245R | K251Q | |
| Q12R | N76D | S103A | I104T | S130T | R170S | N185D | M222S | N243D | Q245R |
| Q12R | N76D | S103A | I104T | S130T | M222S | V268A | | | |
| Q12R | N76D | S103A | I104T | S130T | M222S | P210S | Q245R | | |
| V6SA | S103A | V104I | G159D | A232V | Q236H | Q245R | L257V | | |
| V68A | S103A | V104I | N116D | G159D | A232V | Q236H | Q245R | N248D | |
| V68A | S103A | V104I | G159D | A232V | Q236H | Q245R | | | |
| R10C | V68A | S103A | V104I | G159D | A232V | Q236H | Q245R | | |
| V6SA | S103A | V104I | G159D | V203E | A232V | Q236H | Q245R | | |
| V68A | S103A | V104I | G159D | A232V | K237E | Q245R | | | |
| V68A | N76D | 179N | S103A | V104I | G159D | A232V | Q236H | Q245R | |
| V68A | S103A | V104I | G159D | N183D | A232V | Q236H | Q245R | | |
| V68A | S103A | V104I | G159D | A174V | Q206L | A232V | Q236H | Q245R | |
| V68A | S103A | V104I | G159D | S188C | A232V | Q236H | Q245R | | |
| V68A | S103A | V104I | G159D | A230T | A232V | Q236H | Q245R | | |
| V68A | A98T | S103A | V104I | G159D | A232V | Q236H | Q245R | | |
| V68A | S103A | V104I | G159D | A215T | A232V | Q236H | Q245R | | |
| V68A | S103A | V104I | G159D | A232V | Q236H | Q245R | N248S | | |
| V68A | N76D | S103A | V104I | G159D | A232V | Q236H | Q245R | | |
| V68A | N76D | S103A | V104I | G159D | P210R | A232V | Q236H | Q245R | |
| V68A | N76D | S103A | V104I | G159D | A232V | Q236H | Q245R | L275V | |
| N76D | S103A | V104I | A232V | Q245R | L257V | | | | |
| V68A | S103A | V104I | G159D | A232V | Q236H | Q245R | L257V | L257H | |
| N76D | S103A | V104I | L257V | R275H | | | | | |
| V68A | S103A | V104I | G159D | T224A | A232V | Q236H | Q245R | L257V | |
| N76D | S103A | V104I | G159D | A232V | Q236H | Q245R | L257V | | |
| V68A | N76D | S103A | V104I | G159D | Y209W | A232V | Q236H | Q245R | |
| V68A | N76D | S103A | V104I | G159D | G211R | A232V | Q236H | Q245R | |
| V68A | N76D | S103A | V104I | G159D | G211V | A232V | Q236H | Q245R | |
| Q12R | V68A | N76D | S103A | V104I | G159D | Y214L | A232V | Q236H | Q245R |
| V68A | S103A | V104I | G159D | A215R | A232V | Q236H | Q245R | | |
| Q12R | V68A | S103A | V104I | G159D | A232V | Q236H | Q245R | | |
| G20R | V68A | N76D | S103A | V104I | G159D | A232V | Q236H | Q245R | S259G |
| V68A | S87R | N76D | S103A | V104I | G159D | A232V | Q236H | Q245R | T260V |
| V68A | N76D | S103A | V104I | G159D | A232V | Q236H | Q245R | N261G | |
| V68A | N76D | S103A | V104I | G159D | A232V | Q236H | Q245R | N261W | |
| N76D | S103A | V104I | A232V | Q236H | S242P | Q245R | | | |
| V68A | N76D | S103A | V104I | G159D | P210L | A232V | Q236H | Q245R | |
| Q12R | A48V | V68A | N76D | S103A | V104I | G159D | A232V | Q236H | Q245R |
| N76D | S103A | V104I | A232V | Q236H | Q245R | | | | |
| N76D | S103A | V104I | G159D | Y192F | A232V | Q236H | Q245R | | |
| N76D | S103A | V104I | V147I | G159D | A232V | Q236H | Q245R | N248S | K251R |
| Q12R | V68A | N76D | S103A | V104I | G159D | A232V | Q236H | Q245R | A272S |
| V68A | N76D | S103A | V104I | G159D | N183K | Q206L | A232V | Q236H | Q245R |
| V68A | N76D | S103A | V104I | G159D | A232V | Q236H | Q245R | S256R | |
| V68A | N76D | S103A | V104I | G159D | Q206R | A232V | Q236H | Q245R | |
| L27R | V68A | N76D | S103A | V104I | G159D | A232V | Q236H | Q245R | |
| V68A | N76D | S103A | V104I | N116T | G159D | R170S | N185S | A232V | Q236H | Q245R |
| G61E | V68A | S103A | V104I | G159D | A232V | Q236H | Q245R | N248D | N252K |
| N43D | V68A | S103A | V104I | G159D | A232V | Q236H | Q245R | N248D | N252K |
| V68A | S103A | V104I | G159D | S212P | A232V | Q236H | Q245R | N248D | N252K |
| V68A | S103A | V104I | 599N | G159D | N184D | A232V | Q236H | Q245R | N248D | N252K |

TABLE II-continued

| | | | | | | | | | | | |
|---|---|---|---|---|---|---|---|---|---|---|---|
| S103A | V104I | G159D | A232V | Q236H | Q245R | N248D | N252K | | | | |
| V68A | S103A | V104I | G159D | Y209W | A232V | Q236H | Q245R | N248D | N252K | | |
| V68A | S103A | V104I | Q109R | G159D | A232V | Q236H | Q245R | N248D | N252K | | |
| G20R | V68A | S103A | V104I | G159D | A232V | Q236H | Q245R | N248D | N252K | | |
| V68A | S103A | V104I | G159D | Y209F | A232V | Q236H | Q245R | N248D | N252K | | |
| V68A | S103A | V104I | G159D | A232V | Q236H | Q245R | N248D | N252K | N261D | | |
| V68A | S103A | V104I | G159D | N185D | A232V | Q236H | Q245R | N248D | N252K | | |
| V68A | S103A | V104I | G159D | P210R | A232V | Q236H | Q245R | N248D | N252K | | |
| V68A | S103A | V104I | G159D | P210T | A232V | Q236H | Q245R | N248D | N252K | | |
| V68A | S103A | V104I | G159D | P210S | A232V | Q236H | Q245R | N248D | N252K | | |
| V68A | S103A | V104I | G159D | N185D | P210L | A232V | Q236H | Q245R | N248D | N252K | |
| V68A | S103A | V104I | G159D | P210L | A232V | Q236H | Q245R | N248D | N252K | | |
| V68A | S103A | V104I | G159D | S212A | A232V | Q236H | Q245R | N248D | N252K | | |
| V68A | S103A | V104I | G159D | 5212G | A232V | Q236H | Q245R | N248D | N252K | | |
| V68A | S103A | V041I | G159D | 5212E | A232V | Q236H | Q245R | N248D | N252K | | |
| V68A | S103A | V104I | G159D | T213E | A232V | Q236H | Q245R | N248D | N252K | | |
| V68A | S103A | V104I | T213S | A232V | Q236H | Q245R | N248D | N252K | | | |
| V68A | A103V | V104I | G159D | T213E | A232V | Q236H | Q245R | N248D | N252K | | |
| V68A | S103A | V104I | G159D | T213R | A232V | Q236H | Q245R | N248D | N252K | | |
| V68A | S103A | V104I | G159D | T213G | A232V | Q236H | Q245R | N248D | N252K | | |
| V68A | S103A | V104I | G159D | A215V | A232V | Q236H | Q245R | N248D | N252K | | |
| V68A | S103A | V104I | G159D | A215R | A232V | Q236H | Q245R | N248D | N252K | | |
| V68A | S103A | V104I | G159D | S216T | A232V | Q236H | Q245R | N248D | N252K | | |
| V68A | S103A | V104I | G159D | S216V | A232V | Q236H | Q245R | N248D | N252K | | |
| V68A | S103A | V104I | G159D | S216C | A232V | Q236H | Q245R | N248D | N252K | | |
| G20A | V68A | S103A | V104I | G159D | A232V | Q236H | Q245R | N248D | N252K | | |
| V68A | S103A | V104I | G159D | N173D | A232V | Q236H | Q245R | N248D | N252K | | |
| V68A | S103A | V104I | G159D | A232V | Q236H | Q245R | N248D | N251V | N252K | | |
| V68A | S103A | V104I | G159D | Q206R | A232V | Q236H | Q245R | N248D | N252K | | |
| V68A | S103A | V104I | G159D | A232V | Q236H | Q245R | N248D | N252F | | | |
| V68A | S103A | V104I | G159D | A232V | Q236H | Q245R | N248D | N252L | | | |
| P55S | V68A | S103A | V104I | G159D | A232V | Q236H | Q245R | N248D | N252F | | |
| V68A | S103A | V104I | G159D | A232V | Q236H | Q245R | N248D | N252K | T255V | | |
| V68A | S103A | V104I | G159D | A232V | Q236H | Q245R | N248D | N252K | S256N | | |
| V68A | S103A | V104I | G159D | A232V | Q236H | Q245R | N248D | N252K | S256E | | |
| V68A | S103A | V104I | G159D | A232V | Q236H | Q245R | N248D | N252K | S256R | | |
| V68A | S103A | V104I | G159D | A232V | Q236H | Q245R | N248D | N252K | T260R | | |
| V68A | S103A | V104I | G159D | A232V | Q236H | Q245R | N248D | N252K | L257R | | |
| V68A | S103A | V104I | G159D | A232V | Q236H | Q245R | N248D | N252K | G258D | | |
| 18V | V68A | S103A | V104I | G159D | A232V | Q236H | Q245R | N248D | N252K | N269D | |
| V68A | S103A | V104I | N116S | G159D | A232V | Q236H | Q245R | N248D | N252K | T260E | |
| V68A | S103A | V104I | G159D | A232V | Q236H | Q245R | N248D | N252K | N261R | | |
| V68A | S103A | V104I | G159D | A232V | Q236H | Q245R | N248D | N252K | N261D | | |
| V68A | N76D | S103A | V104I | G159D | A232V | Q236H | Q245R | N248D | N252K | | |
| V68A | S103A | V104I | A232V | Q236H | Q245R | N248D | N252K | | | | |
| S103A | V104I | G159D | A232S | Q236H | Q245R | N248D | N252K | | | | |
| V68A | S103A | V104I | G159D | A232V | Q236R | Q245R | N248D | N252K | | | |
| N18S | V68A | S103A | V104I | G159D | A232V | Q236H | Q245R | N248D | N252K | | |
| V68A | S103A | V104I | G159D | A232V | Q236H | Q245V | N248D | N252K | | | |
| V68A | N76D | S101T | S103A | V104I | G159D | T213R | N218S | A232V | Q236H | Q245R | T260A |
| V68A | S103A | V104I | G159D | A228V | A232V | Q236H | Q245R | N248D | N252K | | |
| T33S | V68A | N76D | S103A | V104I | G159D | A232V | Q236H | Q245R | N248D | N252K | |
| V68A | N76D | E89D | S103A | V104I | G159D | P210L | T213R | A232V | Q236H | Q245R | T260A |
| G61E | V68A | N76D | S103A | V104I | G159D | A232V | Q236H | Q245R | N248D | N252K | |
| S103A | V104I | G591D | V205I | P210I | A232V | Q236H | Q245R | | | | |
| G61E | V68A | S103A | V104I | S130A | G159D | A232V | Q236H | Q245R | N248D | N252K | |
| G61E | V68A | S103A | V104I | A133S | Q137R | G159D | A232V | Q236H | Q245R | N248D | N252K |
| G61E | S103A | V104I | A133V | G159D | A232V | Q236H | Q245R | N248D | N252K | | |
| V68A | S103A | V104I | G159D | A232V | Q236H | Q245R | N248G | N252K | | | |
| V68A | S103A | V104I | G159D | N218S | A232V | Q236H | Q245R | N248D | N252K | | |
| G61E | V68A | S103A | V104I | G159D | S160V | A232V | Q236H | Q245R | N248D | N252K | |
| S3L | G61E | V68A | N76D | S103A | V104I | A232V | Q236H | Q245R | N248D | N252K | |
| G61E | V68A | S103A | V104I | G159D | S167F | A232V | Q236H | Q245R | N248D | N252K | |
| G97E | S103A | V104I | G159D | A232V | Q236H | Q245R | N248D | N252K | | | |
| A98D | S103A | V104I | G159D | A232V | Q236H | Q245R | N248D | N252K | | | |
| S99E | S103A | V104I | G159D | A232V | Q236H | Q245R | N248D | N252K | | | |
| S101E | S103A | V104I | G159D | A232V | Q236H | Q245R | N248D | N252K | | | |
| S101G | S103A | V104I | G159D | A232V | Q236H | Q245R | N248D | N252K | | | |
| G102A | S103A | V104I | G159D | A232V | Q236H | Q245R | N248D | N252K | | | |
| S103A | V104I | S106E | G159D | A232V | Q236H | Q245R | N248D | N252K | | | |
| S103A | V104I | Q109E | G159D | A232V | Q236H | Q245R | N248D | N252K | | | |
| S103A | V104I | G159D | A232V | Q236H | Q245R | N248D | N252K | N261R | | | |
| S103A | V104I | Q109R | G159D | A232V | Q236H | Q245R | N248D | N252K | | | |
| N62D | S103A | V104I | G159D | A232V | Q236H | Q245R | N248D | N252K | | | |
| S103A | V104I | G159D | N184D | A232V | Q236H | Q245R | N248D | N252K | | | |
| S103A | V104I | G159D | S166D | A232V | Q236H | Q245R | N248D | N252K | | | |
| S103A | V104I | G159D | L217E | A232V | Q236H | Q245R | N248D | N252K | | | |
| G20R | N62D | S103A | V104I | G159D | T213R | A232V | Q236H | Q245R | N248D | N252K | |
| N62D | S103A | V104I | G159D | T213R | A232V | Q236H | Q245R | N248D | N252K | | |

TABLE II-continued

| | | | | | | | | | | |
|---|---|---|---|---|---|---|---|---|---|---|
| S103A | V104I | G159D | Q206R | L217E | A232V | Q236H | Q245R | N248D | N252K | |
| N62D | S103A | V104I | G159D | Q206R | A232V | Q236H | Q245R | N248D | N252K | |
| S103A | V104I | S130G | G159D | A232V | Q236H | Q245R | N248D | N252K | | |
| S103A | V104I | P131V | G159D | A232V | Q236H | Q245R | N248D | N252K | | |
| K27N | S103A | V104I | G159D | A232V | Q236H | Q245R | N248D | N252K | | |
| T38G | S103A | V104I | G159D | A232V | Q236H | Q245R | N248D | N252K | | |
| T38A | N76D | S103A | V104I | G159D | T213R | A232V | Q236H | Q245R | T260A | |
| V68A | N76D | S103A | V104I | G159D | T213R | A232V | Q236H | Q245R | T260A | E271G |
| V68A | N76D | S103A | V104I | G159D | Y209W | T213R | A232V | Q236H | Q245R | T260A |
| V68A | N76D | S103A | V104I | G159D | P210I | T213R | A232V | Q236H | Q245R | T260A |
| V68A | N76D | S103A | V104I | G159D | V205I | T213R | A232V | Q236H | Q245R | T260A |
| V68A | N76D | S103A | V104I | G159D | P210I | A232V | Q236H | Q245R | T260A | |
| N76D | S103A | V104I | G159D | T213R | A232V | Q236H | Q245R | T260A | | |
| V68A | S103A | V104I | G159D | Y209W | A232V | Q236H | Q245R | | | |
| V68A | S103A | V104I | G159D | P210I | A232V | Q236H | Q245R | | | |
| V68A | S103A | V104I | G159D | A230V | A232V | Q236H | Q245R | | | |
| V68A | S103A | V104I | G159D | L126F | A232V | Q236H | Q245R | | | |
| V68A | S103A | V104I | G159D | V205I | A232V | Q236H | Q245R | | | |
| V68A | S103A | V104I | G159D | P210L | A232V | Q236H | Q245R | | | |
| S103A | V104I | G159D | A230V | Q236H | Q245R | | | | | |
| V68A | S103A | V104I | G159D | A232V | Q236H | Q245R | T260A | | | |
| S103A | V104I | G159D | A232V | Q236H | Q245R | | | | | |
| V68A | S103A | V104I | G159D | A174V | A232V | Q236H | Q245R | L257V | | |
| V68A | S103A | V104I | G159D | A194S | A232V | Q236H | Q245R | L257V | | |
| V68A | S103A | V104I | G159D | Y209W | A232V | Q236H | Q245R | L257V | | |
| S103A | V104I | G159D | G232V | Q236H | Q245R | L257V | | | | |
| V68A | N76D | S103A | V104I | G159D | T213R | A232V | Q245R | T260A | N261W | |
| V68A | S103A | V104I | G159D | A232V | Q236H | Q245R | L257V | N261W | | |
| S103A | V104I | G159D | G213R | A232V | Q236H | Q245R | T260A | | | |
| S103A | V104I | G159D | P210I | A232V | Q236H | Q245R | N248D | N252K | | |
| S103A | V104I | G159D | Y209W | A232V | Q236H | Q245R | L257V | | | |
| V68A | N76D | S103A | V104I | G159D | P210L | T213R | A232V | Q236H | Q245R | T260A |
| Q12R | S103A | V104S | G159D | Y209W | T213R | A232V | Q236H | Q245R | T260A | |
| S103A | V104I | Y209W | A232V | Q236H | Q245R | L257V | | | | |
| S103A | V104I | G159D | V205I | P210I | T213R | A232V | Q236H | Q245R | T260A | |
| S103A | V104I | G159D | V205I | Y209W | A232V | Q236H | Q245R | T260A | | |
| V68A | S103A | V104I | G159D | V205I | Y209W | P210I | A232V | Q236H | Q245R | |
| S103A | V104I | G159D | V205I | Y209W | P210I | A232V | Q236H | Q245R | L257V | |
| S103A | V104I | G159D | V205I | Y209W | A232V | Q236H | Q245R | L257V | | |
| V68A | S103A | V104I | G159D | V205I | Y209W | P210I | A232V | Q236H | Q245R | T260A |
| S103A | V104I | G159D | V205I | Y209W | P210I | A232V | Q236H | Q245R | | |
| S103A | V104I | G159D | Y209W | P210I | A232V | Q236H | Q245R | | | |
| S103A | V104I | G159D | V205I | P210I | A232V | Q236H | Q245R | | | |
| V68A | S103A | V104I | S128L | G159D | A232V | Q236H | Q245R | | | |
| A48V | S103A | V104I | G159D | A230V | Q236H | Q245R | | | | |
| A48V | V68A | S103A | V104I | G159D | Y209W | A232V | Q236H | Q245R | | |
| A48V | V68A | S103A | V104I | G159D | A232V | Q236H | Q245R | N248D | N252K | |
| A48V | V68A | S103A | V104I | G159D | A232V | Q236H | Q245R | L257V | N261W | |
| G102A | S103A | V104I | G159D | S212G | A232V | Q236H | Q245R | N248D | N252K | |
| Q12R | G102A | S103A | V104I | G159D | S212G | A232V | Q236H | Q245R | N248D | N252K |
| S101G | G102A | S103A | V104I | G159D | S212G | A232V | Q236H | Q245R | N248D | N252K |
| A98L | G102A | S103A | V104I | G159D | S212G | A232V | Q236H | Q245R | N248D | N252K |
| G102A | S103A | V104I | G159D | T213R | A232V | Q236H | Q245R | N248D | N252K | |
| S103A | V104I | P131V | G159D | A232V | Q236H | Q245R | N248D | N252K | | |
| S103A | V104I | G159D | N184S | A232V | Q236H | Q245R | N248D | N252K | | |
| S103A | V104I | G159D | N184G | A232V | Q236H | Q245R | N248D | N252K | | |
| S103A | V104I | G159D | A232V | Q236H | V244T | Q245R | N248D | N252K | | |
| S103A | V104I | G159D | A232V | Q236H | V244A | Q245R | N248D | N252K | | |
| N62D | S103A | V104I | G159D | T213R | A232V | Q236H | Q245R | N248D | N252K | S256R |
| Q12R | N62D | S103A | V104I | G159D | T213R | A232V | Q236H | Q245R | N248D | N252K |
| S101G | S103A | V104I | G159D | N185D | A232V | Q236H | Q245R | N248D | N252K | |
| S101G | S103A | V104I | G159D | Q206E | A232V | Q236H | Q245R | N248D | N252K | |
| S101G | S103A | V104I | G159D | T213Q | A232V | Q236H | Q245R | N248D | N252K | |
| A98L | G102A | S103A | V104I | G159D | A232V | Q236H | Q245R | N248D | N252K | |
| S101G | G102A | S103A | V104I | G159D | A232V | Q236H | Q245R | N248D | N252K | |
| A98L | G102A | S103A | V104I | G159D | S212G | A232V | Q236H | Q245R | N248D | N252K |
| A98L | G102A | S103A | V104I | G159D | S212G | A232V | Q236H | Q245R | N248D | N252K |
| N62D | S103A | V104I | Q109R | G159D | T213R | A232V | Q236H | Q245R | N248D | N252K |
| N62D | S103A | V104I | G159D | S212G | T213R | A232V | Q236H | Q245R | N248D | N252K |
| N62D | S101G | S103A | V104I | G159D | S212G | T213R | A232V | Q236H | Q245R | N248D | N252K |
| S103A | V104I | G159D | A232V | Q245R | N248D | N252K | | | | |
| S103A | V104I | G159D | A230V | Q245R | | | | | | |
| N62D | S103A | VJ04I | S130G | G159D | T213R | A232V | Q236H | Q245R | N248D | N252K |
| S101G | S103A | V104I | S130G | G159D | A232V | Q236H | Q245R | N248D | N252K | |
| S101G | S103A | VJ04I | S128G | G159D | A232V | Q236H | Q245R | N248D | N252K | |
| S101G | S103A | V104I | S128L | G159D | A232V | Q236H | Q245R | N248D | N252K | |
| N62D | S101G | S103A | V104I | G159D | T213R | A232V | Q236H | Q245R | N248D | N252K |
| N62D | S103A | V104I | S128G | G159D | T213R | A232V | Q236H | Q245R | N248D | N252K |

TABLE II-continued

| | | | | | | | | | |
|---|---|---|---|---|---|---|---|---|---|
| N62D | S103A | V104I | S128L | G159D | T213R | A232V | Q236H | Q245R | N248D | N252K |
| S101G | S103A | V104I | G159D | A232V | Q236H | Q245R | N248D | N252K | T260A |
| S101G | S103A | V104I | P131V | G159D | A232V | Q236H | Q245R | N248D | N252K |
| A98V | S101G | S103A | V104I | G159D | A232V | Q236H | Q245R | N248D | N252K |
| S99G | S101G | S103A | V104I | G159D | A232V | Q236H | Q245R | N248D | N252K |
| S101G | S103A | V104I | G159D | S212G | A232V | Q236H | Q245R | N248D | N252K |
| S101G | S103A | V104I | G159D | Y209W | A232V | Q236H | Q245R | N248D | N252K |
| S101G | S103A | V104I | G159D | P210I | A232V | Q236H | Q245R | N248D | N252K |
| S101G | S103A | V104I | G159D | V205I | A232V | Q236H | Q245R | N248D | N252K |
| S101G | S103A | V104I | G159D | A230V | Q236H | Q245R | | | |
| S101G | S103A | V104I | G159D | A194P | A232V | Q236H | Q245R | N248D | N252K |
| N76D | S101G | S103A | VJ04I | G159D | A194P | A232V | Q236H | Q245R | N248D | N252K |
| S101G | S103A | V104I | G159D | A230V | A232V | Q236H | Q245R | N248D | N252K |
| N62D | S103A | V104I | G159D | N185D | Q206E | T213R | A232V | Q236H | Q245R | N248D | N252K | E271Q |

Still yet an even more preferred protease variant useful in the cleaning composition of the present invention include a substitution set selected from the group consisting of the substitution sets in Table I except for the following substitution sets of

TABLE III

| | | | | | | | | | |
|---|---|---|---|---|---|---|---|---|---|
| 76 | 103 | 104 | 259 | | | | | | |
| 76 | 86 | 103 | 104 | | | | | | |
| 76 | 103 | 104 | 130 | | | | | | |
| 76 | 99 | 103 | 104 | 204 | | | | | |
| 76 | 103 | 104 | 242 | | | | | | |
| 76 | 103 | 104 | 104 | 182 | 198 | | | | |
| 21 | 76 | 103 | 104 | 182 | | | | | |
| 76 | 103 | 104 | 119 | 137 | | | | | |
| 76 | 103 | 104 | 173 | 222 | | | | | |
| 61 | 76 | 103 | 104 | 222 | | | | | |
| 68 | 76 | 103 | 104 | 116 | 159 | 170 | 185 | 232 | 236 | 245 |

Still yet an even more preferred protease variant useful in the cleaning composition of the present invention include a substitution set selected from the group consisting of the substitution sets in Table IV:

TABLE IV

| | | | | | | | | | |
|---|---|---|---|---|---|---|---|---|---|
| 76 | 103 | 104 | 222 | 245 | | | | | |
| 76 | 103 | 104 | 222 | 249 | | | | | |
| 68 | 103 | 104 | 159 | 232 | 236 | 245 | 252 | | |
| 68 | 76 | 103 | 104 | 159 | 213 | 232 | 236 | 245 | 260 |
| 22 | 68 | 76 | 103 | 104 | | | | | |
| 68 | 103 | 104 | 159 | 232 | 236 | 245 | 248 | 252 | |
| 68 | 103 | 104 | 159 | 232 | 236 | 245 | | | |
| 68 | 103 | 104 | 140 | 159 | 232 | 236 | 245 | 252 | |
| 43 | 68 | 103 | 104 | 159 | 232 | 236 | 245 | 252 | |
| 43 | 68 | 103 | 104 | 159 | 232 | 236 | 245 | | |
| 12 | 76 | 103 | 104 | 130 | 222 | 245 | 261 | | |
| 76 | 103 | 104 | 130 | 222 | 245 | | | | |
| 68 | 103 | 104 | 159 | 232 | 236 | 245 | 257 | | |
| 68 | 76 | 103 | 104 | 159 | 210 | 232 | 236 | 245 | |
| 68 | 103 | 104 | 159 | 224 | 232 | 236 | 245 | 257 | |
| 76 | 103 | 104 | 159 | 232 | 236 | 245 | 257 | | |
| 68 | 76 | 103 | 104 | 159 | 211 | 232 | 236 | 245 | |
| 12 | 68 | 76 | 103 | 104 | 159 | 214 | 232 | 236 | 245 |
| 68 | 76 | 103 | 104 | 159 | 215 | 232 | 236 | 245 | |
| 12 | 68 | 76 | 103 | 104 | 159 | 232 | 236 | 245 | |
| 20 | 68 | 76 | 103 | 104 | 159 | 232 | 236 | 245 | 259 |
| 68 | 76 | 87 | 103 | 104 | 159 | 232 | 236 | 245 | 260 |
| 68 | 76 | 103 | 104 | 159 | 232 | 236 | 245 | 261 | |
| 12 | 48 | 68 | 76 | 103 | 104 | 159 | 232 | 236 | 245 |
| 76 | 103 | 104 | 159 | 192 | 232 | 236 | 245 | | |
| 76 | 103 | 104 | 147 | 159 | 232 | 236 | 245 | 248 | 251 |
| 12 | 68 | 76 | 103 | 104 | 159 | 232 | 236 | 245 | 272 |
| 68 | 76 | 103 | 104 | 159 | 183 | 206 | 232 | 236 | 245 |
| 68 | 76 | 103 | 104 | 159 | 232 | 236 | 245 | 256 | |
| 68 | 76 | 103 | 104 | 159 | 206 | 232 | 236 | 245 | |
| 27 | 68 | 76 | 103 | 104 | 159 | 232 | 236 | 245 | |

TABLE IV-continued

| | | | | | | | | | | |
|---|---|---|---|---|---|---|---|---|---|---|
| 68 | 103 | 104 | 159 | 212 | 232 | 236 | 245 | 248 | 252 | |
| 103 | 104 | 159 | 232 | 236 | 245 | 248 | 252 | | | |
| 68 | 103 | 104 | 159 | 209 | 232 | 236 | 245 | 248 | 252 | |
| 68 | 103 | 104 | 109 | 159 | 232 | 236 | 245 | 248 | 252 | |
| 20 | 68 | 103 | 104 | 159 | 232 | 236 | 245 | 248 | 252 | |
| 68 | 103 | 104 | 159 | 209 | 232 | 236 | 245 | 248 | 252 | |
| 68 | 103 | 104 | 159 | 210 | 232 | 236 | 245 | 248 | 252 | |
| 68 | 103 | 104 | 159 | 212 | 232 | 236 | 245 | 248 | 252 | |
| 68 | 103 | 104 | 159 | 213 | 232 | 236 | 245 | 248 | 252 | |
| 68 | 103 | 104 | 213 | 232 | 236 | 245 | 248 | 252 | | |
| 68 | 103 | 104 | 159 | 215 | 232 | 236 | 245 | 248 | 252 | |
| 68 | 103 | 104 | 159 | 216 | 232 | 236 | 245 | 248 | 252 | |
| 20 | 68 | 103 | 104 | 159 | 232 | 236 | 245 | 248 | 252 | |
| 68 | 103 | 104 | 159 | 232 | 236 | 245 | 248 | 252 | 255 | |
| 68 | 103 | 104 | 159 | 232 | 236 | 245 | 248 | 252 | 256 | |
| 68 | 103 | 104 | 159 | 232 | 236 | 245 | 248 | 252 | 260 | |
| 68 | 103 | 104 | 159 | 228 | 232 | 236 | 245 | 248 | 252 | |
| 68 | 76 | 89 | 103 | 104 | 159 | 210 | 213 | 232 | 236 | 245 | 260 |
| 68 | 103 | 104 | 159 | 218 | 232 | 236 | 245 | 248 | 252 | |

Still yet an even more preferred protease variant useful in the cleaning composition of the present invention include a substitution set selected from the group consisting of the substitution sets in Table V:

TABLE V

| | | | | | | | | | | |
|---|---|---|---|---|---|---|---|---|---|---|
| V68A | S103A | V104I | G159D | A228V | A232V | Q236H | Q245R | N248D | N252K | |
| V68A | S103A | V104I | G159D | N218S | A232V | Q236H | Q245R | N248D | N252K | |
| G20R | V68A | S103A | V104I | G159D | A232V | Q236H | Q245R | N248D | N252K | |
| V68A | N76D | E89D | S103A | V104I | G159D | P210L | T213R | A232V | Q236H | Q245R | T260A |
| V68A | S103A | V104I | G159D | A232V | Q236H | Q245R | N248D | N252K | S256R | |
| V68A | S103A | V104I | G159D | A232V | Q236H | Q245R | N248D | N252K | T260R | |
| V68A | S103A | V104I | G159D | A232V | Q236H | Q245R | N248D | N252K | T255V | |
| V68A | S103A | V104I | G159D | A232V | Q236H | Q245R | N248D | N252K | S256N | |
| V68A | S103A | V104I | G159D | A232V | Q236H | Q245R | N248D | N252L | | |
| V68A | S103A | V104I | G159D | T213R | A232V | Q236H | Q245R | N248D | N252K | |
| V68A | S103A | V104I | G159D | A215V | A232V | Q236H | Q245R | N248D | N252K | |
| V68A | S103A | V104I | G159D | A215R | A232V | Q236H | Q245R | N248D | N252K | |
| V68A | S103A | V104I | G159D | S216T | A232V | Q236H | Q245R | N248D | N252K | |
| V68A | S103A | V104I | G159D | S216V | A232V | Q236H | Q245R | N248D | N252K | |
| V68A | S103A | V104I | T213S | A232V | Q236H | Q245R | N248D | N252K | | |
| V68A | S103A | V104I | G159D | P210L | A232V | Q236H | Q245R | N248D | N252K | |
| V68A | S103A | V104I | G159D | S212C | A232V | Q236H | Q245R | N248D | N252K | |
| V68A | S103A | V104I | G159D | S212G | A232V | Q236H | Q245R | N248D | N252K | |
| S103A | V104I | G159D | A232V | Q236H | Q245R | N248D | N252K | | | |
| V68A | S103A | V104I | G159D | Y209W | A232V | Q236H | Q245R | N248D | N252K | |
| V68A | S103A | V104I | Q109R | G159D | A232V | Q236H | Q245R | N248D | N252K | |
| G20R | V68A | S103A | V104I | G159D | A232V | Q236H | Q245R | N248D | N252K | |
| V68A | S103A | V104I | G159D | Y209F | A232V | Q236H | Q245R | N248D | N252K | |
| Q12R | N76D | S103A | I104T | S130T | M222S | Q245R | N261D | | | |
| N76D | S103A | I104T | S130T | M222S | Q245R | | | | | |
| N76D | S103A | V104I | M222S | H249R | | | | | | |
| N76D | S103A | V104I | M222S | Q245R | | | | | | |
| N76D | S103A | V104I | G159D | Y192F | A232V | Q236H | Q245R | | | |
| N76D | S103A | V104I | V147I | G159D | A232V | Q236H | Q245R | N248S | K251R | |
| Q12R | V68A | N76D | S103A | V104I | G159D | A232V | Q236H | Q245R | A272S | |
| V68A | N76D | S103A | V104I | G159D | N183K | Q206L | A232V | Q236H | Q245R | |
| V68A | N76D | S103A | V104I | G159D | A232V | Q236H | Q245R | S256R | | |
| V68A | N76D | S103A | V104I | G159D | Q206R | A232V | Q236H | Q245R | | |
| K27R | V68A | N76D | S103A | V104I | G159D | A232V | Q236H | Q245R | | |
| Q12R | A48V | V68A | N76D | S103A | V104I | G159D | A232V | Q236H | Q245R | |
| V68A | N76D | S103A | V104I | G159D | A232V | Q236H | Q245R | N261W | | |
| V68A | N76D | S103A | V104I | G159D | G211R | A232V | Q236H | Q245R | | |
| V68A | N76D | S103A | V104I | G159D | G211V | A232V | Q236H | Q245R | | |
| Q12R | V68A | N76D | S103A | V104I | G159D | Y214L | A232V | Q236H | Q245R | |
| V68A | N76D | S103A | V104I | G159D | A215R | A232V | Q236H | Q245R | | |
| Q12R | V68A | N76D | S103A | V104I | G159D | A232V | Q236H | Q245R | | |
| G20R | V68A | N76D | S103A | V104I | G159D | A232V | Q236H | Q245R | S259G | |
| V68A | N76D | S87R | S103A | V104I | G159D | A232V | Q236H | Q245R | T260V | |
| N76D | S103A | V104I | G159D | A232V | Q236H | Q245R | L257V | | | |
| V68A | N76D | S103A | V104I | G159D | T213R | A232V | Q236H | Q245R | T260A | |
| T22K | V68A | N76D | S103A | V104I | | | | | | |
| V68A | N76D | S103A | V104I | G159D | P210R | A232V | Q236H | Q245R | | |
| V68A | S103A | V104I | G159D | S212P | A232V | Q236H | Q245R | N248D | N252K | |
| V68A | S103A | V104I | G159D | T224A | A232V | Q236H | Q245R | L257V | | |
| V68A | S103A | V104I | G159D | A232V | Q236H | Q245R | N252S | | | |

TABLE V-continued

| | | | | | | | | |
|---|---|---|---|---|---|---|---|---|
| V68A | S103A | V104I | G159D | A232V | Q236H | Q245R | N252K | |
| V68A | S103A | V104I | G159D | A232V | Q236H | Q245R | N248D | N252K |
| V68A | S103A | V104I | G159D | A232V | Q236H | Q245R | | |
| V68A | S103A | V104I | N140D | G159D | A232V | Q236H | Q245R | N252K |
| N43S | V68A | S103A | V104I | G159D | A232V | Q236H | Q245R | N252K |
| N43K | V68A | S103A | V104I | G159D | A232V | Q236H | Q245R | |
| N43D | V68A | S103A | V104I | G159D | A232V | Q236H | Q245R | N252K |
| V68A | S103A | V104I | G159D | A232V | Q236H | Q245R | L257V | |

A highly preferred protease variant useful in the cleaning compositions of the present invention include a substitution set selected from the group consisting of:

12/102/103/104/159/212/232/236/245/248/252; 12/76/103/104/130/170/185/222/243/245;

12/76/103/104/130/222/245/261; 12/76/103/104/130/222/245;

12/76/103/104/222/245;

61/68/103/104/159/232/236/245/248/252; 62/103/104/159/213/232/236/245/248/252;

62/103/104/109/159/213/232/236/245/248/252; 62/103/104/159/232/236/245/248/252;

62/101/103/104/159/212/213/232/236/245/248/252;

62/103/104/130/159/213/232/236/245/248/252; 68/103/104/159/232/236/245/248/252/270;

68/103/104/159/185/232/236/245/248/252; 68/103/104/159/210/232/236/245/248/252;

68/103/104/159/185/210/232/236/245/248/252; 68/103/104/159/213/232/236/245/248/252;

68/103/104/159/230/232/236/245; 68/76/103/104/159/209/232/236/245;

68/103/104/232/236/245/248/257/275; 68/103/104/213/232/236/245/248/252;

68/103/104/159/232/236/245/248/252; 68/103/104/159/209/232/236/245;

68/76/103/104/159/236; 68/76/103/104/159/236/245;

68/76/103/104/159/232/236/245; 68/103/104/159/232/236/245/252;

68/103/104/159/232/236/245; 68/103/104/159/232/236/245/257;

68/76/103/104/159/211/232/236/245; 68/76/103/104/159/215/232/236/245;

68/103/104/159/210/232/236/245; 68/103/104/159/213/232/236/245/260;

68/76/103/104/159/213/232/236/245/260; 68/103/104/159/236;

68/76/103/104/159/210/232/236/245/260; 68/103/104/159/236/245;

68/103/104/159/183/232/236/245/248/252; 68/76/103/104/159/236/245;

68/103/104/232/236/245/257/275; 68/103/104/159/213/232/236/245;

76/103/222/245; 76/103/104/222/245;

76/103/104/159/232/236/245;

76/103/104/159/213/232/236/245/260; 76/103/104/159;

76/103/104/131/159/232/236/245/248/252; 97/103/104/159/232/236/245/248/252;

98/102/103/104/159/212/232/236/245/248/252; 98/103/104/159/232/236/245/248/252;

101/103/104/159/232/236/245/248/252; 102/103/104/159/232/236/245/248/252;

103/104/159/232/236/245; 103/104/159/232/236/245/248/252;

103/104/159/205/209/232/236/245/257 103/104/159/232/245/248/252;

103/104/159/205/209/210/232/236/245/257; 103/104/159/213/232/236/245/248/252;

103/104/159/217/232/236/245/248/252; 103/104/130/159/232/236/245/248/252;

103/104/159/230/236/245; 103/104/159/236/245;

103/104/159/248/252/270; 103/104/131/159/232/236/245/248/252;

103/104/159/205/209/232/236/245; and 103/104/159/232/236/245/257.

A more highly preferred protease variant useful in the cleaning compositions of the present invention include a substitution set selected from the group consisting of:

12R/76D/103A/104T/130T/222S/245R;

12R/76D/103A/104I/222S/245R;

12R/102A/103A/104I/159D/212G/232V/236H/245R/248D/252K;

12R/76D/103A/104T/130G/222S/245R/261D;

12R/76D/103A/104T/30G/170S/185D/222S/243D/245R;

61E/68A/103A/104I/159D/232V/236H/245R/248D/252K;

62D/103A/104I/109R/159D/213R/232V/236H/245R/248D/252K;

62D/103A/104I/159D/213R/232V/236H/245R/248D/252K;

62D/103A/104I/159D/232V/236H/245R/248D/252K;

62D/103A/104I/130G/159D/213R/232V/236H/245R/248D/252K;

62D/101G/103A/104I/159D/212G/213R/232V/236H/245R/248D/252K;

68A/103A/104I/159D/232V/236H/245R/248D/252K/270A;

68A/76D/103A/104I/159D/213R/232V/236H/245R/260A;

68A/103A/104I/159D/236H;

68A/103A/104I/159D/236H/245R;

68A/76D/103A/104I/159D/210I/232V/236H/245R/260A;

68A/103A/104I/159D/183D/232V/236H/245R/248D/252K;

68A/103A/104I/159D/209W/232V/236H/245R;

68A/76D/103A/104I/159D/211R/232V/236H/245R;

68A/76D/103A/104I/159D/215R/232V/236H/245R;

68A/103A/104I/159D/213R/232V/236H/245R/260A;

68A/76D/103A/104I/159D/236H;

68A/76D/103A/104I/159D/236H/245R;

68A/76D/103A/104I/159D/232V/236H/245R;

68A/103A/104I/159D/232V/236H/245R/252K;
68A/103A/104I/159D/232V/236H/245R;
68A/103A/104I/159D/232V/236H/245R/257V;
68A/103A/104I/159D/185D/232V/236H/245R/248D/252K;
68A/103A/104I/159D/210L/232V/236H/245R/248D/252K;
68A/103A/104I/159D/185D/210L/232V/236H/245R/248D/252K;
68A/103A/104I/159D/213E/232V/236H/245R/248D/252K;
68A/103A/104I/159D/230V/232V/236H/245R;
68A/76D/103A/104I/159D/209W/232V/236H/245R;
68A/103A/104I/232V/236H/245R/248D/257V/275H;
68A/103A/104I/232V/236H/245R/257V/275H;
68A/103A/104I/213E/232V/236H/245R/248D/252K;
68A/103A/104I/159D/232V/236H/245R/248D/252K;
68A/103A/104I/159D/210I/232V/236H/245R;
68A/103A/104I/159D/210L/232V/236H/245R;
68A/103A/104I/159D/213G/232V/236H/245R;
76D/103A/222S/245R;
76D/103A/104I/222S/245R;
76D/103A/104I/159D/232V/236H/245R;
76D/103A/104I/159D;
76D/103A/104I/131V/159D/232V/236H/245R/248D/252K;
76D/103A/104I/159D/213R/232V/236H/245R/260A;
97E/103A/104I/159D/232V/236H/245R/248D/252K;
98L/103A/104I/159D/232V/236H/245R/248D/252K;
98L/102A/103A/104I/159D/212G/232V/236H/245R/248D/252K;
101G/103A/104I/159D/232V/236H/245R/248D/252K;
102A/103A/104I/159D/232V/236H/245R/248D/252K;
103A/104I/159D/232V/236H/245R/248D/252K;
103A/104I/159D/213R/232V/236H/245R/248D/252K;
103A/104I/130G/159D/232V/236H/245R/248D/252K;
103A/104I/159D/230V/236H/245R;
103A/104I/159D/217E/232V/236H/245R/248D/252K;
103A/104I/159D/236H/245R;
103A/104I/159D/248D/252K/270V;
103A/104I/159D/232V/236H/245R;
103A/104I/159D/205I/209W/232V/236H/245R;
103A/104I/159D/232V/236H/245R/257V;
103A/104I/159D/205I/209W/232V/236H/245R/257V;
103A/104I/131V/159D/232V/236H/245R/248D/252K;
103A/104I/159D/205I/209W/210I/232V/236H/245R/257V; and
103A/104I/159D/232V/245R/248D/252K.

An even more highly preferred protease variant useful in the cleaning compositions of the present invention include a substitution set selected from the group consisting of:
12/76/103/104/130/222/245/261;
62/103/104/159/232/236/245/248/252;
62/103/104/159/213/232/236/245/248/252;
62/101/103/104/159/212/213/232/236/245/248/252;
68/103/104/159/232/236/245;
68/103/104/159/230/232/236/245;
68/103/104/159/209/232/236/245;
68/103/104/159/232/236/245/257;
68/76/103/104/159/213/232/236/245/260;
68/103/104/159/213/232/236/245/248/252;
68/103/104/159/183/232/236/245/248/252;
68/103/104/159/185/232/236/245/248/252;
68/103/104/159/185/210/232/236/245/248/252;
68/103/104/159/210/232/236/245/248/252;
68/103/104/159/213/232/236/245;
98/103/104/159/232/236/245/248/252;
98/102/103/104/159/212/232/236/245/248/252;
101/103/104/159/232/236/245/248/252;
102/103/104/159/232/236/245/248/252;
103/104/159/230/236/245;
103/104/159/232/236/245/248/252;
103/104/159/217/232/236/245/248/252;
103/104/130/159/232/236/245/248/252;
103/104/131/159/232/236/245/248/252;
103/104/159/213/232/236/245/248/252; and
103/104/159/232/236/245.

The most highly preferred protease variant useful in the cleaning compositions of the present invention include a substitution set selected from the group consisting of:
12R/76D/103A/104T/130T/222S/245R/261D;
62D/103A/104I/159D/232V/236H/245R/248D/252K;
62D/103A/104I/159D/213R/232V/236H/245R/248D/252K;
68A/103A/104I/159D/209W/232V/236H/245R;
68A/76D/103A/104I/159D/213R/232V/236H/245R/260A;
68A/103A/104I/159D/213E/232V/236H/245R/248D/252K;
68A/103A/104I/159D/183D/232V/236H/245R/248D/252K;
68A/103A/104I/159D/232V/236H/245R;
68A/103A/104I/159D/230V/232V/236H/245R;
68A/103A/104I/159D/232V/236H/245R/257V;
68A/103A/104I/159D/213G/232V/236H/245R/248D/252K;
68A/103A/104I/159D/185D/232V/236H/245R/248D/252K;
68A/103A/104I/159D/185D/210L/232V/236H/245R/248D/252K;
68A/103A/104I/159D/210L/232V/236H/245R/248D/252K;
68A/103A/104I/159D/213G/232V/236H/245R;
98L/103A/104I/159D/232V/236H/245R/248D/252K;
98L/102A/103A/104I/159D/212G/232V/236H/245R/248D/252K;
101G/103A/104I/159D/232V/236H/245R/248D/252K;
102A/103A/104I/159D/232V/236H/245R/248D/252K;
103A/104I/159D/230V/236H/245R;
103A/104I/159D/232V/236H/245R/248 D/252K;
103A/104I/159D/217E/232V/236H/245R/248D/252K;
103A/104I/130G/159D/232V/236H/245R/248D/252K;
103A/104I/131V/159D/232V/236H/245R/248D/252K;
103A/104I/159D/213R/232V/236H/245R/248D/252K; and
103A/104I/159D/232V/236H/245R.

In another preferred embodiment, the protease variants which are the protease enzymes useful in the cleaning compositions of the present invention comprise protease variants including a substitution of an amino acid residue with another naturally occurring amino acid residue at one or more amino acid residue positions corresponding to positions 62, 212, 230, 232, 252 and 257 of *Bacillus amyloliquefaciens* subtilisin.

While any combination of the above listed amino acid substitutions may be employed, the preferred protease variant enzymes useful for the present invention comprise the substitution, deletion or insertion of amino acid residues in the following combinations:

(1) a protease variant including substitutions of the amino acid residues at position 62 and at one or more of the following positions 103, 104, 109, 159, 213, 232, 236, 245, 248 and 252;

(2) a protease variant including substitutions of the amino acid residues at position 212 and at one or more of the following positions 12, 98, 102, 103, 104, 159, 232, 236, 245, 248 and 252;

(3) a protease variant including substitutions of the amino acid residues at position 230 and at one or more of the following positions 68, 103, 104, 159, 232, 236 and 245;

(4) a protease variant including substitutions of the amino acid residues at position 232 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(5) a protease variant including substitutions of the amino acid residues at position 232 and at one or more of the following positions 103, 104, 236 and 245;

(6) a protease variant including substitutions of the amino acid residues at position 232 and 103 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(7) a protease variant including substitutions of the amino acid residues at position 232 and 104 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(8) a protease variant including substitutions of the amino acid residues at position 232 and 236 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(9) a protease variant including substitutions of the amino acid residues at position 232 and 245 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(10) a protease variant including substitutions of the amino acid residues at position 232, 103, 104, 236 and 245 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;

(11) a protease variant including substitutions of the amino acid residues at position 252 and at one or more of the following positions 12, 61, 62, 68, 97, 98, 101, 102, 103, 104, 109, 130, 131, 159, 183, 185, 210, 212, 213, 217, 232, 236, 245, 248 and 270;

(12) a protease variant including substitutions of the amino acid residues at position 252 and at one or more of the following positions 103, 104, 236 and 245;

(13) a protease variant including substitutions of the amino acid residues at positions 252 and 103 and at one or more of the following positions 12, 61, 62, 68, 97, 98, 101, 102, 103, 104, 109, 130, 131, 159, 183, 185, 210, 212, 213, 217, 232, 236, 245, 248 and 270;

(14) a protease variant including substitutions of the amino acid residues at positions 252 and 104 and at one or more of the following positions 12, 61, 62, 68, 97, 98, 101, 102, 103, 104, 109, 130, 131, 159, 183, 185, 210, 212, 213, 217, 232, 236, 245, 248 and 270;

(15) a protease variant including substitutions of the amino acid residues at positions 252 and 236 and at one or more of the following positions 12, 61, 62, 68, 97, 98, 101, 102, 103, 104, 109, 130, 131, 159, 183, 185, 210, 212, 213, 217, 232, 236, 245, 248 and 270;

(16) a protease variant including substitutions of the amino acid residues at positions 252 and 245 and at one or more of the following positions 12, 61, 62, 68, 97, 98, 101, 102, 103, 104, 109, 130, 131, 159, 183, 185, 210, 212, 213, 217, 232, 236, 245, 248 and 270;

(17) a protease variant including substitutions of the amino acid residues at positions 252, 103, 104, 236 and 245 and at one or more of the following positions 12, 61, 62, 68, 97, 98, 101, 102, 103, 104, 109, 130, 131, 159, 183, 185, 210, 212, 213, 217, 232, 236, 245, 248 and 270; and

(18) a protease variant including substitutions of the amino acid residues at position 257 and at one or more of the following positions 68, 103, 104, 205, 209, 210, 232, 236, 245 and 275.

A more preferred protease variant useful in the cleaning compositions of the present invention include a substitution set (one substitution set per row in the following Table VI) selected from the group consisting of:

TABLE VI

| | | | | | | | | |
|---|---|---|---|---|---|---|---|---|
| 76 | 103 | 104 | 212 | 271 | | | | |
| 76 | 103 | 104 | 252 | 261 | | | | |
| 76 | 103 | 104 | 212 | 258 | | | | |
| 4 | 76 | 103 | 104 | 159 | 217 | 252 | | |
| 12 | 62 | 76 | 103 | 104 | 159 | | | |
| 76 | 103 | 104 | 212 | 268 | 271 | | | |
| 76 | 87 | 103 | 104 | 212 | 271 | | | |
| 76 | 103 | 104 | 212 | 245 | 271 | | | |
| 76 | 103 | 104 | 134 | 141 | 212 | 271 | | |
| 76 | 103 | 104 | 212 | 236 | 243 | 271 | | |
| 20 | 62 | 76 | 103 | 104 | | | | |
| 68 | 76 | 103 | 104 | 159 | 232 | 236 | 245 | |
| 76 | 103 | 104 | 232 | 245 | | | | |
| 24 | 68 | 76 | 103 | 104 | 159 | 232 | 236 | 245 |
| 68 | 103 | 104 | 159 | 232 | 236 | 245 | 252 | |
| 68 | 76 | 103 | 104 | 159 | 213 | 232 | 236 | 245 | 260 |
| 68 | 103 | 104 | 159 | 232 | 236 | 245 | 248 | 252 |
| 68 | 103 | 104 | 159 | 232 | 236 | 245 | | |

TABLE VI-continued

| | | | | | | | | | |
|---|---|---|---|---|---|---|---|---|---|
| 68 | 103 | 104 | 140 | 159 | 232 | 236 | 245 | 252 | |
| 43 | 68 | 103 | 104 | 159 | 232 | 236 | 245 | 252 | |
| 43 | 68 | 103 | 104 | 159 | 232 | 236 | 245 | | |
| 43 | 68 | 103 | 104 | 159 | 232 | 236 | 245 | 252 | |
| 68 | 87 | 103 | 104 | 159 | 232 | 236 | 245 | 252 | 275 |
| 68 | 103 | 104 | 159 | 232 | 236 | 245 | 257 | | |
| 68 | 103 | 104 | 116 | 159 | 232 | 236 | 245 | | |
| 68 | 103 | 104 | 159 | 232 | 236 | 245 | 248 | | |
| 10 | 68 | 103 | 104 | 159 | 232 | 236 | 245 | | |
| 68 | 103 | 104 | 159 | 203 | 232 | 236 | 245 | | |
| 68 | 103 | 104 | 159 | 232 | 236 | 237 | 245 | | |
| 68 | 76 | 79 | 103 | 104 | 159 | 232 | 236 | 245 | |
| 68 | 103 | 104 | 159 | 183 | 232 | 236 | 245 | | |
| 68 | 103 | 104 | 159 | 174 | 206 | 232 | 236 | 245 | |
| 68 | 103 | 104 | 159 | 188 | 232 | 236 | 245 | | |
| 68 | 103 | 104 | 159 | 230 | 232 | 236 | 245 | | |
| 68 | 98 | 103 | 104 | 159 | 232 | 236 | 245 | | |
| 68 | 103 | 104 | 159 | 215 | 232 | 236 | 245 | | |
| 68 | 103 | 104 | 159 | 232 | 236 | 245 | 248 | | |
| 68 | 76 | 103 | 104 | 159 | 232 | 236 | 245 | | |
| 68 | 76 | 103 | 104 | 159 | 210 | 232 | 236 | 245 | |
| 68 | 76 | 103 | 104 | 159 | 232 | 236 | 245 | 257 | |
| 76 | 103 | 104 | 232 | 236 | 245 | 257 | | | |
| 68 | 103 | 104 | 159 | 232 | 236 | 245 | 257 | 275 | |
| 76 | 103 | 104 | 257 | 275 | | | | | |
| 68 | 103 | 104 | 159 | 224 | 232 | 236 | 245 | 257 | |
| 76 | 103 | 104 | 159 | 232 | 236 | 245 | 257 | | |
| 68 | 76 | 103 | 104 | 159 | 209 | 232 | 236 | 245 | |
| 68 | 76 | 103 | 104 | 159 | 211 | 232 | 236 | 245 | |
| 12 | 68 | 76 | 103 | 104 | 159 | 214 | 232 | 236 | 245 |
| 68 | 76 | 103 | 104 | 159 | 215 | 232 | 236 | 245 | |
| 12 | 68 | 76 | 103 | 104 | 159 | 232 | 236 | 245 | |
| 20 | 68 | 76 | 103 | 104 | 159 | 232 | 236 | 245 | 259 |
| 68 | 87 | 76 | 103 | 104 | 159 | 232 | 236 | 245 | 260 |
| 68 | 76 | 103 | 104 | 159 | 232 | 236 | 245 | 261 | |
| 76 | 103 | 104 | 232 | 236 | 242 | 245 | | | |
| 68 | 76 | 103 | 104 | 159 | 210 | 232 | 236 | 245 | |
| 12 | 48 | 68 | 76 | 103 | 104 | 159 | 232 | 236 | 245 |
| 76 | 103 | 104 | 232 | 236 | 245 | | | | |
| 76 | 103 | 104 | 159 | 192 | 232 | 236 | 245 | | |
| 76 | 103 | 104 | 147 | 159 | 232 | 236 | 245 | 248 | 251 |
| 12 | 68 | 76 | 103 | 104 | 159 | 232 | 236 | 245 | 272 |
| 68 | 76 | 103 | 104 | 159 | 183 | 206 | 232 | 236 | 245 |
| 68 | 76 | 103 | 104 | 159 | 232 | 236 | 245 | 256 | |
| 68 | 76 | 103 | 104 | 159 | 206 | 232 | 236 | 245 | |
| 27 | 68 | 76 | 103 | 104 | 159 | 232 | 236 | 245 | |
| 68 | 76 | 103 | 104 | 116 | 159 | 170 | 185 | 232 | 236 | 245 |
| 61 | 68 | 103 | 104 | 159 | 232 | 236 | 245 | 248 | 252 |
| 43 | 68 | 103 | 104 | 159 | 232 | 236 | 245 | 248 | 252 |
| 68 | 103 | 104 | 159 | 212 | 232 | 236 | 245 | 248 | 252 |
| 68 | 103 | 104 | 99 | 159 | 184 | 232 | 236 | 245 | 248 | 252 |
| 103 | 104 | 159 | 232 | 236 | 245 | 248 | 252 | | |
| 68 | 103 | 104 | 159 | 209 | 232 | 236 | 245 | 248 | 252 |
| 68 | 103 | 104 | 109 | 159 | 232 | 236 | 245 | 248 | 252 |
| 20 | 68 | 103 | 104 | 159 | 232 | 236 | 245 | 248 | 252 |
| 68 | 103 | 104 | 159 | 209 | 232 | 236 | 245 | 248 | 252 |
| 68 | 103 | 104 | 159 | 232 | 236 | 245 | 248 | 252 | 261 |
| 68 | 103 | 104 | 159 | 185 | 232 | 236 | 245 | 248 | 252 |
| 68 | 103 | 104 | 159 | 210 | 232 | 236 | 245 | 248 | 252 |
| 68 | 103 | 104 | 159 | 185 | 210 | 232 | 236 | 245 | 248 | 252 |
| 68 | 103 | 104 | 159 | 212 | 232 | 236 | 245 | 248 | 252 |
| 68 | 103 | 104 | 159 | 213 | 232 | 236 | 245 | 248 | 252 |
| 68 | 103 | 104 | 213 | 232 | 236 | 245 | 248 | 252 | |
| 68 | 103 | 104 | 159 | 215 | 232 | 236 | 245 | 248 | 252 |
| 68 | 103 | 104 | 159 | 216 | 232 | 236 | 245 | 248 | 252 |
| 20 | 68 | 103 | 104 | 159 | 232 | 236 | 245 | 248 | 252 |
| 68 | 103 | 104 | 159 | 173 | 232 | 236 | 245 | 248 | 252 |
| 68 | 103 | 104 | 159 | 232 | 236 | 245 | 248 | 251 | 252 |
| 68 | 103 | 104 | 159 | 206 | 232 | 236 | 245 | 248 | 252 |
| 68 | 103 | 104 | 159 | 232 | 236 | 245 | 248 | 252 | |
| 55 | 68 | 103 | 104 | 159 | 232 | 236 | 245 | 248 | 252 |
| 68 | 103 | 104 | 159 | 232 | 236 | 245 | 248 | 252 | 255 |
| 68 | 103 | 104 | 159 | 232 | 236 | 245 | 248 | 252 | 256 |
| 68 | 103 | 104 | 159 | 232 | 236 | 245 | 248 | 252 | 260 |
| 68 | 103 | 104 | 159 | 232 | 236 | 245 | 248 | 252 | 257 |
| 68 | 103 | 104 | 159 | 232 | 236 | 245 | 248 | 252 | 258 |
| 8 | 68 | 103 | 104 | 159 | 232 | 236 | 245 | 248 | 252 | 269 |
| 68 | 103 | 104 | 116 | 159 | 232 | 236 | 245 | 248 | 252 | 260 |
| 68 | 103 | 104 | 159 | 232 | 236 | 245 | 248 | 252 | 261 |

TABLE VI-continued

| | | | | | | | | | | |
|---|---|---|---|---|---|---|---|---|---|---|
| 68 | 103 | 104 | 159 | 232 | 236 | 245 | 248 | 252 | 261 | |
| 68 | 76 | 103 | 104 | 159 | 232 | 236 | 245 | 248 | 252 | |
| 68 | 103 | 104 | 232 | 236 | 245 | 248 | 252 | | | |
| 103 | 104 | 159 | 232 | 236 | 245 | 248 | 252 | | | |
| 68 | 103 | 104 | 159 | 232 | 236 | 245 | 248 | 252 | | |
| 18 | 68 | 103 | 104 | 159 | 232 | 236 | 245 | 248 | 252 | |
| 68 | 103 | 104 | 159 | 232 | 236 | 245 | 248 | 252 | | |
| 68 | 76 | 101 | 103 | 104 | 159 | 213 | 218 | 232 | 236 | 245 | 260 |
| 68 | 103 | 104 | 159 | 228 | 232 | 236 | 245 | 248 | 252 | |
| 33 | 68 | 76 | 103 | 104 | 159 | 232 | 236 | 245 | 248 | 252 |
| 68 | 76 | 89 | 103 | 104 | 159 | 210 | 213 | 232 | 236 | 245 | 260 |
| 61 | 68 | 76 | 103 | 104 | 159 | 232 | 236 | 245 | 248 | 252 |
| 103 | 104 | 159 | 205 | 210 | 232 | 236 | 245 | | | |
| 61 | 68 | 103 | 104 | 130 | 159 | 232 | 236 | 245 | 248 | 252 |
| 61 | 68 | 103 | 104 | 133 | 137 | 159 | 232 | 236 | 245 | 248 | 252 |
| 61 | 103 | 104 | 133 | 159 | 232 | 236 | 245 | 248 | 252 | |
| 68 | 103 | 104 | 159 | 232 | 236 | 245 | 248 | 252 | | |
| 68 | 103 | 104 | 159 | 218 | 232 | 236 | 245 | 248 | 252 | |
| 61 | 68 | 103 | 104 | 159 | 160 | 232 | 236 | 245 | 248 | 252 |
| 3 | 61 | 68 | 76 | 103 | 104 | 232 | 236 | 245 | 248 | 252 |
| 61 | 68 | 103 | 104 | 159 | 167 | 232 | 236 | 245 | 248 | 252 |
| 97 | 103 | 104 | 159 | 232 | 236 | 245 | 248 | 252 | | |
| 98 | 103 | 104 | 159 | 232 | 236 | 245 | 248 | 252 | | |
| 99 | 103 | 104 | 159 | 232 | 236 | 245 | 248 | 252 | | |
| 101 | 103 | 104 | 159 | 232 | 236 | 245 | 248 | 252 | | |
| 102 | 103 | 104 | 159 | 232 | 236 | 245 | 248 | 252 | | |
| 103 | 104 | 106 | 159 | 232 | 236 | 245 | 248 | 252 | | |
| 103 | 104 | 109 | 159 | 232 | 236 | 245 | 248 | 252 | | |
| 103 | 104 | 159 | 232 | 236 | 245 | 248 | 252 | 261 | | |
| 62 | 103 | 104 | 159 | 232 | 236 | 245 | 248 | 252 | | |
| 103 | 104 | 159 | 184 | 232 | 236 | 245 | 248 | 252 | | |
| 103 | 104 | 159 | 166 | 232 | 236 | 245 | 248 | 252 | | |
| 103 | 104 | 159 | 217 | 232 | 236 | 245 | 248 | 252 | | |
| 20 | 62 | 103 | 104 | 159 | 213 | 232 | 236 | 245 | 248 | 252 |
| 62 | 103 | 104 | 159 | 213 | 232 | 236 | 245 | 248 | 252 | |
| 103 | 104 | 159 | 206 | 217 | 232 | 236 | 245 | 248 | 252 | |
| 62 | 103 | 104 | 159 | 206 | 232 | 236 | 245 | 248 | 252 | |
| 103 | 104 | 130 | 159 | 232 | 236 | 245 | 248 | 252 | | |
| 103 | 104 | 131 | 159 | 232 | 236 | 245 | 248 | 252 | | |
| 27 | 103 | 104 | 159 | 232 | 236 | 245 | 248 | 252 | | |
| 38 | 103 | 104 | 159 | 232 | 236 | 245 | 248 | 252 | | |
| 38 | 76 | 103 | 104 | 159 | 213 | 232 | 236 | 245 | 260 | |
| 68 | 76 | 103 | 104 | 159 | 213 | 232 | 236 | 245 | 260 | 271 |
| 68 | 76 | 103 | 104 | 159 | 209 | 213 | 232 | 236 | 245 | 260 |
| 68 | 76 | 103 | 104 | 159 | 210 | 213 | 232 | 236 | 245 | 260 |
| 68 | 76 | 103 | 104 | 159 | 205 | 213 | 232 | 236 | 245 | 260 |
| 68 | 76 | 103 | 104 | 159 | 210 | 232 | 236 | 245 | 260 | |
| 68 | 103 | 104 | 159 | 213 | 232 | 236 | 245 | 260 | | |
| 76 | 103 | 104 | 159 | 213 | 232 | 236 | 245 | 260 | | |
| 68 | 103 | 104 | 159 | 209 | 232 | 236 | 245 | | | |
| 68 | 103 | 104 | 159 | 210 | 232 | 236 | 245 | | | |
| 68 | 103 | 104 | 159 | 230 | 232 | 236 | 245 | | | |
| 68 | 103 | 104 | 159 | 126 | 232 | 236 | 245 | | | |
| 68 | 103 | 104 | 159 | 205 | 232 | 236 | 245 | | | |
| 68 | 103 | 104 | 159 | 210 | 232 | 236 | 245 | | | |
| 103 | 104 | 159 | 230 | 236 | 245 | | | | | |
| 68 | 103 | 104 | 159 | 232 | 236 | 245 | 260 | | | |
| 103 | 104 | 159 | 232 | 236 | 245 | | | | | |
| 68 | 103 | 104 | 159 | 174 | 232 | 236 | 245 | 257 | | |
| 68 | 103 | 104 | 159 | 194 | 232 | 236 | 245 | 257 | | |
| 68 | 103 | 104 | 159 | 209 | 232 | 236 | 245 | 257 | | |
| 103 | 104 | 159 | 232 | 236 | 245 | 257 | | | | |
| 68 | 76 | 103 | 104 | 159 | 213 | 232 | 236 | 245 | 260 | 261 |
| 68 | 103 | 104 | 159 | 232 | 236 | 245 | 257 | 261 | | |
| 103 | 104 | 159 | 213 | 232 | 236 | 245 | 260 | | | |
| 103 | 104 | 159 | 210 | 232 | 236 | 245 | 248 | 252 | | |
| 103 | 104 | 159 | 209 | 232 | 236 | 245 | 257 | | | |
| 68 | 76 | 103 | 104 | 159 | 210 | 213 | 232 | 236 | 245 | 260 |
| 12 | 103 | 104 | 159 | 209 | 213 | 232 | 236 | 245 | 260 | |
| 103 | 104 | 209 | 232 | 236 | 245 | 257 | | | | |
| 103 | 104 | 159 | 205 | 210 | 213 | 232 | 236 | 245 | 260 | |
| 103 | 104 | 159 | 205 | 209 | 232 | 236 | 245 | 260 | | |
| 68 | 103 | 104 | 159 | 205 | 209 | 210 | 232 | 236 | 245 | |
| 103 | 104 | 159 | 205 | 209 | 210 | 232 | 236 | 245 | 257 | |
| 103 | 104 | 159 | 205 | 209 | 232 | 236 | 245 | 257 | | |
| 68 | 103 | 104 | 159 | 205 | 209 | 210 | 232 | 236 | 245 | 260 |
| 103 | 104 | 159 | 205 | 209 | 210 | 232 | 236 | 245 | | |
| 103 | 104 | 159 | 209 | 210 | 232 | 236 | 245 | | | |
| 103 | 104 | 159 | 205 | 210 | 232 | 236 | 245 | | | |

TABLE VI-continued

| | | | | | | | | | | | |
|---|---|---|---|---|---|---|---|---|---|---|---|
| 68 | 103 | 104 | 128 | 159 | 232 | 236 | 245 | | | | |
| 48 | 103 | 104 | 159 | 230 | 236 | 245 | | | | | |
| 48 | 68 | 103 | 104 | 159 | 209 | 232 | 236 | 245 | | | |
| 48 | 68 | 103 | 104 | 159 | 232 | 236 | 245 | 248 | 252 | | |
| 48 | 68 | 103 | 104 | 159 | 232 | 236 | 245 | 257 | 261 | | |
| 102 | 103 | 104 | 159 | 212 | 232 | 236 | 245 | 248 | 252 | | |
| 12 | 102 | 103 | 104 | 159 | 212 | 232 | 236 | 245 | 248 | 252 | |
| 101 | 102 | 103 | 104 | 159 | 212 | 232 | 236 | 245 | 248 | 252 | |
| 98 | 102 | 103 | 104 | 159 | 212 | 232 | 236 | 245 | 248 | 252 | |
| 102 | 103 | 104 | 159 | 213 | 232 | 236 | 245 | 248 | 252 | | |
| 103 | 104 | 131 | 159 | 232 | 236 | 245 | 248 | 252 | | | |
| 103 | 104 | 159 | 184 | 232 | 236 | 245 | 248 | 252 | | | |
| 103 | 104 | 159 | 232 | 236 | 244 | 245 | 248 | 252 | | | |
| 62 | 103 | 104 | 159 | 213 | 232 | 236 | 245 | 248 | 252 | 256 | |
| 12 | 62 | 103 | 104 | 159 | 213 | 232 | 236 | 245 | 248 | 252 | |
| 101 | 103 | 104 | 159 | 185 | 232 | 236 | 245 | 248 | 252 | | |
| 101 | 103 | 104 | 159 | 206 | 232 | 236 | 245 | 248 | 252 | | |
| 101 | 103 | 104 | 159 | 213 | 232 | 236 | 245 | 248 | 252 | | |
| 98 | 102 | 103 | 104 | 159 | 232 | 236 | 245 | 248 | 252 | | |
| 101 | 102 | 103 | 104 | 159 | 232 | 236 | 245 | 248 | 252 | | |
| 98 | 102 | 103 | 104 | 159 | 212 | 232 | 236 | 245 | 248 | 252 | |
| 98 | 102 | 103 | 104 | 159 | 212 | 232 | 236 | 248 | 252 | | |
| 62 | 103 | 104 | 109 | 159 | 213 | 232 | 236 | 245 | 248 | 252 | |
| 62 | 103 | 104 | 159 | 212 | 213 | 232 | 236 | 245 | 248 | 252 | |
| 62 | 101 | 103 | 104 | 159 | 212 | 213 | 232 | 236 | 245 | 248 | 252 |
| 103 | 104 | 159 | 232 | 245 | 248 | 252 | | | | | |
| 103 | 104 | 159 | 230 | 245 | | | | | | | |
| 62 | 103 | 104 | 130 | 159 | 213 | 232 | 236 | 245 | 248 | 252 | |
| 101 | 103 | 104 | 130 | 159 | 232 | 236 | 245 | 248 | 252 | | |
| 101 | 103 | 104 | 128 | 159 | 232 | 236 | 245 | 248 | 252 | | |
| 62 | 101 | 103 | 104 | 159 | 213 | 232 | 236 | 245 | 248 | 252 | |
| 62 | 103 | 104 | 128 | 159 | 213 | 232 | 236 | 245 | 248 | 252 | |
| 62 | 103 | 104 | 128 | 159 | 213 | 232 | 236 | 245 | 248 | 252 | |
| 101 | 103 | 104 | 159 | 232 | 236 | 245 | 248 | 252 | 260 | | |
| 101 | 103 | 104 | 131 | 159 | 232 | 236 | 245 | 248 | 252 | | |
| 98 | 101 | 103 | 104 | 159 | 232 | 236 | 245 | 248 | 252 | | |
| 99 | 101 | 103 | 104 | 159 | 232 | 236 | 245 | 248 | 252 | | |
| 101 | 103 | 104 | 159 | 212 | 232 | 236 | 245 | 248 | 252 | | |
| 101 | 103 | 104 | 159 | 209 | 232 | 236 | 245 | 248 | 252 | | |
| 101 | 103 | 104 | 159 | 210 | 232 | 236 | 245 | 248 | 252 | | |
| 101 | 103 | 104 | 159 | 205 | 232 | 236 | 245 | 248 | 252 | | |
| 101 | 103 | 104 | 159 | 230 | 236 | 245 | | | | | |
| 101 | 103 | 104 | 159 | 194 | 232 | 236 | 245 | 248 | 252 | | |
| 76 | 101 | 103 | 104 | 159 | 194 | 232 | 236 | 245 | 248 | 252 | |
| 101 | 103 | 104 | 159 | 230 | 232 | 236 | 245 | 248 | 252 | | |
| 62 | 103 | 104 | 159 | 185 | 206 | 213 | 232 | 236 | 245 | 248 | 252 | 271 |

An even more preferred protease variant useful in the cleaning compositions of the present invention include a substitution set (one substitution set per row in the following Table II) selected from the group consisting of:

TABLE VII

| | | | | | | | | |
|---|---|---|---|---|---|---|---|---|
| N76D | S103A | V104I | S212P | E271V | | | | |
| N76D | S103A | V104I | N252K | N261Y | | | | |
| N76D | S103A | V104I | S212P | G258R | | | | |
| V4E | N76D | S103A | V104I | G159D | L217E | N252D | | |
| Q12H | N62H | N76D | S103A | V104I | G159D | | | |
| N76D | S103A | V104I | S212P | V268F | E271V | | | |
| N76D | S87R | S103A | V104I | S212P | E271V | | | |
| N76D | S103A | V104I | S212P | Q245L | E271V | | | |
| N76D | S103A | V104I | T134S | S141N | S212P | E271V | | |
| N76D | S103A | V104I | S212P | Q236L | N243S | E271V | | |
| G20V | N62S | N76D | S103A | V104I | | | | |
| V68A | N76D | S103A | V104I | G159D | A232V | Q236H | Q245R | |
| N76D | S103A | V104I | A232V | Q245R | | | | |
| S24T | V68A | N76D | S103A | V104I | G159D | A232V | Q236H | Q245R |
| V68A | S103A | V104I | G159D | A232V | Q236H | Q245R | N252K | |
| V68A | N76D | S103A | V104I | G159D | T213R | A232V | Q236H | Q245R | T260A |
| V68A | S103A | V104I | G159D | A232V | Q236H | Q245R | N248D | N252K |
| V68A | S103A | V104I | G159D | A232V | Q236H | Q245R | | |
| V68A | S103A | V104I | N140D | G159D | A232V | Q236H | Q245R | N252K |
| N43S | V68A | S103A | V104I | G159D | A232V | Q236H | Q245R | N252K |
| N43K | V68A | S103A | V104I | G159D | A232V | Q236H | Q245R | |
| N43D | V68A | S103A | V104I | G159D | A232V | Q236H | Q245R | N252K |
| V68A | S87G | S103A | V104I | G159D | A232V | Q236H | Q245R | N252K | R275S |

TABLE VII-continued

| | | | | | | | | | | |
|---|---|---|---|---|---|---|---|---|---|---|
| V68A | S103A | V104I | G159D | A232V | Q236H | Q245R | L257V | | | |
| V68A | S103A | V104I | N116D | G159D | A232V | Q236H | Q245R | | | |
| V68A | S103A | V104I | G159D | A232V | Q236H | Q245R | N248D | | | |
| R10C | V68A | S103A | V104I | G159D | A232V | Q236H | Q245R | | | |
| V68A | S103A | V104I | G159D | V203E | A232V | Q236H | Q245R | | | |
| V68A | S103A | V104I | G159D | A232V | Q236H | K237E | Q245R | | | |
| V68A | N76D | 179N | S103A | V104I | G159D | A232V | Q236H | Q245R | | |
| V68A | S103A | V104I | G159D | N183D | A232V | Q236H | Q245R | | | |
| V68A | S103A | V104I | G159D | A174V | Q206L | A232V | Q236H | Q245R | | |
| V68A | S103A | V104I | G159D | S188C | A232V | Q236H | Q245R | | | |
| V68A | S103A | V104I | G159D | A230T | A232V | Q236H | Q245R | | | |
| V68A | A98T | S103A | V104I | G159D | A232V | Q236H | Q245R | | | |
| V68A | S103A | V104I | G159D | A215T | A232V | Q236H | Q245R | | | |
| V68A | S103A | V104I | G159D | A232V | Q236H | Q245R | N248S | | | |
| V68A | N76D | S103A | V104I | G159D | A232V | Q236H | Q245R | | | |
| V68A | N76D | S103A | V104I | G159D | P210R | A232V | Q236H | Q245R | | |
| V68A | N76D | S103A | V104I | G159D | A232V | Q236H | Q245R | L257V | | |
| N76D | S103A | V104I | A232V | Q236H | Q245R | L257V | | | | |
| V68A | S103A | V104I | G159D | A232V | Q236H | Q245R | L257V | R275H | | |
| N76D | S103A | V104I | L257V | R275H | | | | | | |
| V68A | S103A | V104I | G159D | T224A | A232V | Q236H | Q245R | L257V | | |
| N76D | S103A | V104I | G159D | A232V | Q236H | Q245R | L257V | | | |
| V68A | N76D | S103A | V104I | G159D | Y209W | A232V | Q236H | Q245R | | |
| V68A | N76D | S103A | V104I | G159D | G211R | A232V | Q236H | Q245R | | |
| V68A | N76D | S103A | V104I | G159D | G211V | A232V | Q236H | Q245R | | |
| Q12R | V68A | N76D | S103A | V104I | G159D | Y214L | A232V | Q236H | Q245R | |
| V68A | N76D | S103A | V104I | G159D | A215R | A232V | Q236H | Q245R | | |
| Q12R | V68A | N76D | S103A | V104I | G159D | A232V | Q236H | Q245R | | |
| G20R | V68A | N76D | S103A | V104I | G159D | A232V | Q236H | Q245R | S259G | |
| V68A | S87R | N76D | S103A | V104I | G159D | A232V | Q236H | Q245R | T260V | |
| V68A | N76D | S103A | V104I | G159D | A232V | Q236H | Q245R | N261G | | |
| V68A | N76D | S103A | V104I | G159D | A232V | Q236H | Q245R | N261W | | |
| N76D | S103A | V104I | A232V | Q236H | 5242P | Q245R | | | | |
| V68A | N76D | S103A | V104I | G159D | P210L | A232V | Q236H | Q245R | | |
| Q12R | A48V | V68A | N76D | S103A | V104I | G159D | A232V | Q236H | Q245R | |
| N76D | S103A | V104I | A232V | Q236H | Q245R | | | | | |
| N76D | S103A | V104I | G159D | Y192F | A232V | Q236H | Q245R | | | |
| N76D | S103A | V104I | V147I | G159D | A232V | Q236H | Q245R | N248S | K251R | |
| Q12R | V68A | N76D | S103A | V104I | G159D | A232V | Q236H | Q245R | A272S | |
| V68A | N76D | S103A | V104I | G159D | N183K | Q206L | A232V | Q236H | Q245R | |
| V68A | N76D | S103A | V104I | G159D | A232V | Q236H | Q245R | S256R | | |
| V68A | N76D | S103A | V104I | G159D | Q206R | A232V | Q236H | Q245R | | |
| K27R | V68A | N76D | S103A | V104I | G159D | A232V | Q236H | Q245R | | |
| V68A | N76D | S103A | V104I | N116T | G159D | R170S | N185S | A232V | Q236H | Q245R |
| G61E | V68A | S103A | V104I | G159D | A232V | Q236H | Q245R | N248D | N252K | |
| N43D | V68A | S103A | V104I | G159D | A232V | Q236H | Q245R | N248D | N252K | |
| V68A | S103A | V104I | G159D | S212P | A232V | Q236H | Q245R | N248D | N252K | |
| V68A | S103A | V104I | 599N | G159D | N184D | A232V | Q236H | Q245R | N248D | N252K |
| S103A | V104I | G159D | A232V | Q236H | Q245R | N248D | N252K | | | |
| V68A | S103A | V104I | G159D | Y209W | A232V | Q236H | Q245R | N248D | N252K | |
| V68A | S103A | V104I | Q109R | G159D | A232V | Q236H | Q245R | N248D | N252K | |
| G20R | V68A | S103A | V104I | G159D | A232V | Q236H | Q245R | N248D | N252K | |
| V68A | S103A | V104I | G159D | Y209F | A232V | Q236H | Q245R | N248D | N252K | |
| V68A | S103A | V104I | G159D | A232V | Q236H | Q245R | N248D | N252K | N261D | |
| V68A | S103A | V104I | G159D | N185D | A232V | Q236H | Q245R | N248D | N252K | |
| V68A | S103A | V104I | G159D | P210R | A232V | Q236H | Q245R | N248D | N252K | |
| V68A | S103A | V104I | G159D | P210T | A232V | Q236H | Q245R | N248D | N252K | |
| V68A | S103A | V104I | G159D | P210S | A232V | Q236H | Q245R | N248D | N252K | |
| V68A | S103A | V104I | G159D | N185D | P210L | A232V | Q236H | Q245R | N248D | N252K |
| V68A | S103A | V104I | G159D | P210L | A232V | Q236H | Q245R | N248D | N252K | |
| V68A | S103A | V104I | G159D | S212A | A232V | Q236H | Q245R | N248D | N252K | |
| V68A | S103A | V104I | G159D | S212G | A232V | Q236H | Q245R | N248D | N252K | |
| V68A | S103A | V104I | G159D | S212E | A232V | Q236H | Q245R | N248D | N252K | |
| V68A | S103A | V104I | 6159D | T213E | A232V | Q236I | Q245R | N248D | N252K | |
| V68A | S103A | V104I | T213S | A232V | Q236H | Q245R | N248D | N252K | | |
| V68A | A103V | V104I | G159D | T213E | A232V | Q236H | Q245R | N248D | N252K | |
| V68A | S103A | V104I | G159D | T213R | A232V | Q236H | Q245R | N248D | N252K | |
| V68A | S103A | V104I | G159D | T213G | A232V | Q236H | Q245R | N248D | N252K | |
| V68A | S103A | V104I | G159D | A215V | A232V | Q236H | Q245R | N248D | N252K | |
| V68A | S103A | V104I | G159D | A215R | A232V | Q236H | Q245R | N248D | N252K | |
| V68A | S103A | V104I | G159D | S216T | A232V | Q236H | Q245R | N248D | N252K | |
| V68A | S103A | V104I | G159D | S216V | A232V | Q236H | Q245R | N248D | N252K | |
| V68A | S103A | V104I | G159D | S216C | A232V | Q236H | Q245R | N248D | N252K | |
| G20A | V68A | S103A | V104I | G159D | A232V | Q236H | Q245R | N248D | N252K | |
| V68A | S103A | V104I | G159D | N173D | A232V | Q236H | Q245R | N248D | N252K | |
| V68A | S103A | V104I | G159D | A232V | Q236H | Q245R | N248D | K251V | N252K | |
| V68A | S103A | V104I | G159D | Q206R | A232V | Q236H | Q245R | N248D | N252K | |
| V68A | S103A | V104I | G159D | A232V | Q236H | Q245R | N248D | N252F | | |
| V68A | S103A | V104I | G159D | A232V | Q236H | Q245R | N248D | N252L | | |

TABLE VII-continued

| | | | | | | | | | | |
|---|---|---|---|---|---|---|---|---|---|---|
| P55S | V68A | S103A | V104I | G159D | A232V | Q236H | Q245R | N248D | N252F | |
| V68A | S103A | V104I | G159D | A232V | Q236H | Q245R | N248D | N252K | T255V | |
| V68A | S103A | V104I | G159D | A232V | Q236H | Q245R | N248D | N252K | S256N | |
| V68A | S103A | V104I | G159D | A232V | Q236H | Q245R | N248D | N252K | S256E | |
| V68A | S103A | V104I | G159D | A232V | Q236H | Q245R | N248D | N252K | S256R | |
| V6SA | S103A | V104I | G159D | A232V | Q236H | Q245R | N248D | N252K | T260R | |
| V68A | S103A | V104I | G159D | A232V | Q236H | Q245R | N248D | N252K | L257R | |
| V68A | S103A | V104I | G159D | A232V | Q236H | Q245R | N248D | N252K | G258D | |
| 18V | V68A | S103A | V104I | G159D | A232V | Q236H | Q245R | N248D | N252K | N269D |
| V68A | S103A | V104I | N116S | G159D | A232V | Q236H | Q245R | N248D | N252K | T260E |
| V68A | S103A | V104I | G159D | A232V | Q236H | Q245R | N248D | N252K | N261R | |
| V68A | S103A | V104I | G159D | A232V | Q236H | Q245R | N248D | N252K | N261D | |
| V68A | N76D | S103A | V104I | G159D | A232V | Q236H | Q245R | N248D | N252K | |
| V68A | S103A | V104I | A232V | Q236H | Q245R | N248D | N252K | | | |
| S103A | V104I | G159D | A232S | Q236H | Q245R | N248D | N252K | | | |
| V68A | S103A | V104I | G159D | A232V | Q236H | Q245R | N248D | N252K | | |
| N18S | V68A | S103A | V104I | G159D | A232V | Q236H | Q245R | N248D | N252K | |
| V68A | S103A | V104I | G159D | A232V | Q236H | Q245V | N248D | N252K | | |
| V68A | N76D | S101T | S103A | V104I | G159D | T213R | N218S | A232V | Q236H | Q245R | T260A |
| V68A | S103A | V104I | G159D | A228V | A232V | Q236H | Q245R | N248D | N252K | |
| T33S | V68A | N76D | S103A | V104I | G159D | A232V | Q236H | Q245R | N248D | N252K |
| V68A | N76D | E89D | S103A | V104I | G159D | P210L | T213R | A232V | Q236H | Q245R | T260A |
| G6IE | V68A | N76D | S103A | V104I | G159D | A232V | Q236H | Q245R | N248D | N252K |
| S103A | V104I | G159D | V205I | P210I | A232V | Q236H | Q245R | | | |
| G61E | V68A | S103A | V104I | S130A | G159D | A232V | Q236H | Q245R | N248D | N252K |
| G61E | V6BA | S103A | V104I | A133S | Q137R | G159D | A232V | Q236H | Q245R | N248D | N252K |
| G61E | S103A | V104I | A133V | G159D | A232V | Q236H | Q245R | N248D | N252K |
| V68A | S103A | V104I | G159D | A232V | Q236H | Q245R | N248G | N252K | | |
| V68A | S103A | V104I | G159D | N218S | A232V | Q236H | Q245R | N248D | N252K | |
| G61E | V68A | S103A | V104I | G159D | S160V | A232V | Q236H | Q245R | N248D | N252K |
| S3L | G61E | V68A | N76D | S103A | V104I | A232V | Q236H | Q245R | N248D | N252K |
| G61E | V68A | S103A | V104I | G159D | S167F | A232V | Q236H | Q245R | N248D | N252K |
| G97E | S103A | V104I | G159D | A232V | Q236H | Q245R | N248D | N252K | | |
| A98D | S103A | V104I | G159D | A232V | Q236H | Q245R | N248D | N252K | | |
| S99E | S103A | V104I | G159D | A232V | Q236H | Q245R | N248D | N252K | | |
| S101E | S103A | V104I | G159D | A232V | Q236H | Q245R | N248D | N252K | | |
| S101G | S103A | V104I | G159D | A232V | Q236H | Q245R | N248D | N252K | | |
| G102A | S103A | V104I | G159D | A232V | Q236H | Q245R | N248D | N252K | | |
| S103A | V104I | S106E | G159D | A232V | Q236H | Q245R | N248D | N252K | | |
| S103A | V104I | Q109E | G159D | A232V | Q236H | Q245R | N248D | N252K | | |
| S103A | V104I | G159D | A232V | Q236H | Q245R | N248D | N252K | N261R | | |
| S103A | V104I | Q109R | G159D | A232V | Q236H | Q245R | N248D | N252K | | |
| N62D | S103A | V104I | G159D | A232V | Q236H | Q245R | N248D | N252K | | |
|

TABLE VII-continued

| | | | | | | | | | |
|---|---|---|---|---|---|---|---|---|---|
| S103A | V104I | G159D | Y209W | A232V | Q236H | Q245R | L257V | | |
| V68A | N76D | S103A | V104I | G159D | P210L | T213R | A232V | Q236H Q245R | T260A |
| Q12R | S103A | V104I | G159D | Y209W | T213R | A232V | Q236H Q245R | T260A | |
| S103A | V104I | Y209W | A232V | Q236H | Q245R | L257V | | | |
| S103A | V104I | G159D | V205I | P210I | T213R | A232V | Q236H Q245R | T260A | |
| S103A | V104I | G159D | V205I | Y209W | A232V | Q236H | Q245R T260A | | |
| V68A | S103A | V104I | G159D | V205I | Y209W | P210I | A232V Q236H | Q245R | |
| S103A | V104I | G159D | V205I | Y209W | P210I | A232V | Q236H Q245R | L257V | |
| S103A | V104I | G159D | V205I | Y209W | A232V | Q236H | Q245R L257V | | |
| V68A | S103A | V104I | G159D | V205I | Y209W | P210I | A232V Q236H | Q245R | T260A |
| S103A | V104I | G159D | V205I | Y209W | P210I | A232V | Q236H Q245R | | |
| S103A | V104I | G159D | Y209W | P210I | A232V | Q236H | Q245R | | |
| S103A | V104I | G159D | V205I | P210I | A232V | Q236H | Q245R | | |
| V68A | S103A | V104I | S128L | G159D | A232V | Q236H | Q245R | | |
| A48V | S103A | V104I | G159D | A230V | Q236H | Q245R | | | |
| A48V | V68A | S103A | V104I | G159D | Y209W | A232V | Q236H Q245R | | |
| A48V | V68A | S103A | V104I | G159D | A232V | Q236H | Q245R N248D | N252K | |
| A48V | V68A | S103A | V104I | G159D | A232V | Q236H | Q245R L257V | N261W | |
| G102A | S103A | V104I | G159D | S212G | A232V | Q236H | Q245R N248D | N252K | |
| Q12R | G102A | S103A | V104I | G159D | S212G | A232V | Q236H Q245R | N248D | N252K |
| S101G | G102A | S103A | V104I | G159D | S212G | A232V | Q236H Q245R | N248D | N252K |
| A98L | G102A | S103A | V104I | G159D | S212G | A232V | Q236H Q245R | N248D | N252K |
| G102A | S103A | V104I | G159D | T213R | A232V | Q236H | Q245R N248D | N252K | |
| S103A | V104I | P131V | G159D | A232V | Q236H | Q245R | N248D N252K | | |
| S103A | V104I | G159D | N184S | A232V | Q236H | Q245R | N248D N252K | | |
| S103A | V104I | G159D | N184G | A232V | Q236H | Q245R | N248D N252K | | |
| S103A | V104I | G159D | A232V | Q236H | V244T | Q245R | N248D N252K | | |
| S103A | V104I | G159D | A232V | Q236H | V244A | Q245R | N248D N252K | | |
| N62D | S103A | V104I | G159D | T213R | A232V | Q236H | Q245R N248D | N252K | S256R |
| Q12R | N62D | S103A | V104I | G159D | T213R | A232V | Q236H Q245R | N248D | N252K |
| S101G | S103A | V104I | G159D | N18SD | A232V | Q236H | Q245R N248D | N252K | |
| S101G | S103A | V104I | G159D | Q206E | A232V | Q236H | Q245R N248D | N252K | |
| S101G | S103A | V104I | G159D | T213Q | A232V | Q236H | Q245R N248D | N252K | |
| A98L | G102A | S103A | V104I | G159D | A232V | Q236H | Q245R N248D | N252K | |
| S101G | G102A | S103A | V104I | G159D | A232V | Q236H | Q245R N248D | N252K | |
| A98L | G102A | S103A | V104I | G159D | S212G | A232V | Q236H Q245R | N248D | N252K |
| A98L | G102A | S103A | V104I | G159D | S212G | A232V | Q236H N248D | N252K | |
| N62D | S103A | V104I | Q109R | G159D | T213R | A232V | Q236H Q245R | N248D | N252K |
| N62D | S103A | V104I | G159D | S212G | T213R | A232V | Q236H Q245R | N248D | N252K |
| N62D | S101G | S103A | V104I | G159D | S212G | T213R | A232V Q236H | Q245R N248D | N252K |
| S103A | V104I | G159D | A232V | Q245R | N248D | N252K | | | |
| S103A | V104I | G159D | A230V | Q245R | | | | | |
| N62D | S103A | V104I | SI30G | G159D | T213R | A232V | Q236H Q245R | N248D | N252K |
| S101G | S103A | V104I | S130G | G159D | A232V | Q236H | Q245R N248D | N252K | |
| S101G | S103A | V104I | S128G | G159D | A232V | Q236H | Q245R N248D | N252K | |
| S101G | S103A | V104I | S128L | G159D | A232V | Q236H | Q245R N248D | N252K | |
| N62D | S101G | S103A | V104I | G159D | T213R | A232V | Q236H Q245R | N248D | N252K |
| N62D | S103A | V104I | S128G | G159D | T213R | A232V | Q236H Q245R | N248D | N252K |
| N62D | S103A | V104I | S128L | G159D | T213R | A232V | Q236H Q245R | N248D | N252K |
| S101G | S103A | V104I | G159D | A232V | Q236H | Q245R | N248D N252K | T260A | |
| S101G | S103A | V104I | P13IV | G159D | A232V | Q236H | Q245R N248D | N252K | |
| A98V | S101G | S103A | V104I | G159D | A232V | Q236H | Q245R N248D | N252K | |
| S99G | S101G | S103A | V104I | G159D | A232V | Q236H | Q245R N248D | N252K | |
| S101G | S103A | V104I | G159D | S212G | A232V | Q236H | Q245R N248D | N252K | |
| S101G | S103A | V104I | G159D | Y209W | A232V | Q236H | Q245R N248D | N252K | |
| S101G | S103A | V104I | G159D | P210I | A232V | Q236H | Q245R N248D | N252K | |
| S10IG | S103A | V104I | G159D | V205I | A232V | Q236H | Q245R N248D | N252K | |
| S101G | S103A | V104I | G159D | A230V | Q236H | Q245R | | | |
| S101G | S103A | V104I | G159D | A194P | A232V | Q236H | Q245R N248D | N252K | |
| N76D | S101G | S103A | V104I | G159D | A194P | A232V | Q236H Q245W | N248D | N252K |
| S101G | S103A | V104I | G159D | A230V | A232V | Q236H | Q245R N248D | N252K | |
| N62D | S103A | V104I | G159D | N18SD | Q206E | T213R | A232V Q236H | Q245R N248D | N252K E271Q |

Still yet an even more preferred protease variant useful in the cleaning composition of the present invention include a substitution set selected from the group consisting of the substitution sets in Table VI except for the following substitution set of Table VIII:

TABLE VIII

| 68 | 76 | 103 | 104 | 116 | 159 | 170 | 185 | 232 | 236 | 245 |
|---|---|---|---|---|---|---|---|---|---|---|

Still yet an even more preferred protease variant useful in the cleaning composition of the present invention include a substitution set selected from the group consisting of the substitution sets in Table IX:

TABLE IX

| | | | | | | | | | | |
|---|---|---|---|---|---|---|---|---|---|---|
| 68 | 103 | 104 | 159 | 232 | 236 | 245 | 252 | | | |
| 68 | 76 | 103 | 104 | 159 | 213 | 232 | 236 | 245 | 260 | |
| 68 | 103 | 104 | 159 | 232 | 236 | 245 | 248 | 252 | | |
| 68 | 103 | 104 | 159 | 232 | 236 | 245 | | | | |
| 68 | 103 | 104 | 140 | 159 | 232 | 236 | 245 | 252 | | |
| 43 | 68 | 103 | 104 | 159 | 232 | 236 | 245 | 252 | | |
| 43 | 68 | 103 | 104 | 159 | 232 | 236 | 245 | | | |
| 68 | 103 | 104 | 159 | 232 | 236 | 245 | 257 | | | |
| 68 | 76 | 103 | 104 | 159 | 210 | 232 | 236 | 245 | | |
| 68 | 103 | 104 | 159 | 224 | 232 | 236 | 245 | 257 | | |
| 76 | 103 | 104 | 159 | 232 | 236 | 245 | 257 | | | |
| 68 | 76 | 103 | 104 | 159 | 211 | 232 | 236 | 245 | | |
| 12 | 68 | 76 | 103 | 104 | 159 | 214 | 232 | 236 | 245 | |
| 68 | 76 | 103 | 104 | 159 | 215 | 232 | 236 | 245 | | |
| 12 | 68 | 76 | 103 | 104 | 159 | 232 | 236 | 245 | | |
| 20 | 68 | 76 | 103 | 104 | 159 | 232 | 236 | 245 | 259 | |
| 68 | 76 | 87 | 103 | 104 | 159 | 232 | 236 | 245 | 260 | |
| 68 | 76 | 103 | 104 | 159 | 232 | 236 | 245 | 261 | | |
| 12 | 48 | 68 | 76 | 103 | 104 | 159 | 232 | 236 | 245 | |
| 76 | 103 | 104 | 159 | 192 | 232 | 236 | 245 | | | |
| 76 | 103 | 104 | 147 | 159 | 232 | 236 | 245 | 248 | 251 | |
| 12 | 68 | 76 | 103 | 104 | 159 | 232 | 236 | 245 | 272 | |
| 68 | 76 | 103 | 104 | 159 | 183 | 206 | 232 | 236 | 245 | |
| 68 | 76 | 103 | 104 | 159 | 232 | 236 | 245 | 256 | | |
| 68 | 76 | 103 | 104 | 159 | 206 | 232 | 236 | 245 | | |
| 27 | 68 | 76 | 103 | 104 | 159 | 232 | 236 | 245 | | |
| 68 | 103 | 104 | 159 | 212 | 232 | 236 | 245 | 248 | 252 | |
| 103 | 104 | 159 | 232 | 236 | 245 | 248 | 252 | | | |
| 68 | 103 | 104 | 159 | 209 | 232 | 236 | 245 | 248 | 252 | |
| 68 | 103 | 104 | 109 | 159 | 232 | 236 | 245 | 248 | 252 | |
| 20 | 68 | 103 | 104 | 159 | 232 | 236 | 245 | 248 | 252 | |
| 68 | 103 | 104 | 159 | 209 | 232 | 236 | 245 | 248 | 252 | |
| 68 | 103 | 104 | 159 | 210 | 232 | 236 | 245 | 248 | 252 | |
| 68 | 103 | 104 | 159 | 212 | 232 | 236 | 245 | 248 | 252 | |
| 68 | 103 | 104 | 159 | 213 | 232 | 236 | 245 | 248 | 252 | |
| 68 | 103 | 104 | 213 | 232 | 236 | 245 | 248 | 252 | | |
| 68 | 103 | 104 | 159 | 215 | 232 | 236 | 245 | 248 | 252 | |
| 68 | 103 | 104 | 159 | 216 | 232 | 236 | 245 | 248 | 252 | |
| 20 | 68 | 103 | 104 | 159 | 232 | 236 | 245 | 248 | 252 | |
| 68 | 103 | 104 | 159 | 232 | 236 | 245 | 248 | 252 | 255 | |
| 68 | 103 | 104 | 159 | 232 | 236 | 245 | 248 | 252 | 256 | |
| 68 | 103 | 104 | 159 | 232 | 236 | 245 | 248 | 252 | 260 | |
| 68 | 103 | 104 | 159 | 228 | 232 | 236 | 245 | 248 | 252 | |
| 68 | 76 | 89 | 103 | 104 | 159 | 210 | 213 | 232 | 236 | 245 | 260 |
| 68 | 103 | 104 | 159 | 218 | 232 | 236 | 245 | 248 | 252 | |

Still yet an even more preferred protease variant useful in the cleaning composition of the present invention include a substitution set selected from the group consisting of the substitution sets in Table X:

TABLE X

| | | | | | | | | | | | |
|---|---|---|---|---|---|---|---|---|---|---|---|
| V68A | S103A | V104I | G159D | A228V | A232V | Q236H | Q245R | N248D | N252K | | |
| V68A | S103A | V104I | G159D | N218S | A232V | Q236H | Q245R | N248D | N252K | | |
| G20R | V68A | S103A | V104I | G159D | A232V | Q236H | Q245R | N248D | N252K | | |
| V68A | N76D | E89D | S103A | V104I | G159D | P210L | T213R | A232V | Q236H | Q245R | T260A |
| V68A | S103A | V104I | G159D | A232V | Q236H | Q245R | N248D | N252K | S256R | | |
| V68A | S103A | V104I | G159D | A232V | Q236H | Q245R | N248D | N252K | T160R | | |
| V68A | S103A | V104I | G159D | A232V | Q236H | Q245R | N248D | N252K | T255V | | |
| V68A | S103A | V104I | G159D | A232V | Q236H | Q245R | N248D | N252K | S256N | | |
| V68A | S103A | V104I | G159D | A232V | Q236H | Q245R | N248D | N252L | | | |
| V68A | S103A | V104I | G159D | T213R | A232V | Q236H | Q245R | N248D | N252K | | |
| V68A | S103A | V104I | G159D | A215V | A232V | Q236H | Q245R | N248D | N252K | | |
| V68A | S103A | V104I | G159D | A215R | A232V | Q236H | Q245R | N248D | N252K | | |
| V68A | S103A | V104I | G159D | S216T | A232V | Q236H | Q245R | N248D | N252K | | |
| V68A | S103A | V104I | G159D | S216V | A232V | Q236H | Q245R | N248D | N252K | | |
| V68A | S103A | V104I | T213S | A232V | Q236H | Q245R | N248D | N252K | | | |
| V68A | S103A | V104I | G159D | P210L | A232V | Q236H | Q245R | N248D | N252K | | |
| V68A | S103A | V104I | G159D | S212C | A232V | Q236H | Q245R | N248D | N252K | | |
| V68A | S103A | V104I | G159D | S212G | A232V | Q236H | Q245R | N248D | N252K | | |

TABLE X-continued

| | | | | | | | | |
|---|---|---|---|---|---|---|---|---|
| S103A | V104I | G159D | A232V | Q236H | Q245R | N248D | N252K | |
| V68A | S103A | V104I | G159D | Y209W | A232V | Q236H | Q245R | N248D N252K |
| V68A | S103A | V104I | Q109R | G159D | A232V | Q236H | Q245R | N248D N252K |
| G20R | V68A | S103A | V104I | G159D | A232V | Q236H | Q245R | N248D N252K |
| V68A | S103A | V104I | G159D | Y209F | A232V | Q236H | Q245R | N248D N252K |
| N76D | S103A | V104I | G159D | Y192F | A232V | Q236H | Q245R | |
| N76D | S103A | V104I | V147I | G159D | A232V | Q236H | Q245R | N248S K251R |
| Q12R | V68A | N76D | S103A | V104I | G159D | A232V | Q236H | Q245R A272S |
| V68A | N76D | S103A | V104I | G159D | N183K | Q206L | A232V | Q236H Q245R |
| V68A | N76D | S103A | V104I | G159D | A232V | Q236H | Q245R | S256R |
| V68A | N76D | S103A | V104I | G159D | Q206R | A232V | Q236H | Q245R |
| K27R | V68A | N76D | S103A | V104I | G159D | A232V | Q236H | Q245R |
| Q12R | A48V | V68A | N76D | S103A | V104I | G159D | A232V | Q236H Q245R |
| V68A | N76D | S103A | V104I | G159D | A232V | Q236H | Q245R | N261W |
| V68A | N76D | S103A | V104I | G159D | G211R | A232V | Q236H | Q245R |
| V68A | N76D | S103A | V104I | G159D | G211V | A232V | Q236H | Q245R |
| Q12R | V68A | N76D | S103A | V104I | G159D | Y214L | A232V | Q236H Q245R |
| V68A | N76D | S103A | V104I | G159D | A215R | A232V | Q236H | Q245R |
| Q12R | V68A | N76D | S103A | V104I | G159D | A232V | Q236H | Q245R |
| G20R | V68A | N76D | S103A | V104I | G159D | A232V | Q236H | Q245R S259G |
| V68A | N76D | S87R | S103A | V104I | G159D | A232V | Q236H | Q245R I260V |
| N76D | S103A | V104I | G159D | A232V | Q236H | Q245R | L257V | |
| V68A | N76D | S103A | V104I | G159D | T213R | A232V | Q236H | Q245R T260A |
| V68A | N76D | S103A | V104I | G159D | P210R | A232V | Q236H | Q245R |
| V68A | S103A | V104I | G159D | S212P | A232V | Q236H | Q245R | N248D N252K |
| V68A | S103A | V104I | G159D | T224A | A232V | Q236H | Q245R | L257V |
| V68A | S103A | V104I | G159D | A232V | Q236H | Q245R | N252S | |
| V68A | S103A | V104I | G159D | A232V | Q236H | Q245R | N252K | |
| V68A | S103A | V104I | G159D | A232V | Q236H | Q245R | N248D | N252K |
| V68A | S103A | V104I | G159D | A232V | Q236H | Q245R | | |
| V68A | S103A | V104I | N140D | G159D | A232V | Q236H | Q245R | N252K |
| N43S | V68A | S103A | V104I | G159D | A232V | Q236H | Q245R | N252K |
| N43K | V68A | S103A | V104I | G159D | A232V | Q236H | Q245R | |
| N43D | V68A | S103A | V104I | G159D | A232V | Q236H | Q245R | N252K |
| V68A | S103A | V104I | G159D | A232V | Q236H | Q245R | L257V | |

A highly preferred protease variant useful in the cleaning compositions of the present invention include a substitution set selected from the group consisting of:

12/102/103/104/159/212/232/236/245/248/252; 61/68/103/104/159/232/236/245/248/252;

62/103/104/130/159/213/232/236/245/248/252; 62/103/104/159/213/232/236/245/248/252;

62/103/104/109/159/213/232/236/245/248/252; 62/103/104/159/232/236/245/248/252;

62/101/103/104/159/212/213/232/236/245/248/252;

68/103/104/159/232/236/245/248/252/270;

68/103/104/159/185/232/236/245/248/252; 68/103/104/159/210/232/236/245/248/252;

68/103/104/159/185/210/232/236/245/248/152; 68/103/104/159/213/232/236/245/248/252;

68/103/104/159/230/232/236/245; 68/76/103/104/159/209/232/236/245;

68/103/104/232/236/245/248/257/275; 68/103/104/213/232/236/245/248/252;

68/103/104/159/232/236/245/248/252; 68/103/104/159/209/232/236/245;

68/76/103/104/159/232/236/245; 68/103/104/159232/236/245/252;

68/103/104/159/232/236/245; 68/103/104/159/232/236/245/257;

68/76/103/104/159/211/232/236/245; 68/76/103/104/159/215/232/236/245;

68/103/104/159/210/232/236/245; 68/103/104/159/213/232/236/245/260;

68/76/103/104/159/213/232/236/245/260; 68/76/103/104/159/210/232/236/245/260;

68/103/104/159/183/232/236/245/248/252; 68/103/104/232/236/245/257/275;

68/103/104/159/213/232/236/245; 76/103/104/159/232/236/245;

76/103/104/159/213/232/236/245/260; 76/103/104/131/159/232/236/245/248/252;

97/103/104/159/232/236/245/248/252; 98/103/104/159/232/236/245/248/252;

98/102/103/104/159/212/232/236/245/248/252; 101/103/104/159/232/236/245/248/252;

102/103/104/159/232/236/245/248/252; 103/104/159/232/236/245;

103/104/159/248/252/270; 103/104/159/232/236/245/248/252;

103/104/159/205/209/232/236/245/257 103/104/159/232/245/248/252;

103/104/159/205/209/210/232/236/245/257; 103/104/159/213/232/236/245/248/252;

103/104/159/217/232/236/245/248/252; 103/104/130/159/232/236/245/248/252;

103/104/131/159/232/236/245/248/252; 103/104/159/205/209/232/236/245; and

103/104/159/232/236/245/257.

A more highly preferred protease variant useful in the cleaning compositions of the present invention include a substitution set selected from the group consisting of:

12R/102A/103A/104I/159D/212G/232V/236H/245R/248D/252K;

61E/68A/103A/104I/159D/232V/236H/245R/248D/252K;

62D/103A/104I/109R/159D/213R/232V/236H/245R/248D/252K;

62D/103A/104I/159D/213R/232V/236H/245R/248D/252K;
62D/103A/104I/159D/232V/236H/245R/248D/252K;
62D/103A/104I/130G/159D/213R/232V/236H/245R/248D/252K;
62D/101G/103A/104I/159D/212G/213R/232V/236H/245R/248D/252K;
68A/76D/103A/104I/159D/213R/232V/236H/245R/260A;
68A/76D/103A/104I/159D/210I/232V/236H/245R/260A;
68A/103A/104I/159D/183D/232V/236H/245R/248D/252K;
68A/103A/104I/159D/209W/232V/236H/245R;
68A/76D/103A/104I/159D/211R/232V/236H/245R;
68A/76D/103A/104I/159D/215R/232V/236H/245R;
68A/103A/104I/159D/213R/232V/236H/245R/260A;
68A/76D/103A/104I/159D/232V/236H/245R;
68A/103A/104I/159D/232V/236H/245R/252K;
68A/103A/104I/159D/232V/236H/245R;
68A/103A/104I/159D/232V/236H/245R/257V;
68A/103A/104I/159D/185D/232V/236H/245R/248D/252K;
68A/103A/104I/159D/210L/232V/236H/245R/248D/252K;
68A/103A/104I/159D/185D/210L/232V/236H/245R/248D/252K;
68A/103A/104I/159D/213E/232V/236H/245R/248D/252K;
68A/103A/104I/159D/230V/232V/236H/245R;
68A/76D/103A/104I/159D/209W/232V/236H/245R;
68A/103A/104I/232V/236H/245R/248D/257V/275H;
68A/103A/104I/232V/236H/245R/257V/275H;
68A/103A/104I/213E/232V/236H/245R/248D/252K;
68A/103A/104I/159D/232V/236H/245R/248D/252K;
68A/103A/104I/159D/210I/232V/236R/245R;
68A/103A/104I/159D/210L/232V/236H/245R;
68A/103A/104I/159D/213G/232V/236H/245R;
68A/103A/104I/159D/232V/236H/245R/248D/252K/270A;
76D/103A/104I/159D/232V/236H/245R;
76D/103A/104I/131V/159D/232V/236H/245R/248D/252K;
76D/103A/104I/159D/213R/232V/236H/245R/260A;
97E/103A/104I/159D/232V/236H/245R/248D/252K;
98L/103A/104I/159D/232V/236H/245R/248D/252K;
98L/102A/103A/104I/159D/212G/232V/236H/245R/248D/252K;
101G/103A/104I/159D/232V/236H/245R/248D/252K;
102A/103A/104I/159D/232V/236H/245R/248D/252K;
103A/104I/159D/232V/236H/245R/248D/252K;
103A/104I/159D/213R/232V/236H/245R/248D/252K;
103A/104I/130G/159D/232V/236H/245R/248D/252K;
103A/104I/159D/217E/232V/236H/245R/248D/252K;
103A/104I/159D/248D/252K/270V;
103A/104I/159D/232V/236H/245R;
103A/104I/159D/205I/209W/232V/236H/245R;
103A/104I/159D/232V/236H/245R/257V;
103A/104I/159D/205I/209W/232V/236H/245R/257V;
103A/104I/131V/159D/232V/236H/245R/248D/252K;
103A/104I/159D/205I/209W/210I/232V/236H/245R/257V; and
103A/104I/159D/232V/245R/248D/252K.

Recombinant Proteases/Recombinant Subtilisins

A "recombinant protease" or "recombinant subtilisin" refers to a protease or subtilisin in which the DNA sequence encoding the naturally-occurring protease or subtilisin, respectively, is modified to produce a mutant DNA sequence which encodes the substitution, insertion or deletion of one or more amino acids in the protease or subtilisin amino acid sequence. Suitable modification methods are disclosed herein, and in U.S. Pat. Nos. RE 34,606, 5,204,015 and 5,185,258.

Non-Human Proteases/Non-Human Subtilisins

"Non-human proteases" or "non-human subtilisins" and the DNA encoding them may be obtained from many procaryotic and eucaryotic organisms. Suitable examples of procaryotic organisms include gram negative organisms such as E. coli or Pseudomonas and gram positive bacteria such as Micrococcus or Bacillus. Examples of eucaryotic organisms from which carbonyl hydrolase and their genes may be obtained include yeast such as *Saccharomyces cerevisiae*, fungi such as Aspergillus sp. and non-human mammalian sources such as, for example, bovine sp. from which the gene encoding the protease chymosin or subtilisin chymosin can be obtained. A series of proteases and/or subtilisins can be obtained from various related species which have amino acid sequences which are not entirely homologous between the members of that series but which nevertheless exhibit the same or similar type of biological activity. Thus, non-human protease or non-human subtilisin as used herein have a functional definition which refers to proteases or subtilisins, respectively, which are associated, directly or indirectly, with procaryotic and eucaryotic sources.

Variant DNA Sequences

Variant DNA sequences encoding such protease or subtilisin variants are derived from a precursor DNA sequence which encodes a naturally-occurring or recombinant precursor enzyme.

In a preferred embodiment of the present invention, the variant DNA sequences are derived by modifying the precursor DNA sequence to encode the substitution, insertion or deletion of one or more specific amino acid residues encoded by the precursor DNA sequence corresponding to positions 103 in combination with one or more of the following positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of *Bacillus amyloliquefaciens* subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 of *Bacillus amyloliquefaciens* subtilisin. More preferably, these variant DNA sequences encode the protease variants described herein.

In another preferred embodiment, these variant DNA sequences encode the substitution, insertion or deletion of one or more of the amino acid residues corresponding to positions 62, 212, 230, 232, 252 and 257 of *Bacillus amyloliquefaciens* subtilisin. More preferably, these variant DNA sequences encode the protease variants described herein.

Figure 3:
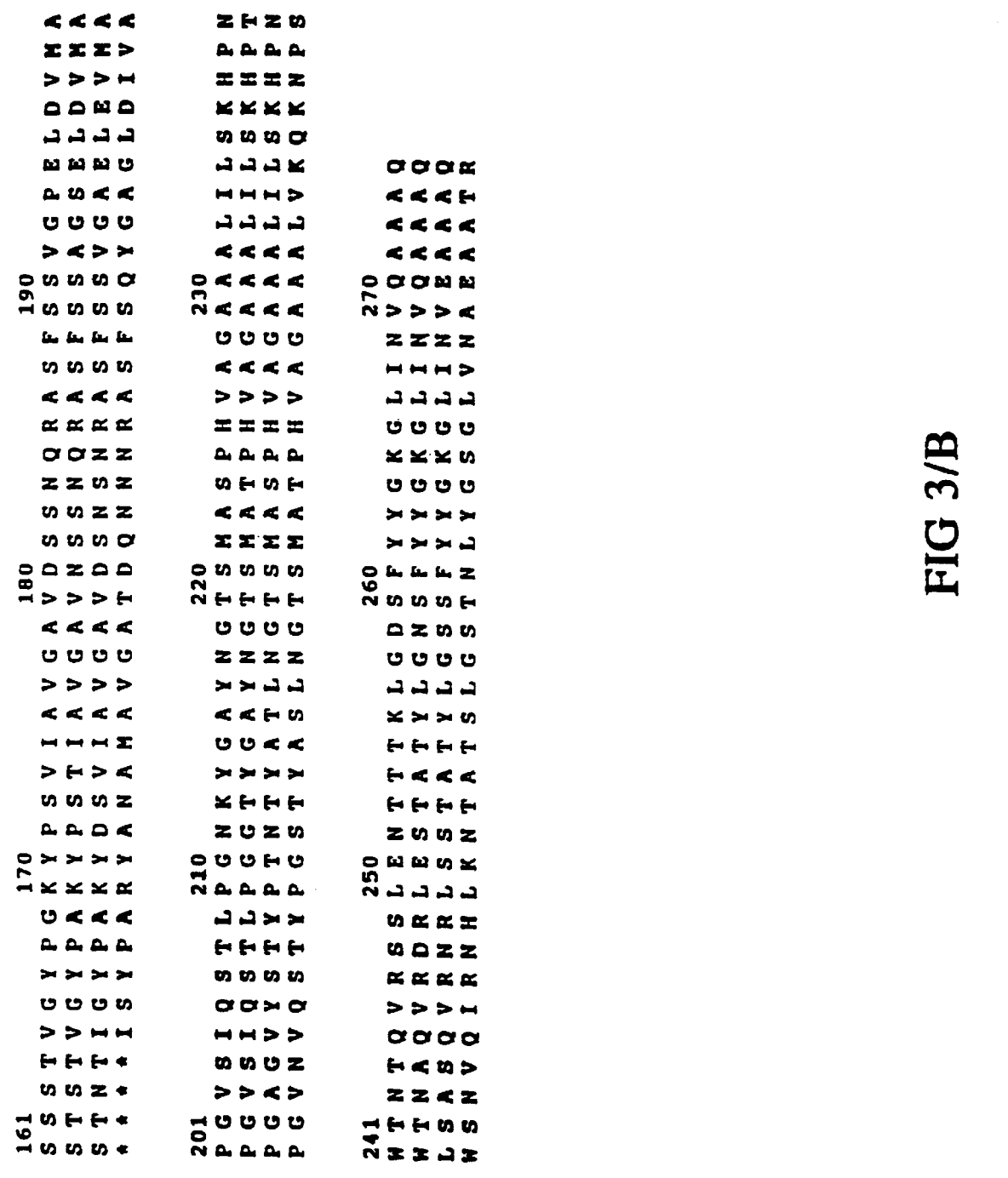

Although the amino acid residues identified for modification herein are identified according to the numbering applicable to *B. amyloliquefaciens* (which has become the conventional method for identifying residue positions in all subtilisins), the preferred precursor DNA sequences useful for the present invention is the DNA sequence of *Bacillus lentus* as shown in FIG. 3.

These recombinant DNA sequences encode protease variants having a novel amino acid sequence and, in general, at least one property which is substantially different from the same property of the enzyme encoded by the precursor protease DNA sequence. Such properties include proteolytic activity, substrate specificity, stability, altered pH profile and/or enhanced performance characteristics.

Specific substitutions corresponding to positions 103 in combination with one or more of the following positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of *Bacillus amyloliquefaciens* subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 wherein the numbered positions correspond to the naturally-occurring subtilisin from *Bacillus amyloliquefaciens* or to equivalent amino acid residues in other carbonyl hydrolases or subtilisins (such as *Bacillus lentus* subtilisin) are described herein. Further, specific substitutions corresponding to one or more of the following positions 62, 212, 230, 232, 252 and 257 wherein the numbered positions correspond to the naturally-occurring subtilisin from *Bacillus amyloliquefaciens* or to equivalent amino acid residues in other carbonyl hydrolases or subtilisins (such as *Bacillus lentus* subtilisin) are described herein. These amino acid position numbers refer to those assigned to the mature *Bacillus amyloliquefaciens* subtilisin sequence presented in FIG. 1. The present invention, however, is not limited to the use of mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is *Bacillus lentus* subtilisin and the substitutions, deletions or insertions are made at the equivalent amino acid residue in *B. lentus* corresponding to those listed above.

A residue (amino acid) of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react or interact chemically).

In order to establish homology to primary structure, the amino acid sequence of a precursor protease is directly compared to the *Bacillus amyloliquefaciens* subtilisin primary sequence and particularly to a set of residues known to be invariant in subtilisins for which sequence is known. For example, FIG. 2 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, in FIG. 3 the amino acid sequence of subtilisin from *Bacillus amyloliquefaciens*, *Bacillus subtilis*, *Bacillus licheniformis* (carlsbergensis) and *Bacillus lentus* are aligned to provide the maximum amount of homology between amino acid sequences. A comparison of these sequences shows that there are a number of conserved residues contained in each sequence. These conserved residues (as between BPN' and *B. lentus*) are identified in FIG. 2.

These conserved residues, thus, may be used to define the corresponding equivalent amino acid residues of *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletion in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*. Thus, for example, the amino acid at position +76 is asparagine (N) in both *B. amyloliquefaciens* and *B. lentus* subtilisins. In the protease variants of the invention, however, the amino acid equivalent to +76 in *Bacillus amyloliquefaciens* subtilisin is substituted with aspartate (D). The abbreviations and one letter codes for all amino acids in the present invention conform to the Patentin User Manual (GenBank, Mountain View, Calif.) 1990, p. 101.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protease in question to the *Bacillus amyloliquefaciens* subtilisin. The best model is the crystallographic model giving the lowest R factor for experimental diffraction data at the highest resolution available.

$$R \text{ factor} = \frac{\Sigma_h |Fo(h)| - |Fc(h)|}{\Sigma_h |Fo(h)|}$$

Equivalent residues which are functionally analogues to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two fo the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in natural-occurring sequence. The protease variants of the present invention include the mature forms of protease variants, as well as the pro- and pre-pro-forms of such protease variants. The prepro-forms are the preferred construction since this facilitates the expression, secretion and maturation of the protease variants.

"Prosequence" refers to a sequence of amino acids bound to the N-terminal portion of the mature form of a protease which when removed results in the appearance of the "mature" form of the protease. Many proteolytic enzymes are found in nature as translational proenzyme products and, in the absence of post-translational processing, are expressed in this fashion. A preferred prosequence for producing protease variants is the putative prosequence of *Bacillus amyloliquefaciens* subtilisin, although other protease prosequences may be used.

A "signal sequence" or "presequence" refers to any sequence of amino acids bound to the N'terminal portion of a protease or to the N-terminal portion of a proprotease which may participate in the secretion of the mature or pro forms of the protease. This definition of signal sequence is a functional one, meant to include all those amino sequences encoded by the N-terminal portion of the protease gene which participate in the effectuation of the secretion of protease under native conditions. The present invention utilizes such sequences to effect the secretion of the protease variants as defined here. One possible signal sequence comprises the first seven amino acid residues of the signal sequence from *Bacillus subtilis* subtilisin fused to the remainder of the signal sequence of the subtilisin from *Bacillus lentus* (ATCC 21536).

A "prepro" form of a protease variant consists of the mature form of the protease having a prosequence operably linked to the amino terminus of the protease and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently or the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. RE 34,606 to render them incapable of secreting enzymatically active endoprotease. A preferred host cell for expressing protease is the Bacillus strain BG2036 which is deficient in enzymatically active neutral protease and alkaline protease (subtilisin). The construction of strain BG2036 is described in detail in U.S. Pat. No. 5,264,366. Other host cells for expressing protease include *Bacillus subtilis* 168 (also described in U.S. Pat. No. RE 34,606 and U.S. Pat. No. 5,264,366, the disclosure of which are incorporated herein by reference), as well as any suitable Bacillus strain such as *B. licheniformis, B. lentus,* etc.).

Host cells are transformed or transfected with vectors constructed using recombinant DNA techniques. Such transformed host cells are capable of either replicating vectors encoding the protease variants or expressing the desired protease variant. In the case of vectors which encode the pre- or prepro-form of the protease variant, such variants, when expressed, are typically secreted from the host cell in to the host cell medium.

"Operably linked," when describing the relationship between two DNA regions, simply means that they are functionally related to each other. For example, a prosequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protease may be obtained in accord with the general methods known to those skilled in the art. The methods generally comprise synthesizing labeled probes having putative sequences encoding regions of the protease of interest, preparing genomic libraries from organisms expressing the protease, and screening the libraries for the gene of interest by hybridization to the probes. Positively hybridizing clones are then mapped and sequenced.

The cloned protease is then used to transform a host cell in order to express the protease. The protease gene is then ligated into a high copy number plasmid. This plasmid replicates in hosts in the sense that it contains the well-known elements necessary for plasmid replication: a promote operably linked to the gene in question (which may be supplied as the gene's own homologous promoter if it is recognized, i.e. transcribed by the host), a transcription termination and polyadenylation region (necessary for stability of the mRNA transcribed by the host from the protease gene in certain eucaryotic host cells) which is exogenous or is supplied by the endogenous terminator region of the protease gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitation. However, it is within the scope herein to integrate multiple copies of the protease gene into host genome. This is facilitated by procaryotic and eucaryotic organisms which are particularly susceptible to homologous recombination. The gene can be a natural *B. lentus* gene. Alternatively, a synthetic gene encoding a naturally-occurring or mutant precursor protease may be produced. In such an approach, the DNA and/or amino acid sequence of the precursor protease is determined. Multiple, overlapping synthetic single-stranded DNA fragments are thereafter synthesized, which upon hybridization and ligation produce a synthetic DNA enclding the precursor protease. An example of synthetic gene construction is set forth in Example 3 of U.S. Pat. No. 5,204,105, the disclosure of which is incorporated herein by reference.

Once the naturally-occurring or synthetic precursor protease gene has been cloned, a number of modifications are undertaken to enhance the use of the gene beyond synthesis of the naturally-occurring precursor protease. Such modifications include the production of recombinant proteases as disclosed in U.S. Pat. No. RE 34,606 and EPO Publication No. 0 251 446 and the production of protease variants described herein.

The following cassette mutagenesis method may be used to facilitate the construction of the proteases variants of the present invention, although other methods may be used. First, the naturally-occurring gene encoding the protease is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which, when expressed will encode various mutants. Such restriction sites are preferably unique sites within the protease gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site if available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites. As used herein, proteolytic activity is defined as the rate of hydrolysis of peptide bonds per milligram of active enzyme. Many well known procedures exist for measuring proteolytic activity (K. M. Kalisz, "Microbial Proteinases," *Advances in Biochemical Engineering/Biotechnology*, A. Fiechter ed., 1988). In addition to or as an alternative to modified proteolytic activity, the variant enzymes of the present invention may have other modified properties such as $K_m$, $k_{cat}$, $k_{cat}/K_m$ ratio and/or modified substrate specifically and/or modified pH activity profile. These enzymes can be tailored for the particular substrate which is anticipated to be present, for example, in the preparation of peptides or for hydrolytic processes such as laundry uses.

In one aspect of the invention, the objective is to secure a variant protease having altered proteolytic activity as compared to the precursor protease, since increasing such activity (numerically larger) enables the use of the enzyme to more efficiently act on a target substrate. Also of interest are variant enzymes having altered thermal stability and/or altered substrate specificity as compared to the precursor. In some instances, lower proteolytic activity may be desirable, for example a decrease in proteolytic activity would be useful where the synthetic activity of the proteases is desired (as for synthesizing peptides). One may wish to decrease this proteolytic activity, which is capable of destroying the product of such synthesis. Conversely, in some instances it may be desirable to increase the proteolytic activity of the variant enzyme versus its precursor. Additionally, increases or decreases (alteration) of the stability of the variant, whether alkaline or thermal stability, may be desirable. Increases or decreases in $k_{cat}$, $K_m$ or $K_{cat}K_m$ are specific to the substrate used to determine these kinetic parameters.

In another aspect of the invention, it has been determined that substitutions at positions corresponding to 103 in combination with one or more of the following positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of *Bacillus amyloliquefaciens* subtilisin are important in modulating overall stability and/or proteolytic activity of the enzyme.

In a further aspect of the invention, it has been determined that substitutions at one or more of the following positions corresponding to positions 62, 212, 230, 232, 252 and 257 of *Bacillus amyloliquefaciens* subtilisin are also important in modulating overall stability and/or proteolytic activity of the enzyme.

These substitutions are preferably made in *Bacillus lentus* (recombinant or native-type) subtilisin, although the substitutions may be made in any Bacillus protease.

Based on the screening results obtained with the variant proteases, the noted mutations in *Bacillus amyloliquefaciens* subtilisin are important to the proteolytic activity, performance and/or stability of these enzymes and the cleaning or wash performance of such variant enzymes.

Methods and procedures for making the enzymes used in the detergent and bleaching compositions of the present invention are known and are disclosed in PCT Publication No. WO 95/10615.

The enzymes of the present invention have trypsin-like specificity. That is, the enzymes of the present invention hydrolyze proteins by preferentially cleaving the peptide bonds of charged amino acid residues, more specifically residues such as arginine and lysine, rather than preferentially cleaving the peptide bonds of hydrophobic amino acid residues, more specifically phenylalanine, tryptophan and tyrosine. Enzymes having the latter profile have a chymotrypsin-like specificity. Substrate specificity as discussed above is illustrated by the action of the enzyme on two synthetic substrates. Protease's having trypsin-like specificity hydrolyze the synthetic substrate bVGR-pNA preferentially over the synthetic substrate sucAAPF-pNA. Chymotrypsin-like protease enzymes, in contrast, hydrolyze the latter much faster than the former. For the purposes of the present invention the following procedure was employed to define the trypsin-like specificity of the protease enzymes of the present invention:

A fixed amount of a glycine buffer at a pH of 10 and a temperature of 25° C. is added to a standard 10 ml test tube. 0.5 ppm of the active enzyme to be tested is added to the test tube. Approximately, 1.25 mg of the synthetic substrate per mL of buffer solution is added to the test tube. The mixture is allowed to incubate for 15 minutes at 25° C. Upon completion of the incubation period, an enzyme inhibitor, PMSF, is added to the mixture at a level of 0.5 mg per mL of buffer solution. The absorbency or OD value of the mixture is read at a 410 nm wavelength. The absorbence then indicates the activity of the enzyme on the synthetic substrate. The greater the absorbence, the higher the level of activity against that substrate.

To then determine the specificity of an individual enzyme, the absorbence on the two synthetic substrate proteins may be converted into a specificity ratio. For the purposes of the present invention, the ratio is determined by the formula specificity of:

[activity on sAAPF-pNA]/[activity on bVGR-pNA]

An enzyme having a ratio of less than about 10, more preferably less than about 5 and most preferably less than about 2.5 may then be considered to demonstrate trypsin-like activity.

Such variants generally have at least one property which is different from the same property of the protease precursor from which the amino acid sequence of the variant is derived.

One aspect of the invention are compositions, such as detergent and bleaching compositions, for the treatment of textiles, dishware, tableware, kitchenware, cookware, and other hard surface substrates that include one or more of the variant proteases of the present invention. Protease-containing compositions can be used to treat for example: silk or wool, as well as other types of fabrics, as described in publications such as RD 216,034, EP 134,267, U.S. Pat. No. 4,533,359, and EP 344,259; and dishware, tableware, kitchenware, cookware, and other hard surface substrates as described in publications such as in U.S. Pat. Nos. 5,478,742, 5,346,822, 5,679,630, and 5,677,272.

II. Bleaching Agents

The bleaching compositions herein contain a bleaching agent, which preferably comprises from about 0.5 to about 20 wt. % of the composition. The bleaching agent is either a substantially insoluble, preferably solid, organic peroxyacid, or a bleaching system comprising a bleach activator and a peroxygen bleaching compound capable of yielding hydrogen peroxide, or a combination of both. The peracid which is in the composition, or which is formed by the combination of activator and peroxygen compound, preferably has a corresponding carboxylic acid that has a Hydrophilic-Lipophilic Balance ("H.L.B.") value which ranges from about 3 to about 6.5. Therefore, a method that can be used to characterize the preferred peroxyacids (from activators or as preformed peroxyacids) which are useful in the present invention is the "H.L.B. Scale" such as that described in Davies, J. T., *Proc 2nd Internat. Congr. Surface Activity* 1, 426, Butterworths, London (1957), incorporated herein by reference. Such an H.L.B. Scale (Hydrophilic-Lipophilic Balance) has been used in the study of surface-active agents (surfactants) as a means to relate the distribution of a surface-active agent between a hydrophilic (water-like) and a lipophilic (oil-like) phase. In this manner, H.L.B. values can be used as an indication of the lipophilic (hydrophobic) character of the active bleaching species in the wash (i.e., the ability of the peroxyacid to partition out of the wash liquor and concentrate at the soil/fabric interface).

Set forth hereinafter in Table A are H.L.B. values which have been calculated for selected peroxyacids (as the corresponding carboxylic acids). The equation used to calculate the H.L.B. values can be set forth as:

HLB=Sum (Hydrophilic Group Numbers)−Sum (Hydrophobic Group Numbers)+7.

The values for the Hydrophilic Group Numbers are [—C(O)OH & —N(H)C(O)—=2.1] and the values for the Hydrophobic Group Numbers are [aliphatic/aromatic carbon= 0.475 & aliphatic carbon atoms between polar groups are ½ the value of an aliphatic carbon in a hydrocarbon chain= (0.475)/2]. For reference, an H.L.B. value >7 indicates that the material is preferentially water soluble and an H.L.B. value <7 indicates increasing surface-activity and hydrophobicity.

Table A

H.L.B. Values Provided by Various Peroxyacids

| Activator/Preformed Peroxyacid | Abbreviation | Peroxyacid | H.L.B. Corresponding Carboxylic Acid |
|---|---|---|---|
| Tetra Acetyl Ethylene Diamine | TAED | $CH_3C(O)OOH$ | 8.6 |
| DiPeroxyDodecane Dioic Acid | DPDDA | $HOO(O)C(CH_2)_{10}C(O)OOH$ | 6.5 |
| Nonyl Amide of Peroxy Succinic Acid | NAPSA | $CH_3(CH_2)_8N(H)—C(O)(CH_2)_2C(O)OOH$ | 6.4 |
| BenzoylOxyBenzene Sulfonate | BOBS | $C_6H_5C(O)OOH$ | 6.3 |
| Nonyl Amide of Peroxy Adipic Acid | NAPAA | $CH_3(CH_2)_8N(H)—C(O)(CH_2)_4C(O)OOH$ | 6.0 |
| NonanoylOxyBenzene Sulfonate | NOBS | $CH_3(CH_2)_7C(O)OOH$ | 5.3 |
| DecanoylOxyBenzene Sulfonate | DOBS | $CH_3(CH_2)_8C(O)OOH$ | 4.8 |
| PerLauric Acid | PLA | $CH_3(CH_2)_{10}C(O)OOH$ | 3.9 |

As noted hereinbefore, a preferred range of H.L.B. values (of the corresponding carboxylic acid) for the peroxyacids of the present invention (whether added directly or generated in situ) ranges from about 3.0 to about 6.5. A more preferred range of H.L.B. values (as the carboxylic acid) for the peroxyacids useful in the present invention (whether added directly or generated in situ) range from about 4.0 to 6.5. The most preferred range of H.L.B. values (as the carboxylic acid) for the peroxyacids of the present invention (whether added directly as generated in situ) ranges from about 4.0 to about 6.0.

(a) Peroxyacid

The present invention encompasses detergent compositions comprising an effective amount of the protease enzyme and a bleaching system comprising at least about 0.1%, preferably from about 0.1% to about 50%, by weight, of a substantially insoluble organic peroxyacid. The peroxyacid useful herein preferably comprises from about 0.5 to about 20, more preferably from about 1 to about 10, most preferably from about 2 to about 7, wt. % of the composition.

Preferred organic peroxyacids are selected from the group consisting of 4-nonylamino-4-oxoperoxybutyric acid; 6-(nonyl-amino)-6-oxoperoxycaproic acid; 1,12-diperoxydodecanedioic acid; heptyl sulfonylperpropionic acid; decylsulphonyl perpropionic acid; and heptyl-, octyl-, nonyl-, decyl-sulphonylperbutyric acid; and mixtures thereof.

Of the organic peroxyacids, amidoperoxyacids (amide substituted peroxycarboxylic acids) are preferred. Suitable amidoperoxyacids for use herein are described in U.S. Pat. Nos. 4,634,551 and 4,686,063, both Burns et al., issued Jan. 6, 1987 and Aug. 11, 1987, respectively, both incorporated herein by reference. Suitable amidoperoxyacids are of the formula:

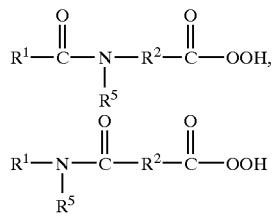

wherein $R^1$ is an alkyl, aryl, or alkaryl group containing from about 1 to about 14 carbon atoms (preferably $R^1$ is an alkyl group containing from about 6 to about 12 carbon atoms), $R^2$ is an alkylene, arylene or alkarylene group containing from about 1 to about 14 carbon atoms (preferably $R^2$ is an alkylene group containing from about 1 to about 6 carbon atoms), and $R^5$ is H or an alkyl, aryl, or alkaryl group containing from about 1 to about 10 carbon atoms (preferably $R^5$ is H). More preferably, $R^1$ is an alkyl group containing from about 8 to about 10 carbon atoms, and $R^2$ is an alkylene group containing from about 2 to about 4 carbon atoms.

Another preferred preformed peracid includes E-phthalimido-peroxycaproic acid ("PAP"). See for example U.S. Pat. Nos. 5,487,818, 5,310,934, 5,246,620, 5,279,757 and 5,132,431.

Other suitable peroxycaproic acids include, but are not limited to, N,N'-terephthaloyl-di-(6-amino-peroxycaproic acid) ("TPCAP") and others described in U.S. Pat. No. 5,770,551. Additionally, N-nonanoyl-6-amino peroxycaproic acid ("NAPCA") can also be used as a peracid. See U.S. Pat. Nos. 5,523,434, 4,634,551 and 4,852,989.

Also suitable for use herein are peroxyfumarates, which are described in U.S. Pat. No. 4,852,989, Burns et al., issued Aug. 1, 1989, incorporated herein by reference, and sulfone peroxyacids (sulfone peroxycarboxylic acids), which are described in U.S. Pat. Nos. 4,758,369, 4,824,591, and 5,004,558, all Dryoff et al., issued Jul. 19, 1988, Apr. 25, 1989, and Apr. 2, 1991, respectively, all incorporated herein by reference.

Example I of U.S. Pat. No. 4,686,063 contains one description of the synthesis of NAPSA, from column 8, line 40 to column 9, line 5, and NAPAA, from column 9, line 15 to column 9, line 65. At the end of the amidoperoxyacid synthesis, the reaction is quenched with water, filtered, washed with water to remove some excess sulfuric acid (or other strong acid with which the peroxyacid was made), and filtered again.

The amidoperoxyacid wet cake thus obtained can be contacted with a phosphate buffer solution at a pH between about 3.5 and 6, preferably between about 4 and 5, according to U.S. Pat. No. 4,909,953, Sadlowski et al., issued Mar. 20, 1990, which is incorporated herein by reference.

Other agents for storage stabilization or exotherm control can be added to the amidoperoxyacid before incorporation into the final product. For example, boric acid, an exotherm control agent disclosed in U.S. Pat. No. 4,686,063, Burns, issued Aug. 11, 1987 and incorporated herein, can be mixed with the amidoperoxyacid (which has been washed in phosphate buffer) in about a 2:1 peracid:boric acid ratio. The phosphate buffer washed amidoperoxyacid can also be mixed with appropriate amounts of dipicolinic acid and tetrasodium pyrophosphate, a chelating stabilization system. Chelants can optionally be included in the phosphate buffer before contact with the wet cake.

The wet cake is preferably made up of particles with an average particle diameter of from about 0.1 to about 260 microns, preferably from about 10 to about 100 microns, and most preferably from about 30 to about 60 microns. Small particle size NAPAA crystals are desired herein. See U.S. Pat. No. 5,055,218, Getty et al., issued Oct. 8, 1991, which is incorporated herein by reference.

NAPAA filter cake herein is preferably washed twice in phosphate buffer. It has been found that two successive phosphate buffer washes lend optimal stability to NAPAA.

Particulate (solid), organic peroxyacids with a theoretical AvO (available oxygen) of between about 3 and about 12, most preferably between 5 and 7, are preferred.

Most preferred for use herein is NAPAA. Another name for the nonylamide of peroxyadipic acid ("NAPAA") is 6-(nonylamino)-6-oxoperoxycaproic acid. The chemical formula for NAPAA is:

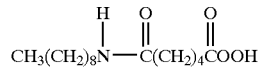

The molecular weight of NAPAA is 287.4.

Detergent compositions and bleaching compositions containing NAPAA provide extremely effective and efficient surface bleaching of textiles. Stains and/or soils are removed from the textiles. These compositions are particularly effective at removing dingy soils from textiles.

NAPAA's polar amide or substituted amide moiety results in a peroxyacid which has a very low vapor pressure and thus possesses a low odor profile as well as excellent bleaching performance. It is believed that the polarity of the amide group results in a reduction of vapor pressure of the peroxyacid, and an increase in melting point.

NAPAA can be used directly as a bleaching agent. It has a reduced vapor pressure and a good odor profile in laundry applications.

NAPAA can be prepared by, for example, first reacting NAAA (monononyl amide of adipic acid), sulfuric acid, and hydrogen peroxide. The reaction product is quenched by addition to ice water followed by filtration, washing with distilled water, and final suction filtration to recover the wet cake. Washing can be continued until the pH of the filtrate is neutral.

It is also preferred that the NAPAA pH (10% solids in water) be between about 4.2 and 4.8. Surprisingly, this pH results in more thermally stable particles.

(b) Bleaching Systems—Bleach Activator and Peroxygen Bleaching Compound (i) Bleach Activators The bleach activator for the bleaching systems useful herein preferably has the following structure:

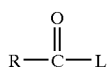

wherein R is an alkyl group containing from about 5 to about 18 carbon atoms wherein the longest linear alkyl chain extending from and including the carbonyl carbon contains from about 6 to about 10 carbon atoms and L is a leaving group, the conjugate acid of which has a pKa in the range of from about 4 to about 13, preferably from about 6 to about 11, most preferably from about 8 to about 11.

L can be essentially any suitable leaving group. A leaving group is any group that is displaced from the bleach activator as a consequence of the nucleophilic attack on the bleach activator by the perhydroxide anion. This, the perhydrolysis reaction, results in the formation of the percarboxylic acid. Generally, for a group to be a suitable leaving group it must exert an electron attracting effect. This facilitates the nucleophilic attach by the perhydroxide anion.

The L group must be sufficiently reactive for the reaction to occur within the optimum time frame (e.g., a wash cycle). However, if L is too reactive, this activator will be difficult to stabilize. These characteristics are generally paralleled by the pKa of the conjugate acid of the leaving group, although exceptions to this convention are known.

Preferred bleach activators are those of the general formula:

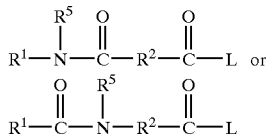

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is selected from the group consisting of:

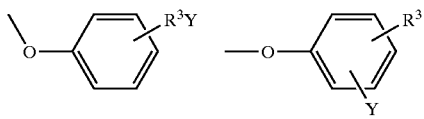

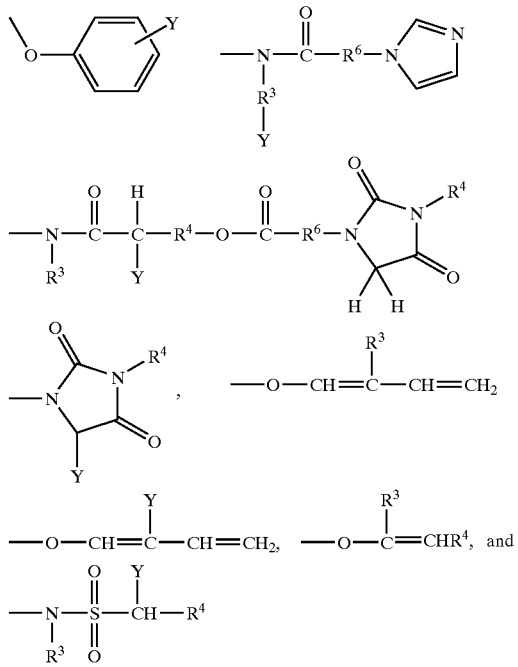

wherein $R^6$ is an alkylene, arylene, or alkarylene group containing from about 1 to about 14 carbon atoms, $R^3$ is an alkyl chain containing from about 1 to about 8 carbon atoms, $R^4$ is H or $R^3$, and Y is H or a solubilizing group. Y is preferably selected from the group consisting of —$SO_3$—M+, —COO—M+, —$SO_4$—M+, (—N+$R'_3$)X— and O←N ($R'_3$), wherein R' is an alkyl chain containing from about 1 to about 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is an anion selected from the group consisting of halide, hydroxide, methylsulfate and acetate anions. More preferably, Y is —$SO_3$—M+ and —COO—M+. It should be noted that bleach activators with a leaving group that does not contain a solubilizing group should be well dispersed in the bleach solution in order to assist in their dissolution. Preferred is:

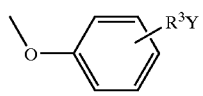

wherein $R^3$ is as defined above and Y is —$SO_3$—M+ or —COO—M+ wherein M is as defined above.

Especially preferred bleach activators are those wherein $R^1$ is a linear alkyl chain containing from about 6 to about 12 carbon atoms, $R^2$ is a linear alkylene chain containing from about 2 to about 6 carbon atoms, $R^5$ is H, and L is selected from the group consisting of:

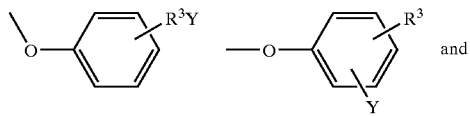

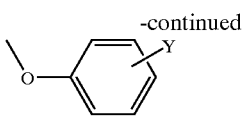

wherein R³ is as defined above, Y is —SO₃—M+ or —COO—M+ and M is as defined above.

A preferred bleach activator is:

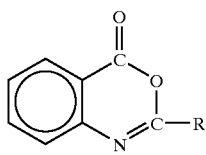

wherein R is H, alkyl, aryl or alkaryl. This is described in U.S. Pat. No. 4,966,723, Hodge et al., incorporated by reference herein.

Preferred bleach activators are:

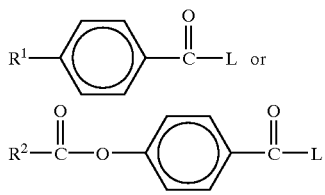

wherein R¹ is H or an alkyl group containing from about 1 to about 6 carbon atoms and R² is an alkyl group containing from about 1 to about 6 carbon atoms and L is as defined above.

Preferred bleach activators are also those of the above general formula wherein L is as defined in the general formula, and R¹ is H or an alkyl group containing from about 1 to about 4 carbon atoms.

Even more preferred are bleach activators of the above general formula wherein L is as defined in the general formula and R¹ is a H.

More preferred bleach activators are those of the above general formula wherein R is a linear alkyl chain containing from about 5 to about 9 and preferably from about 6 to about 8 carbon atoms and L is selected from the group consisting of:

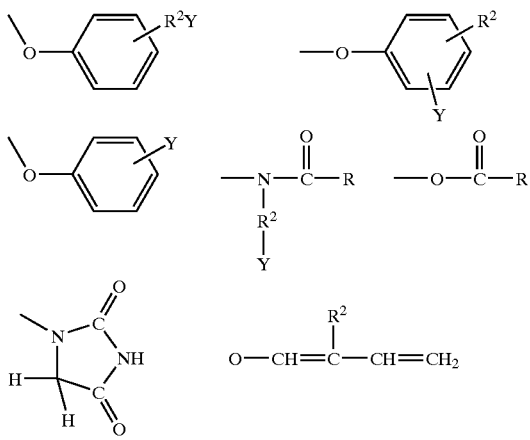

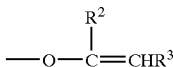

wherein R, R², R³ and Y are as defined above.

Particularly preferred bleach activators are those of the above general formula wherein R is an alkyl group containing from about 5 to about 12 carbon atoms wherein the longest linear portion of the alkyl chain extending from and including the carbonyl carbon is from about 6 to about 10 carbon atoms, and L is selected from the group consisting of:

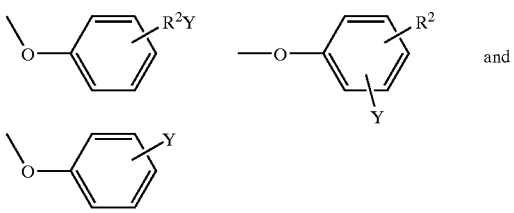

wherein R² is an alkyl chain containing from about 1 to about 8 carbon atoms, and Y is —SO—₃M+ or —COO—M+ wherein M is an alkali metal, ammonium or substituted ammonium cation.

Especially preferred bleach activators are those of the above general formula wherein R is a linear alkyl chain containing from about 5 to about 9 and preferably from about 6 to about 8 carbon atoms and L is selected from the group consisting of:

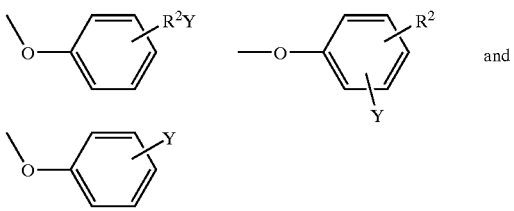

wherein R² is as defined above and Y is —SO—₃M+ or —COO—M+ wherein M is as defined above.

The most preferred bleach activators have the formula:

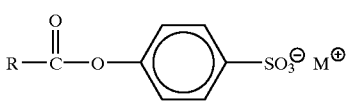

wherein R is a linear alkyl chain containing from about 5 to about 9 and preferably from about 6 to about 8 carbon atoms and M is sodium or potassium.

Preferably, the bleach activator herein is sodium nonanoyloxybenzenesulfonate (NOBS) or sodium benzoyloxybenzenesulfonate (BOBS).

Further particularly preferred for use in the present invention bleaching compositions are the following bleach activators which are particularly safe for use with machines having natural rubber parts. This is believed to be the result of not producing oily diacylperoxide (DAP) species by the perhydrolysis reaction of these amido acid-derived bleach activators, but rather forming insoluble crystalline solid DAP's. These solids are believed to not form a coating film and thus natural rubber parts are not exposed to DAP's for extended periods of time. These preferred bleach activators are members selected from the group consisting of:

a) a bleach activator of the general formula:

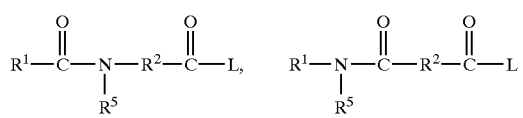

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, or alkaryl group containing from about 1 to about 10 carbon atoms, and L is a leaving group;

b) benzoxazin-type bleach activators of the general formula:

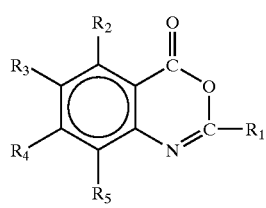

wherein $R_1$ is H, alkyl, alkaryl, aryl, arylalkyl, and wherein $R_2$, $R_3$, $R_4$, and $R_5$ may be the same or different substituents selected from H, halogen, alkyl, alkenyl, aryl, hydroxyl, alkoxyl, amino, alkylamino, $COOR_6$ (wherein $R_6$ is H or an alkyl group) and carbonyl functions;

c) N-acyl caprolactam bleach activators of the formula:

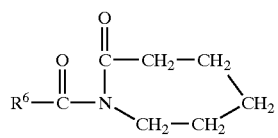

wherein $R^6$ is H or an alkyl, aryl, alkoxyaryl or alkaryl group containing from 1 to 12 carbons; and d) mixtures of a), b) and c).

Preferred bleach activators of type a) are those wherein $R^1$ is an alkyl group containing from about 6 to about 12 carbon atoms, $R^2$ contains from about 1 to about 8 carbon atoms, and $R^5$ is H or methyl. Particularly preferred bleach activators are those of the above general formulas wherein $R^1$ is an alkyl group containing from about 7 to about 10 carbon atoms and $R^2$ contains from about 4 to about 5 carbon atoms.

Preferred bleach activators of type b) are those wherein $R_2$, $R_3$, $R_4$, and $R_5$ are H and $R_1$ is a phenyl group.

The preferred acyl moieties of said N-acyl caprolactam bleach activators of type c) have the formula $R^6$—CO— wherein $R^6$ is H or an alkyl, aryl, alkoxyaryl, or alkaryl group containing from 1 to 12 carbons, preferably from 6 to 12 carbon atoms. In highly preferred embodiments, $R^6$ is a member selected from the group consisting of phenyl, heptyl, octyl, nonyl, 2,4,4-trimethylpentyl, decenyl and mixtures thereof.

Amido Derived Bleach Activators

The bleach activators of type a) employed in the present invention are amide substituted compounds of the general formulas:

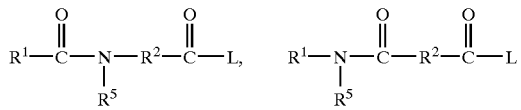

or mixtures thereof, wherein $R^1$, $R^2$ and $R^5$ are as defined above and L can be essentially any suitable leaving group. Preferred bleach activators are those of the above general formula wherein $R^1$, $R^2$ and $R^5$ are as defined for the peroxyacid and L is selected from the group consisting of:

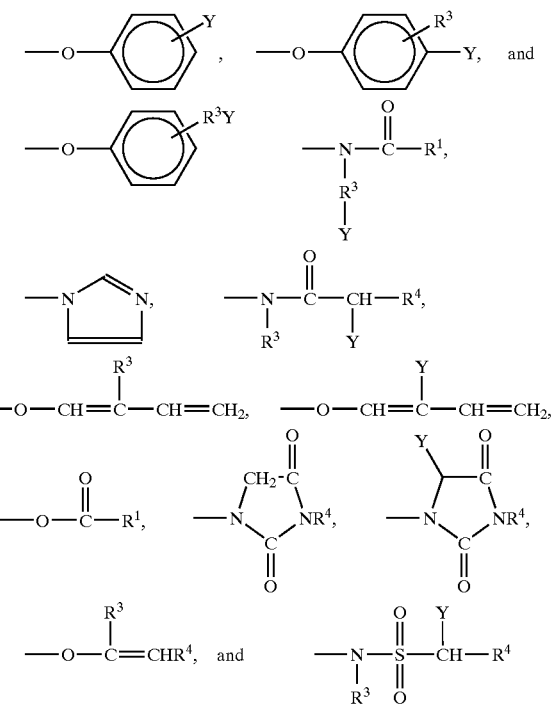

and mixtures thereof, wherein $R^1$ is an alkyl, aryl, or alkaryl group containing from about 1 to about 14 carbon atoms, $R^3$ is an alkyl chain containing from 1 to about 8 carbon atoms, $R^4$ is H or $R^3$, and Y is H or a solubilizing group.

The preferred solubilizing groups are —$SO_3^-M^+$, —$CO_2^-M^+$, —$SO_4^-M^+$, —$N^+(R^3)_4X^-$ and $O<N(R^3)_3$ and most preferably —$SO_3^-M^+$ and —$CO_2^-M^+$ wherein $R^3$ is an alkyl chain containing from about 1 to about 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is a halide, hydroxide, methylsulfate or acetate anion. It should be noted that bleach activators with a leaving group that does not contain a solubilizing groups should be well dispersed in the bleaching solution in order to assist in their dissolution.

Preferred bleach activators are those of the above general formula wherein L is selected from the group consisting of:

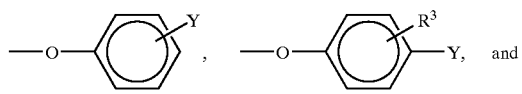

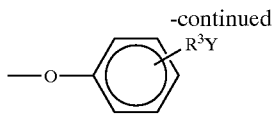

wherein $R^3$ is as defined above and Y is $-SO_3^-M^+$ or $-CO_2^-M^+$ wherein M is as defined above.

Another important class of bleach activators, including those of type b) and type c), provide organic peracids as described herein by ring-opening as a consequence of the nucleophilic attack on the carbonyl carbon of the cyclic ring by the perhydroxide anion. For instance, this ring-opening reaction in type c) activators involves attack at the caprolactam ring carbonyl by hydrogen peroxide or its anion. Since attack of an acyl caprolactam by hydrogen peroxide or its anion occurs preferably at the exocyclic carbonyl, obtaining a significant fraction of ring-opening may require a catalyst. Another example of ring-opening bleach activators can be found in type b) activators, such as those disclosed in U.S. Pat. No. 4,966,723, Hodge et al, issued Oct. 30, 1990.

Benzoxazin-type Bleach Activators

Such activator compounds disclosed by Hodge include the activators of the benzoxazin-type, having the formula:

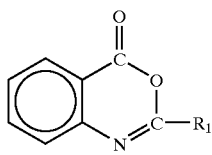

including the substituted benzoxazins of the type

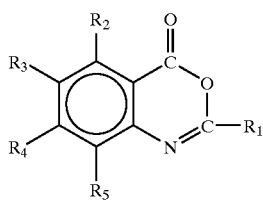

wherein R1 is H, alkyl, alkaryl, aryl, arylalkyl, and wherein R2, R3, R4, and R5 may be the same or different substituents selected from H, halogen, alkyl, alkenyl, aryl, hydroxyl, alkoxyl, amino, alkyl amino, COOR6 (wherein R6 is H or an alkyl group) and carbonyl functions.

A preferred activator of the benzoxazin-type is:

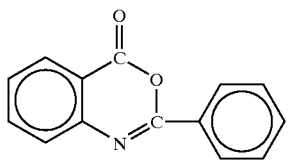

When the activators are used, optimum surface bleaching performance is obtained with washing solutions wherein the pH of such solution is between about 8.5 and 10.5 and preferably between 9.5 and 10.5 in order to facilitate the perhydrolysis reaction. Such pH can be obtained with substances commonly known as buffering agents, which are optional components of the bleaching systems herein.

N-Acyl Caprolactam Bleach Activators

The N-acyl caprolactam bleach activators of type c) employed in the present invention have the formula:

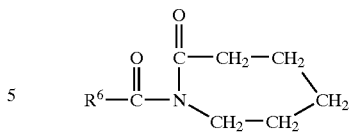

wherein $R^6$ is H or an alkyl, aryl, alkoxyaryl, or alkaryl group containing from 1 to 12 carbons. Caprolactam activators wherein the $R^6$ moiety contains at least about 6, preferably from 6 to about 12, carbon atoms provide hydrophobic bleaching which affords nucleophilic and body soil clean-up, as noted above. Caprolactam activators wherein $R^6$ comprises from 1 to about 6 carbon atoms provide hydrophilic bleaching species which are particularly efficient for bleaching beverage stains. Mixtures of hydrophobic and hydrophilic caprolactams, typically at weight ratios of 1:5 to 5:1, preferably 1:1, can be used herein for mixed stain removal benefits.

Highly preferred N-acyl caprolactams are selected from the group consisting of benzoyl caprolactam, octanoyl caprolactam, nonanoyl caprolactam, 3,5,5-trimethylhexanoyl caprolactam, decanoyl caprolactam, undecenoyl caprolactam, and mixtures thereof. Methods for making N-acyl caprolactams are well known in the art.

Contrary to the teachings of U.S. Pat. No. 4,545,784, the bleach activator is preferably not absorbed onto the peroxygen bleaching compound. To do so in the presence of other organic detersive ingredients could cause safety problems.

The bleach activators of type a), b) or c) will comprise at least about 0.01%, preferably from about 0.1%, more preferably from about 1%, most preferably from about 3% to about 50%, preferably to about 30%, more preferably to about 15%, still more preferably to about 10%, most preferably to about 8% by weight of bleaching system or bleaching composition.

The preferred amido-derived and caprolactam bleach activators herein can also be used in combination with rubber-safe, enzyme-safe, hydrophilic activators such as TAED, typically at weight ratios of amido-derived or caprolactam activators:TAED in the range of 1:5 to 5:1, preferably about 1:1.

Highly preferred bleach activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group.

Additional preferred bleach activators are those described in U.S. Pat. No. 5,698,504 Christie et al., issued Dec. 16, 1997; U.S. Pat. No. 5,695,679 Christie et al. issued Dec. 9, 1997; U.S. Pat. No. 5,686,401 Willey et al., issued Nov. 11, 1997; U.S. Pat. No. 5,686,014 Hartshorn et al., issued Nov. 11, 1997; U.S. Pat. No. 5,405,412 Willey et al., issued Apr. 11, 1995; U.S. Pat. No. 5,405,413 Willey et al., issued Apr. 11, 1995; U.S. Pat. No. 5,130,045 Mitchel et al., issued Jul. 14, 1992; and U.S. Pat. No. 4,412,934 Chung et al., issued Nov. 1, 1983, and copending patent applications U.S. Ser. Nos. 08/709,072, 08/064,564, all of which are incorporated herein by reference.

Preferred hydrophobic bleach activators include, but are not limited to, nonanoyloxybenzenesulphonate (NOBS), 4-[N-(nonaoyl) amino hexanoyloxy]-benzene sulfonate sodium salt (NACA-OBS) an example of which is described in U.S. Pat. No. 5,523,434, dodecanoyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA).

Quaternary substituted bleach activators may also be included. The present cleaning compositions preferably comprise a quaternary substituted bleach activator (QSBA) or a quaternary substituted peracid (QSP); more preferably, the former. Preferred QSBA structures are further described in U.S. Pat. No. 5,686,015 Willey et al., issued Nov. 11, 1997; U.S. Pat. No. 5,654,421 Taylor et al., issued Aug. 5, 1997; U.S. Pat. No. 5,460,747 Gosselink et al., issued Oct. 24, 1995; U.S. Pat. No. 5,584,888 Miracle et al., issued Dec. 17, 1996; and U.S. Pat. No. 5,578,136 Taylor et al., issued Nov. 26, 1996; all of which are incorporated herein by reference.

Highly preferred bleach activators useful herein are amide-substituted as described in U.S. Pat. Nos. 5,698,504, 5,695,679, and 5,686,014 each of which are cited herein above. Preferred examples of such bleach activators include: (6-octanamidocaproyl)oxybenzenesulfonate, (6-nonanamidocaproyl)oxybenzenesulfonate, (6-decanamidocaproyl) oxybenzenesulfonate and mixtures thereof.

Other useful activators, disclosed in U.S. Pat. Nos. 5,698,504, 5,695,679, 5,686,014 each of which is cited herein above and U.S. Pat. No. 4,966,723 Hodge et al., issued Oct. 30, 1990, include benzoxazin-type activators, such as a $C_6H_4$ ring to which is fused in the 1,2-positions a moiety —C(O)OC($R^1$)=N—.

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504, 5,695,679 and 5,686,014, each of which is cited herein above, are very useful herein, especially the acyl caprolactams (see for example WO 94-28102 A) and acyl valerolactams (see U.S. Pat. No. 5,503,639 Willey et al., issued Apr. 2, 1996 incorporated herein by reference).

The bleaching mechanism generally, and the surface bleaching mechanism in particular, are not completely understood. However, it is generally believed that the bleach activator undergoes nucleophilic attack by a perhydroxide anion, which is generated from the hydrogen peroxide evolved by the peroxygen bleach, to form a peroxycarboxylic acid. This reaction is commonly referred to as perhydrolysis.

When the activators are used, optimum surface bleaching performance is obtained with washing solutions wherein the pH of such solution is between about 8.5 and 10.5 and preferably between 9.5 and 10.5 in order to facilitate the perhydrolysis reaction. Such pH can be obtained with substances commonly known as buffering agents, which are optional components of the bleaching systems herein.

(ii) The Peroxygen Bleaching Compound

The peroxygen bleaching systems useful herein are those capable of yielding hydrogen peroxide in an aqueous liquor. These compounds are well known in the art and include hydrogen peroxide and the alkali metal peroxides, organic peroxide bleaching compounds such as urea peroxide, and inorganic persalt bleaching compounds, such as the alkali metal perborates, percarbonates, perphosphates, and the like. Mixtures of two or more such bleaching compounds can also be used, if desired.

Hydrogen peroxide sources are described in detail in the herein incorporated Kirk Othmer's Encyclopedia of Chemical Technology, 4th Ed (1992, John Wiley & Sons), Vol. 4, pp. 271–300 "Bleaching Agents (Survey)", and include the various forms of sodium perborate and sodium percarbonate, including various coated and modified forms.

Preferred peroxygen bleaching compounds include sodium perborate, commercially available in the form of mono-, tri-, and tetra-hydrate, sodium pyrophosphate peroxyhydrate, urea peroxyhydrate, sodium percarbonate, and sodium peroxide. Particularly preferred are sodium perborate tetrahydrate, sodium perborate monohydrate and sodium percarbonate. Percarbonate is especially preferred because it is very stable during storage and yet still dissolves very quickly in the bleaching liquor. It is believed that such rapid dissolution results in the formation of higher levels of percarboxylic acid and, thus, enhanced surface bleaching performance.

Highly preferred percarbonate can be in uncoated or coated form. The average particle size of uncoated percarbonate ranges from about 400 to about 1200 microns, most preferably from about 400 to about 600 microns. If coated percarbonate is used, the preferred coating materials include mixtures of carbonate and sulphate, silicate, borosilicate, or fatty carboxylic acids.

The peroxygen bleaching compound will comprise at least about 0.1%, preferably from about 1% to about 75%, more preferably from about 3% to about 40%, most preferably from about 3% to about 25%, by weight of bleaching system or bleaching composition.

The weight ratio of bleach activator to peroxygen bleaching compound in the bleaching system typically ranges from about 2:1 to 1:5. Preferred ratios range from about 1:1 to about 1:3.

The mole ratio of peroxygen bleaching compound (as AvO) to bleach activator in the present invention generally ranges from at least 1:1, preferably from at least 1.5:1, most preferably from at least 2:1, to about 20:1, preferably to about 10:1, more preferably to about 3:1. Preferably, the bleaching compositions herein comprise from about 0.5 to about 20, most preferably from about 1 to about 10, wt. % of the peroxygen bleaching compound.

The bleach activator/bleaching compound systems herein are useful per se as bleaches. However, such bleaching systems are especially useful in compositions which can comprise various detersive adjuncts such as surfactants, builders and the like.

Bleach Catalysts

The compositions herein may further comprise one or more bleach catalysts. Preferred bleach catalysts are zwitterionic bleach catalysts, which are described in U.S. Pat. Nos. 5,576,282 and 5,817,614 (especially 3-(3,4-dihydroisoquinolinium)propane sulfonate. Other bleach catalysts include cationic bleach catalysts are described in U.S. Pat. Nos. 5,360,569, 5,442,066, 5,478,357, 5,370,826, 5,482,515, 5,550,256, and WO 95/13351, WO 95/13352, and WO 95/13353.

Bleaching Compositions

The bleaching compositions of the present invention also comprise, in addition to one or more protease variants and one or more bleaching agents described hereinbefore, one or more cleaning adjunct materials, preferably compatible with the protease variant(s) and bleaching agent(s). The term "compatible", as used herein, means the bleaching composition materials do not reduce the proteolytic activity of the protease enzyme to such an extent that the protease is not effective as desired during normal use situations. The term "cleaning adjunct materials", as used herein, means any liquid, solid or gaseous material selected for the particular type of bleaching composition desired and the form of the product (e.g., liquid; granule; powder; bar; paste; spray; tablet; gel; foam composition), which materials are also preferably compatible with the protease enzyme(s) and bleaching agent(s) used in the composition. Granular compositions can also be in "compact" form and the liquid compositions can also be in a "concentrated" form.

The specific selection of cleaning adjunct materials are readily made by considering the surface, item or fabric to be cleaned, and the desired form of the composition for the cleaning conditions during use (e.g., through the wash detergent use). Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, perservatives, antioxidants, anti-shrinkage agents, anti-wrinkle agents, germicides, fungicides, color speckles, silvercare, antitarnish and/or anti-corrosion agents, alkalinity sources, solubilizing agents, carriers, processing aids, pigments and pH control agents as described in U.S. Pat. Nos. 5,705,464, 5,710,115, 5,698,504, 5,695,679, 5,686,014 and 5,646,101. Specific bleaching composition materials are exemplified in detail hereinafter.

If the cleaning adjunct materials are not compatible with the protease variant(s) in the bleaching compositions, then suitable methods of keeping the cleaning adjunct materials and the protease variant(s) separate (not in contact with each other) until combination of the two components is appropriate can be used. Suitable methods can be any method known in the art, such as gelcaps, encapulation, tablets, physical separation, etc.

Preferably, an effective amount of one or more protease variants described above are included in compositions useful for cleaning a variety of surfaces in need of proteinaceous stain removal. Such bleaching compositions include detergent compositions for cleaning hard surfaces, unlimited in form (e.g., liquid, granular, paste, foam, spray, etc.); detergent compositions for cleaning fabrics, unlimited in form (e.g., granular, liquid, bar formulations, etc.); dishwashing compositions (unlimited in form and including both granular and liquid automatic dishwashing); oral bleaching compositions, unlimited in form (e.g., dentifrice, toothpaste and mouthwash formulations); and denture bleaching compositions, unlimited in form (e.g., liquid, tablet).

The fabric bleaching compositions of the present invention are mainly intended to be used in the wash cycle of a washing machine; however, other uses can be contemplated, such as pretreatment product for heavily-soiled fabrics, or soaking product; the use is not necessarily limited to the washing-machine context, and the compositions of the present invention can be used alone or in combination with compatible handwash compositions.

As used herein, "effective amount of protease variant" refers to the quantity of protease variant described hereinbefore necessary to achieve the enzymatic activity necessary in the specific bleaching composition. Such effective amounts are readily ascertained by one of ordinary skill in the art and is based on many factors, such as the particular variant used, the cleaning application, the specific composition of the bleaching composition, and whether a liquid or dry (e.g., granular, bar) composition is required, and the like.

Preferably the bleaching compositions comprise from about 0.0001% to about 10% of one or more protease variants of the present invention, more preferably from about 0.001% to about 1%, more preferably still from about 0.001% to about 0.1%. Also preferably the protease variant of the present invention is present in the compositions in an amount sufficient to provide a ratio of mg of active protease per 100 grams of composition to ppm theoretical Available $O_2$ ("$AvO_2$") from any peroxyacid in the wash liquor, referred to herein as the Enzyme to Bleach ratio (E/B ratio), ranging from about 1:1 to about 20:1. Several examples of various bleaching compositions wherein the protease variants of the present invention may be employed are discussed in further detail below. Also, the bleaching compositions may include from about 1% to about 99.9% by weight of the composition of the cleaning adjunct materials.

As used herein, "non-fabric bleaching compositions" include hard surface bleaching compositions, dishwashing compositions, oral bleaching compositions, denture bleaching compositions and personal cleansing compositions.

When the bleaching compositions of the present invention are formulated as compositions suitable for use in a laundry machine washing method, the compositions of the present invention preferably contain both a surfactant and a builder compound and additionally one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional cleaning adjunct materials.

The compositions of the present invention can also be used as detergent additive products in solid or liquid form. Such additive products are intended to supplement or boost the performance of conventional detergent compositions and can be added at any stage of the cleaning process.

When formulated as compositions for use in manual dishwashing methods the compositions of the invention preferably contain a surfactant and preferably other cleaning adjunct materials selected from organic polymeric compounds, suds enhancing agents, group II metal ions, solvents, hydrotropes and additional enzymes.

If needed the density of the laundry detergent compositions herein ranges from 400 to 1200 g/liter, preferably 500 to 950 g/liter of composition measured at 20° C.

The "compact" form of the bleaching compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulfates and chlorides. A preferred filler salt is sodium sulfate.

Liquid bleaching compositions according to the present invention can also be in a "concentrated form", in such case, the liquid bleaching compositions according the present invention will contain a lower amount of water, compared to conventional liquid detergents. Typically the water content of the concentrated liquid bleaching composition is preferably less than 40%, more preferably less than 30%, most preferably less than 20% by weight of the bleaching composition.

Cleaning Adjunct Materials

Surfactant System

Detersive surfactants included in the fully-formulated bleaching compositions afforded by the present invention comprises at least 0.01%, preferably at least about 0.1%, more preferably at least about 0.5%, most preferably at least about 1% to about 60%, more preferably to about 35%, most preferably to about 30% by weight of bleaching composition depending upon the particular surfactants used and the desired effects.

The detersive surfactant can be nonionic, anionic, ampholytic, zwitterionic, cationic, semi-polar nonionic, and mixtures thereof, nonlimiting examples of which are disclosed in U.S. Pat. Nos. 5,707,950 and 5,576,282. Preferred detergent and bleaching compositions comprise anionic detersive surfactants or mixtures of anionic surfactants with other surfactants, especially nonionic surfactants.

Nonlimiting examples of surfactants useful herein include the conventional $C_{11}$–$C_{18}$ alkyl benzene sulfonates and primary, secondary and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. Other conventional useful surfactants are listed in standard texts.

The surfactant is preferably formulated to be compatible with enzyme components present in the composition. In liquid or gel compositions the surfactant is most preferably formulated such that it promotes, or at least does not degrade, the stability of any enzyme in these compositions.

Nonionic Surfactants

Polyethylene, polypropylene, and polybutylene oxide condensates of alkyl phenols are suitable for use as the nonionic surfactant of the surfactant systems of the present invention, with the polyethylene oxide condensates being preferred. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation, Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA O3O or O5O (the condensation product of $C_{12}$–$C_{14}$ alcohol with 3 or 5 moles of ethylene oxide) marketed by Hoechst. Preferred range of HLB in these products is from 8–11 and most preferred from 8–10.

Also useful as the nonionic surfactant of the surfactant systems of the present invention are the alkylpolysaccharides disclosed in U.S. Pat. No. 4,565,647.

Preferred alkylpolyglycosides have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7.

The condensation products of ethylene oxide with a hydrophobic base formed by the condensation of propylene oxide with propylene glycol are also suitable for use as the additional nonionic surfactant systems of the present invention. Examples of compounds of this type include certain of the commercially-available Plurafac™ LF404 and Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula: $R^2$—C(O)—N($R^1$)—Z wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

Anionic Surfactants

Suitable anionic surfactants to be used are linear alkyl benzene sulfonate, alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

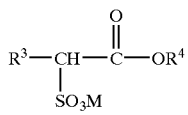

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation. Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes include salts of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—$M^+$ wherein R is a $C_8$–$C_{22}$ alkyl, k is an integer from 1 to 10, and M is a soluble salt-forming cation. Resin acids and hydrogenated resin acids are also suitable, such as rosin, hydrogenated rosin, and resin acids and hydrogenated resin acids present in or derived from tall oil.

Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Highly preferred anionic surfactants include alkyl alkoxylated sulfate surfactants hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}E(1.0)M$), $C_{12}$–$C_{18}$ alkyl polyethoxylate (2.25) sulfate ($C_{12}$–$C_{18}E(2.25)M$), $C_{12}$–$C_{18}$ alkyl polyethoxylate (3.0) sulfate ($C_{12}$–$C_{18}E(3.0)M$), and $C_{12}$–$C_{18}$ alkyl polyethoxylate (4.0) sulfate ($C_{12}$–$C_{18}E(4.0)M$), wherein M is conveniently selected from sodium and potassium.

When included therein, the bleaching compositions of the present invention typically comprise from about 1%, preferably from about 3% to about 40%, preferably about 20% by weight of such anionic surfactants.

Cationic Surfactants

Cationic detersive surfactants suitable for use in the bleaching compositions of the present invention are those having one long-chain hydrocarbyl group. Examples of such cationic surfactants include the ammonium surfactants such as alkyltrimethylammonium halogenides, and those surfactants having the formula: $[R^2(OR^3)_y][R^4(OR^3)_y]_2R^5N+X-$ wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOH$—$CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Highly preferred cationic surfactants are the water-soluble quaternary ammonium compounds useful in the present composition having the formula (i): $R_1R_2R_3R_4N^+X^-$ wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl. The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis. Preferred groups for $R_2R_3$ and $R_4$ are methyl and hydroxyethyl groups and the anion X may be selected from halide, methosulfate, acetate and phosphate ions.

Examples of suitable quaternary ammonium compounds of formulae (i) for use herein are include, but are not limited to: coconut trimethyl ammonium chloride or bromide; coconut methyl dihydroxyethyl ammonium chloride or bromide; decyl triethyl ammonium chloride; decyl dimethyl hydroxyethyl ammonium chloride or bromide; $C_{12-15}$ dimethyl hydroxyethyl ammonium chloride or bromide; coconut dimethyl hydroxyethyl ammonium chloride or bromide; myristyl trimethyl ammonium methyl sulphate; lauryl dimethyl benzyl ammonium chloride or bromide; lauryl dimethyl (ethenoxy)₄ammonium chloride or bromide; choline esters (compounds of formula (i) wherein R¹ is CH₂—CH₂—O—C—C₁₂₋₁₄ alkyl and R₂R₃R₄ are methyl); and di-alkyl imidazolines [(i)].

Other cationic surfactants useful herein are also described in U.S. Pat. No. 4,228,044, Cambre, issued Oct. 14, 1980 and in European Patent Application EP 000,224.

When included therein, the bleaching compositions of the present invention typically comprise from about 0.2%, preferably from about 1% to about 25%, preferably to about 8% by weight of such cationic surfactants.

Ampholytic Surfactants

Ampholytic surfactants, examples of which are described in U.S. Pat. No. 3,929,678, are also suitable for use in the bleaching compositions of the present invention.

When included therein, the bleaching compositions of the present invention typically comprise from about 0.2%, preferably from about 1% to about 15%, preferably to about 10% by weight of such ampholytic surfactants.

Zwitterionic Surfactants

Zwitterionic surfactants, examples of which are described in U.S. Pat. No. 3,929,678, are also suitable for use in bleaching compositions.

When included therein, the bleaching compositions of the present invention typically comprise from about 0.2%, preferably from about 1% to about 15%, preferably to about 10% by weight of such zwitterionic surfactants.

Semi-polar Nonionic Surfactants

Semi-polar nonionic surfactants are a special category of nonionic surfactants which include water-soluble amine oxides having the formula:

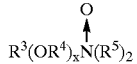

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups (the $R^5$ groups can be attached to each other, e.g., through an oxygen or nitrogen atom, to form a ring structure); water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

The amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the cleaning compositions of the present invention typically comprise from about 0.2%, preferably from about 1% to about 15%, preferably to about 10% by weight of such semi-polar nonionic surfactants.

Cosurfactants

The bleaching compositions of the present invention may further comprise a cosurfactant selected from the group of primary or tertiary amines. Suitable primary amines for use herein include amines according to the formula $R_1NH_2$ wherein $R_1$ is a $C_6$–$C_{12}$, preferably $C_6$–$C_{10}$ alkyl chain or $R_4X(CH_2)_n$, X is —O—, —C(O)NH— or —NH—, $R_4$ is a $C_6$–$C_{12}$ alkyl chain n is between 1 to 5, preferably 3. $R_1$ alkyl chains may be straight or branched and may be interrupted with up to 12, preferably less than 5 ethylene oxide moieties.

Preferred amines according to the formula herein above are n-alkyl amines. Suitable amines for use herein may be selected from 1-hexylamine, 1-octylamine, 1-decylamine and laurylamine. Other preferred primary amines include C8–C10 oxypropylamine, octyloxypropylamine, 2-ethylhexyl-oxypropylamine, lauryl amido propylamine and amido propylamine. The most preferred amines for use in the compositions herein are 1-hexylamine, 1-octylamine, 1-decylamine, 1-dodecylamine. Especially desirable are n-dodecyldimethylamine and bishydroxyethylcoconutalkylamine and oleylamine 7 times ethoxylated, lauryl amido propylamine and cocoamido propylamine.

LFNIs

Particularly preferred surfactants in the automatic dishwashing compositions (ADD) of the present invention are low foaming nonionic surfactants (LFNI) which are described in U.S. Pat. Nos. 5,705,464 and 5,710,115. LFNI may be present in amounts from 0.01% to about 10% by weight, preferably from about 0.1% to about 10%, and most preferably from about 0.25% to about 4%. LFNIs are most typically used in ADDs on account of the improved water-sheeting action (especially from glass) which they confer to the ADD product. They also encompass non-silicone, non-phosphate polymeric materials further illustrated hereinafter which are known to defoam food soils encountered in automatic dishwashing.

Preferred LFNIs include nonionic alkoxylated surfactants, especially ethoxylates derived from primary alcohols, and blends thereof with more sophisticated surfactants, such as the polyoxypropylene/polyoxyethylene/polyoxypropylene (PO/EO/PO) reverse block polymers as described in U.S. Pat. Nos. 5,705,464 and 5,710,115.

LFNIs which may also be used include those POLY-TERGENT® SLF-18 nonionic surfactants from Olin Corp., and any biodegradable LFNI having the melting point properties discussed hereinabove.

These and other nonionic surfactants are well known in the art, being described in more detail in Kirk Othmer's Encyclopedia of Chemical Technology, 3rd Ed., Vol. 22, pp. 360–379, "Surfactants and Detersive Systems", incorporated by reference herein.

Bleaching Agents

The compositions of the present invention optionally comprise, in addition to the bleaching system described above, additional bleaching agents, such as chlorine bleaches (although less preferred for compositions which comprise enzymes) examples of which are known in the art, and include sodium dichloroisocyanurate ("NaDCC") and bleach catalysts. When present, these other bleaching agents will typically be at levels of from about 1%, preferably from about 5% to about 30%, preferably to about 20% by weight of the composition.

(a) Organic Peroxides, especially Diacyl Peroxides

These are extensively illustrated in Kirk Othmer, Encyclopedia of Chemical Technology, Vol. 17, John Wiley and Sons, 1982 at pages 27–90 and especially at pages 63–72, all incorporated herein by reference. If a diacyl peroxide is used, it will preferably be one which exerts minimal adverse impact on spotting/filming.

(b) Metal-containing Bleach Catalysts

The present invention compositions and methods may utilize metal-containing bleach catalysts that are effective for use in bleaching compositions. Preferred are manganese and cobalt-containing bleach catalysts.

One type of metal-containing bleach catalyst is a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 Bragg, issued Feb. 2, 1982.

Manganese Metal Complexes

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1, 549,272 A1, 544,440 A2, and 544,490 A1; Preferred examples of these catalysts include $Mn^{IV}_2(u-O)_3(1,4,7-\text{trimethyl-}1,4,7\text{-triazacyclononane})_2(PF_6)_2$, $Mn^{III}_2(u-O)_1(u-OAc)_2(1,4,7\text{-trimethyl-}1,4,7\text{-triazacyclononane})_2(ClO_4)_2$, $Mn^{IV}_4(u-O)_6(1,4,7\text{-triazacyclononane})_4(ClO_4)_4$, $Mn^{III}Mn^{IV}_4(u-O)_1(u-OAc)_2\_(1,4,7\text{-trimethyl-}1,4,7\text{-triazacyclononane})_2(ClO_4)_3$, $Mn^{IV}(1,4,7\text{-trimethyl-}1,4,7\text{-triazacyclononane})\text{-}(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt Metal Complexes

Cobalt bleach catalysts useful herein are known, and are described, for example, in U.S. Pat. Nos. 5,597,936; 5,595,967; and 5,703,030; and M. L. Tobe, "Base Hydrolysis of Transition-Metal Complexes", *Adv. Inorg. Bioinorg. Mech.*, (1983), 2, pages 1–94. The most preferred cobalt catalyst useful herein are cobalt pentaamine acetate salts having the formula $[Co(NH_3)_5OAc]T_y$, wherein "OAc" represents an acetate moiety and "$T_y$" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5OAc](SO_4)$; $[Co(NH_3)_5OAc](BF_4)_2$; and $[Co(NH_3)_5OAc](NO_3)_2$ (herein "PAC").

These cobalt catalysts are readily prepared by known procedures, such as taught for example in U.S. Pat. Nos. 5,597,936; 5,595,967; and 5,703,030; in the Tobe article and the references cited therein; and in U.S. Pat. No. 4,810,410; *J. Chem. Ed.* (1989), 66 (12), 1043–45; The Synthesis and Characterization of Inorganic Compounds, W. L. Jolly (Prentice-Hall; 1970), pp. 461–3; *Inorg. Chem.*, 18, 1497–1502 (1979); *Inorg. Chem.*, 21, 2881–2885 (1982); *Inorg. Chem.*, 18, 2023–2025 (1979); Inorg. Synthesis, 173–176 (1960); and *Journal of Physical Chemistry*, 56, 22–25 (1952).

Transition Metal Complexes of Macropolycyclic Rigid Ligands

Compositions herein may also suitably include as bleach catalyst a transition metal complex of a macropolycyclic rigid ligand. The phrase "macropolycyclic rigid ligand" is sometimes abbreviated as "MRL" in discussion below. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Suitable transition metals e.g., Mn are illustrated hereinafter. "Macropolycyclic" means a MRL is both a macrocycle and is polycyclic. "Polycyclic" means at least bicyclic. The term "rigid" as used herein herein includes "having a superstructure" and "cross-bridged". "Rigid" has been defined as the constrained converse of flexibility: see D. H. Busch., *Chemical Reviews.*, (1993), 93, 847–860, incorporated by reference. More particularly, "rigid" as used herein means that the MRL must be determinably more rigid than a macrocycle ("parent macrocycle") which is otherwise identical (having the same ring size and type and number of atoms in the main ring) but lacking a superstructure (especially linking moieties or, preferably cross-bridging moieties) found in the MRL's. In determining the comparative rigidity of macrocycles with and without superstructures, the practitioner will use the free form (not the metal-bound form) of the macrocycles. Rigidity is well-known to be useful in comparing macrocycles; suitable tools for determining, measuring or comparing rigidity include computational methods (see, for example, Zimmer, *Chemical Reviews*, (1995), 95(38), 2629–2648 or Hancock et al., *Inorganica Chimica Acta*, (1989), 164, 73–84.

Preferred MRL's herein are a special type of ultra-rigid ligand which is cross-bridged. A "cross-bridge" is nonlimitingly illustrated in 1.11 hereinbelow. In 1.11, the cross-bridge is a —$CH_2CH_2$— moiety. It bridges $N^1$ and $N^8$ in the illustrative structure. By comparison, a "same-side" bridge, for example if one were to be introduced across $N^1$ and $N^{12}$ in 1.11, would not be sufficient to constitute a "cross-bridge" and accordingly would not be preferred.

Suitable metals in the rigid ligand complexes include Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV). Preferred transition-metals in the instant transition-metal bleach catalyst include manganese, iron and chromium.

More generally, the MRL's (and the corresponding transition-metal catalysts) herein suitably comprise:

(a) at least one macrocycle main ring comprising four or more heteroatoms; and
(b) a covalently connected non-metal superstructure capable of increasing the rigidity of the macrocycle, preferably selected from
(i) a bridging superstructure, such as a linking moiety;
(ii) a cross-bridging superstructure, such as a cross-bridging linking moiety; and
(iii) combinations thereof.

The term "superstructure" is used herein as defined in the literature by Busch et al., see, for example, articles by Busch in "Chemical Reviews".

Preferred superstructures herein not only enhance the rigidity of the parent macrocycle, but also favor folding of the macrocycle so that it co-ordinates to a metal in a cleft. Suitable superstructures can be remarkably simple, for example a linking moiety such as any of those illustrated in FIG. 1 and FIG. 2 below, can be used.

FIG. 1 wherein n is an integer, for example from 2 to 8, preferably less than 6, typically 2 to 4, or

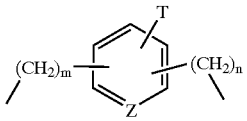

FIG. 2 wherein m and n are integers from about 1 to 8, more preferably from 1 to 3; Z is N or CH; and T is a compatible substituent, for example H, alkyl, trialkylammonium, halogen, nitro, sulfonate, or the like. The aromatic ring in 1.10 can be replaced by a saturated ring, in which the atom in Z connecting into the ring can contain N, O, S or C.

Suitable MRL's are further nonlimitingly illustrated by the following compound:

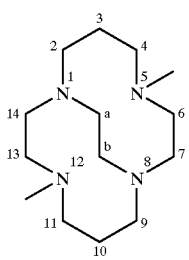

FIG. 3

This is a MRL in accordance with the invention which is a highly preferred, cross-bridged, methyl-substituted (all nitrogen atoms tertiary) derivative of cyclam. Formally, this ligand is named 5,12-dimethyl-1,5,8,12-tetraazabicyclo [6.6.2]hexadecane using the extended von Baeyer system. See "A Guide to IUPAC Nomenclature of Organic Compounds: Recommendations 1993", R. Panico, W. H. Powell and J-C Richer (Eds.), Blackwell Scientific Publications, Boston, 1993; see especially section R-2.4.2.1.

Transition-metal bleach catalysts of Macrocyclic Rigid Ligands which are suitable for use in the invention compositions can in general include known compounds where they conform with the definition herein, as well as, more preferably, any of a large number of novel compounds expressly designed for the present laundry or cleaning uses, and non-limitingly illustrated by any of the following:

Dichloro-5,12-dimethyl-1,5,8,12-tetraazabicyclo[6.6.2] hexadecane Manganese(I)
Diaquo-5,12-dimethyl-1,5,8,12-tetraazabicyclo[6.6.2] hexadecane Manganese(II) Hexafluorophosphate
Aquo-hydroxy-5,12-dimethyl-1,5,8,12-tetraazabicyclo [6.6.2]hexadecane Manganese(III) Hexafluorophosphate
Diaquo-5,12-dimethyl-1,5,8,12-tetraazabicyclo[6.6.2] hexadecane Manganese(III) Tetrafluoroborate
Dichloro-5,12-dimethyl-1,5,8,12-tetraazabicyclo[6.6.2] hexadecane Manganese(III) Hexafluorophosphate
Dichloro-5,12-di-n-butyl-1,5,8,12-tetraaza bicyclo[6.6.2] hexadecane Manganese(II)
Dichloro-5,12-dibenzyl-1,5,8,12-tetraazabicyclo[6.6.2] hexadecane Manganese(II)
Dichloro-5-n-butyl-12-methyl-1,5,8,12-tetraaza-bicyclo [6.6.2]hexadecane Manganese(II)
Dichloro-5-n-octyl-12-methyl-1,5,8,12-tetraaza-bicyclo [6.6.2]hexadecane Manganese(II)
Dichloro-5-n-butyl-12-methyl-1,5,8,12-tetraaza-bicyclo [6.6.2]hexadecane Manganese(II).

As a practical matter, and not by way of limitation, the compositions and cleaning processes herein can be adjusted to provide on the order of at least one part per hundred million of the active bleach catalyst species in the aqueous washing medium, and will preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic washing process, typical compositions herein will comprise from about 0.0005% to about 0.2%, more preferably from about 0.004% to about 0.08%, of bleach catalyst, especially manganese or cobalt catalysts, by weight of the bleaching compositions.

(d) Other Bleach Catalysts

The compositions herein may comprise one or more other bleach catalysts. Preferred bleach catalysts are zwitterionic bleach catalysts, which are described in U.S. Pat. No. 5,576,282 (especially 3-(3,4-dihydroisoquinolinium) propane sulfonate. Other bleach catalysts include cationic bleach catalysts are described in U.S. Pat. Nos. 5,360,569, 5,442,066, 5,478,357, 5,370,826, 5,482,515, 5,550,256, and WO 95/13351, WO 95/13352, and WO 95/13353.

Optional Detersive Enzymes

The detergent and bleaching compositions herein may also optionally contain one or more types of detergent enzymes. Such enzymes can include other proteases, amylases, cellulases and lipases. Such materials are known in the art and are commercially available under such trademarks as. They may be incorporated into the non-aqueous liquid detergent compositions herein in the form of suspensions, "marumes" or "prills". Another suitable type of enzyme comprises those in the form of slurries of enzymes in nonionic surfactants, e.g., the enzymes marketed by Novo Nordisk under the tradename "SL" or the microencapsulated enzymes marketed by Novo Nordisk under the tradename "LDP." Suitable enzymes and levels of use are described in U.S. Pat. No. 5,576,282, 5,705,464 and 5,710,115.

Enzymes added to the compositions herein in the form of conventional enzyme prills are especially preferred for use herein. Such prills will generally range in size from about 100 to 1,000 microns, more preferably from about 200 to 800 microns and will be suspended throughout the non-aqueous liquid phase of the composition. Prills in the compositions of the present invention have been found, in comparison with other enzyme forms, to exhibit especially desirable enzyme stability in terms of retention of enzymatic activity over time. Thus, compositions which utilize enzyme prills need not contain conventional enzyme stabilizing such as must frequently be used when enzymes are incorporated into aqueous liquid detergents.

However, enzymes added to the compositions herein may be in the form of granulates, preferably T-granulates.

"Detersive enzyme", as used herein, means any enzyme having a cleaning, stain removing or otherwise beneficial effect in a laundry, hard surface cleaning or personal care detergent composition. Preferred detersive enzymes are hydrolases such as proteases, amylases and lipases. Preferred enzymes for laundry purposes include, but are not limited to, proteases, cellulases, lipases and peroxidases. Highly preferred for automatic dishwashing are amylases and/or proteases, including both current commercially available types and improved types which, though more and more bleach compatible though successive improvements, have a remaining degree of bleach deactivation susceptibility.

Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof.

Examples of such suitable enzymes are disclosed in U.S. Pat. Nos. 5,705,464, 5,710,115, 5,576,282, 5,728,671 and 5,707,950

The cellulases useful in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J61078384 and WO96/02653 which discloses fungal cellulase produced respectively from Humicola insolens, Trichoderma, Thielavia and Sporotrichum. EP 739 982 describes cellulases isolated from novel Bacillus species. Suitable cellulases are also disclosed in GB-A-2.075.028; GB-A-2.095.275; DE-OS-2.247.832 and WO95/26398.

Examples of such cellulases are cellulases produced by a strain of *Humicola insolens* (*Humicola grisea* var. *thermoidea*), particularly the Humicola strain DSM 1800. Other suitable cellulases are cellulases originated from *Humicola insolens* having a molecular weight of about 50 KDa, an isoelectric point of 5.5 and containing 415 amino acids; and a ~43 kD endoglucanase derived from *Humicola insolens*, DSM 1800, exhibiting cellulase activity; a preferred endoglucanase component has the amino acid sequence disclosed in WO 91/17243. Also suitable cellulases are the EGIII cellulases from *Trichoderma longibrachiatum* described in WO94/21801 to Genencor. Especially suitable cellulases are the cellulases having color care benefits. Examples of such cellulases are cellulases described in European patent application No. 91202879.2, filed Nov. 6, 1991 (Novo). Carezyme and Celluzyme (Novo Nordisk A/S) are especially useful. See also WO91/17244 and WO91/21801. Other suitable cellulases for fabric care and/or cleaning properties are described in WO96/34092, WO96/17994 and WO95/24471.

Cellulases, when present, are normally incorporated in the cleaning composition at levels from 0.0001% to 2% of pure enzyme by weight of the cleaning composition.

Peroxidase enzymes are used in combination with oxygen sources, e.g. percarbonate, perborate, persulfate, hydrogen peroxide, etc and with a phenolic substrate as bleach enhancing molecule. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase and haloperoxidase such as chloro- and bromo-peroxidase. Suitable peroxidases and peroxidase-containing detergent compositions are disclosed, for example, in U.S. Pat. Nos. 5,705,464, 5,710,115, 5,576,282, 5,728,671 and 5,707,950, PCT International Application WO 89/099813, WO89/09813 and in European Patent application EP No. 91202882.6, filed on Nov. 6, 1991 and EP No. 96870013.8, filed Feb. 20, 1996. Also suitable is the laccase enzyme.

Enhancers are generally comprised at a level of from 0.1% to 5% by weight of total composition. Preferred enhancers are substitued phenthiazine and phenoxasine 10-Phenothiazinepropionicacid (PPT), 10-ethylphenothiazine-4-carboxylic acid (EPC), 10-phenoxazinepropionic acid (POP) and 10-methylphenoxazine (described in WO 94/12621) and substitued syringates (C3–C5 substitued alkyl syringates) and phenols. Sodium percarbonate or perborate are preferred sources of hydrogen peroxide. Said peroxidases are normally incorporated in the cleaning composition at levels from 0.0001% to 2% of pure enzyme by weight of the cleaning composition.

Enzymatic systems may be used as bleaching agents. The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

Other preferred enzymes that can be included in the cleaning compositions of the present invention include lipases. Suitable lipase enzymes for detergent usage include those produced by microorganisms of the Pseudomonas group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. Especially suitable lipases are lipases such as M1 Lipase$^{R\ and}$ Lipomax$^R$ (Gist-Brocades) and Lipolase$^R$ and Lipolase Ultra$^R$(Novo) which have found to be very effective when used in combination with the compositions of the present invention. Also suitable are the lipolytic enzymes described in EP 258 068, WO 92/05249 and WO 95/22615 by Novo Nordisk and in WO 94/03578, WO 95/35381 and WO 96/00292 by Unilever.

Also suitable are cutinases [EC 3.1.1.50] which can be considered as a special kind of lipase, namely lipases which do not require interfacial activation. Addition of cutinases to cleaning compositions have been described in e.g. WO-A-88/09367 (Genencor); WO 90/09446 (Plant Genetic System) and WO 94/14963 and WO 94/14964 (Unilever).

Lipases and/or cutinases, when present, are normally incorporated in the cleaning composition at levels from 0.0001% to 2% of pure enzyme by weight of the cleaning composition.

In addition to the above referenced lipases, phospholipases may be incorporated into the cleaning compositions of the present invention. Nonlimiting examples of suitable phospholipases included: EC 3.1.1.32 Phospholipase A1; EC 3.1.1.4 Phospholipase A2; EC 3.1.1.5 Lysopholipase; EC 3.1.4.3 Phospholipase C; EC 3.1.4.4. Phospolipase D. Commercially available phospholipases include LECITASE® from Novo Nordisk A/S of Denmark and Phospholipase A2 from Sigma. When phospolipases are included in the compositions of the present invention, it is preferred that amylases are also included. Without desiring to be bound by theory, it is believed that the combined action of the phospholipase and amylase provide substantive stain removal, especially on greasy/oily, starchy and highly colored stains and soils. Preferably, the phospholipase and amylase, when present, are incorporated into the compositions of the present invention at a pure enzyme weight ratio between 4500:1 and 1:5, more preferably between 50:1 and 1:1.

Suitable proteases are the subtilisins which are obtained from particular strains of B. subtilis and B. licheniformis (subtilisin BPN and BPN'). One suitable protease is obtained from a strain of Bacillus, having maximum activity throughout the pH range of 8–12, developed and sold as ESPE-RASE® by Novo Industries A/S of Denmark, hereinafter "Novo". The preparation of this enzyme and analogous enzymes is described in GB 1,243,784 to Novo. Proteolytic enzymes also encompass modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine protealytic enzyme which is called "Protease A" herein. Suitable is the protease called herein "Protease C", which is a variant of an alkaline serine protease from Bacillus in which Lysine replaced arginine at position 27, tyrosine replaced valine at position 104, serine replaced asparagine at position 123, and alanine replaced threonine at position 274. Protease C is described in EP 90915958:4, corresponding to WO 91/06637, Published May 16, 1991. Genetically modified variants, particularly of Protease C, are also included herein.

A preferred protease referred to as "Protease D" is a carbonyl hydrolase as described in U.S. Pat. No. 5,677,272, and WO95/10591. Also suitable is a carbonyl hydrolase variant of the protease described in WO95/10591, having an amino acid sequence derived by replacement of a plurality of amino acid residues replaced in the precursor enzyme corresponding to position +210 in combination with one or more of the following residues: +33, +62, +67, +76, +100, +101, +103, +104, +107, +128, +129, +130, +132, +135, +156, +158, +164, +166, +167, +170, +209, +215, +217, +218, and +222, where the numbered position corresponds to naturally-occurring subtilisin from Bacillus amyloliquefaciens or to equivalent amino acid residues in other carbonyl hydrolases or subtilisins, such as Bacillus lentus subtilisin (co-pending patent application U.S. Serial No. 60/048, 550, filed Jun. 4, 1997 and PCT International Application Serial No. PCT/IB98/00853).

Also suitable for the present invention are proteases described in patent applications EP 251 446 and WO 91/06637, protease BLAP® described in WO91/02792 and their variants described in WO 95/23221.

See also a high pH protease from Bacillus sp. NCIMB 40338 described in WO 93/18140 A to Novo. Enzymatic detergents comprising protease, one or more other enzymes, and a reversible protease inhibitor are described in WO 92/03529 A to Novo. When desired, a protease having decreased adsorption and increased hydrolysis is available as described in WO 95/07791 to Procter & Gamble. A recombinant trypsin-like protease for detergents suitable herein is described in WO 94/25583 to Novo. Other suitable proteases are described in EP 516 200 by Unilever.

Particularly useful proteases are described in PCT publications: WO 95/30010; WO 95/30011; and WO 95/29979. Suitable proteases are commercially available as ESPERASE®, ALCALASE®, DURAZYM®, SAVINASE®, EVERLASE® and KANNASE® all from Novo Nordisk A/S of Denmark, and as MAXATASE®, MAXACAL®, PROPERASE® and MAXAPEM® all from Genencor International (formerly Gist-Brocades of The Netherlands).

Such proteolytic enzymes, when present, are incorporated in the cleaning compositions of the present invention a level of from 0.0001% to 2%, preferably from 0.001% to 0.2%, more preferably from 0.005% to 0.1% pure enzyme by weight of the composition.

Amylases ($\alpha$ and/or $\beta$) can be included for removal of carbohydrate-based stains. WO94/02597 describes cleaning compositions which incorporate mutant amylases. See also WO95/10603. Other amylases known for use in cleaning compositions include both $\alpha$- and $\beta$-amylases. $\alpha$-Amylases are known in the art and include those disclosed in U.S. Pat. No. 5,003,257; EP 252,666; WO/91/00353; FR 2,676,456; EP 285,123; EP 525,610; EP 368,341; and British Patent specification no. 1,296,839 (Novo). Other suitable amylases are stability-enhanced amylases described in WO94/18314 and WO96/05295, Genencor, and amylase variants having additional modification in the immediate parent available from Novo Nordisk A/S, disclosed in WO 95/10603. Also suitable are amylases described in EP 277 216.

Examples of commercial $\alpha$-amylases products are Purafect Ox Am® from Genencor and Termamyl®, Ban®, Fungamyl® and Duramyl®, all available from Novo Nordisk A/S Denmark. WO95/26397 describes other suitable amylases: $\alpha$-amylases characterised by having a specific activity at least 25% higher than the specific activity of Termamyl® at a temperature range of 25° C. to 55° C. and at a pH value in the range of 8 to 10, measured by the Phadebas® $\alpha$-amylase activity assay. Suitable are variants of the above enzymes, described in WO96/23873 (Novo Nordisk). Other amylolytic enzymes with improved properties with respect to the activity level and the combination of thermostability and a higher activity level are described in WO95/35382.

Such amylolytic enzymes, when present, are incorporated in the cleaning compositions of the present invention a level of from 0.0001% to 2%, preferably from 0.00018% to 0.06%, more preferably from 0.00024% to 0.048% pure enzyme by weight of the composition.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein/genetic engineering techniques in order to optimize their performance efficiency in the laundry detergent and/or fabric care compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing calcium binding sites to increase chelant stability.

These optional detersive enzymes, when present, are normally incorporated in the cleaning composition at levels from 0.0001% to 2% of pure enzyme by weight of the cleaning composition. The enzymes can be added as separate single ingredients (prills, granulates, stabilized liquids, etc. . . containing one enzyme) or as mixtures of two or more enzymes (e.g. cogranulates).

Other suitable detergent ingredients that can be added are enzyme oxidation scavengers. Examples of such enzyme oxidation scavengers are ethoxylated tetraethylene polyamines.

A range of enzyme materials and means for their incorporation into synthetic detergent compositions is also disclosed in WO 9307263 and WO 9307260 to Genencor International, WO 8908694, and U.S. Pat. No. 3,553,139, Jan. 5, 1971 to McCarty et al. Enzymes are further disclosed in U.S. Pat. No. 4,101,457, and in U.S. Pat. No. 4,507,219. Enzyme materials useful for liquid detergent formulations, and their incorporation into such formulations, are disclosed in U.S. Pat. No. 4,261,868.

Enzyme Stabilizers

Enzymes for use in detergents can be stabilized by various techniques. Enzyme stabilization techniques are disclosed and exemplified in U.S. Pat. No. 3,600,319, EP 199,405 and EP 200,586. Enzyme stabilization systems are also described, for example, in U.S. Pat. No. 3,519,570. A useful Bacillus, sp. AC 13 giving proteases, xylanases and cellulases, is described in WO 9401532. The enzymes employed herein can be stabilized by the presence of water-soluble sources of calcium and/or magnesium ions in the finished compositions which provide such ions to the enzymes. Suitable enzyme stabilizers and levels of use are described in U.S. Pat. Nos. 5,705,464, 5,710,115 and 5,576,282.

Builders

The detergent and bleaching compositions described herein preferably comprise one or more detergent builders or builder systems. When present, the compositions will typically comprise at least about 1% builder, preferably from about 5%, more preferably from about 10% to about 80%, preferably to about 50%, more preferably to about 30% by weight, of detergent builder. Lower or higher levels of builder, however, are not meant to be excluded.

Preferred builders for use in the detergent and bleaching compositions, particularly dishwashing compositions, described herein include, but are not limited to, water-soluble builder compounds, (for example polycarboxylates) as described in U.S. Pat. Nos. 5,695,679, 5,705,464 and 5,710,115. Other suitable polycarboxylates are disclosed in U.S. Pat. Nos. 4,144,226, 3,308,067 and 3,723,322. Preferred polycarboxylates are hydroxycarboxylates containing up to three carboxy groups per molecule, more particularly citrates.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates (see, for example, U.S. Pat. Nos. 3,159,581; 3,213,030; 3,422,021; 3,400,148 and 3,422,137), phytic acid, silicates, carbonates (including bicarbonates and sesquicarbonates), sulphates, and aluminosilicates.

However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Suitable silicates include the water-soluble sodium silicates with an $SiO_2:Na_2O$ ratio of from about 1.0 to 2.8, with ratios of from about 1.6 to 2.4 being preferred, and about 2.0 ratio being most preferred. The silicates may be in the form of either the anhydrous salt or a hydrated salt. Sodium silicate with an $SiO_2:Na_2O$ ratio of 2.0 is the most preferred. Silicates, when present, are preferably present in the detergent and bleaching compositions described herein at a level of from about 5% to about 50% by weight of the composition, more preferably from about 10% to about 40% by weight.

Partially soluble or insoluble builder compounds, which are suitable for use in the detergent and bleaching compositions, particularly granular detergent compositions, include, but are not limited to, crystalline layered silicates, preferably crystalline layered sodium silicates (partially water-soluble) as described in U.S. Pat. No. 4,664,839, and sodium aluminosilicates (water-insoluble). When present in detergent and bleaching compositions, these builders are typically present at a level of from about 1% to 80% by weight, preferably from about 10% to 70% by weight, most preferably from about 20% to 60% by weight of the composition.

Crystalline layered sodium silicates having the general formula $NaMSi_xO_{2x+1} \cdot yH_2O$ wherein M is sodium or hydrogen, x is a number from about 1.9 to about 4, preferably from about 2 to about 4, most preferably 2, and y is a number from about 0 to about 20, preferably 0 can be used in the compositions described herein. Crystalline layered sodium silicates of this type are disclosed in EP-A-0164514 and methods for their preparation are disclosed in DE-A-3417649 and DE-A-3742043. The most preferred material is delta-$Na_2SiO_5$, available from Hoechst AG as NaSKS-6 (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. SKS-6 is a highly preferred layered silicate for use in the compositions described herein herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used in the compositions described herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

The crystalline layered sodium silicate material is preferably present in granular detergent compositions as a particulate in intimate admixture with a solid, water-soluble ionizable material. The solid, water-soluble ionizable material is preferably selected from organic acids, organic and inorganic acid salts and mixtures thereof.

Aluminosilicate builders are of great importance in most currently marketed heavy duty granular detergent compositions, and can also be a significant builder ingredient in liquid detergent formulations. Aluminosilicate builders have the empirical formula:

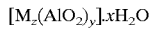

$[M_z(AlO_2)_y] \cdot xH_2O$ wherein z and y are integers of at least 6, the molar ratio of z to y is in the range from 1.0 to about 0.5, and x is an integer from about 15 to about 264. Preferably, the aluminosilicate builder is an aluminosilicate zeolite having the unit cell formula:

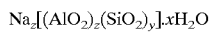

$Na_z[(AlO_2)_z(SiO_2)_y] \cdot xH_2O$ wherein z and y are at least 6; the molar ratio of z to y is from 1.0 to 0.5 and x is at least 5, preferably 7.5 to 276, more preferably from 10 to 264. The aluminosilicate builders are preferably in hydrated form and are preferably crystalline, containing from about 10% to about 28%, more preferably from about 18% to about 22% water in bound form.

These aluminosilicate ion exchange materials can be crystalline or amorphous in structure and can be naturally-occurring aluminosilicates or synthetically derived. A method for producing aluminosilicate ion exchange materials is disclosed in U.S. 3,985,669. Preferred synthetic crystalline aluminosilicate ion exchange materials useful herein are available under the designations Zeolite A, Zeolite B, Zeolite P, Zeolite X, Zeolite MAP and Zeolite HS and mixtures thereof. In an especially preferred embodiment, the crystalline aluminosilicate ion exchange material has the formula:

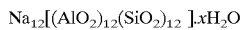

$$Na_{12}[(AlO_2)_{12}(SiO_2)_{12}] \cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter. Zeolite X has the formula:

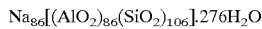

$$Na_{86}[(AlO_2)_{86}(SiO_2)_{106}] \cdot 276H_2O$$

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions described herein are the 3,3-dicarboxy-4-oxa-1,6-hexanedioates and the related compounds disclosed in U.S. Pat. No. 4,566,984. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

Dispersants

One or more suitable polyalkyleneimine dispersants may be incorporated into the cleaning compositions of the present invention. Examples of such suitable dispersants can be found in European Patent Application Nos. 111,965, 111,984, and 112,592; U.S. Pat. Nos. 4,597,898, 4,548,744, and 5,565,145. However, any suitable clay/soil dispersent or anti-redepostion agent can be used in the laundry compositions of the present invention.

In addition, polymeric dispersing agents which include polymeric polycarboxylates and polyethylene glycols, are suitable for use in the present invention. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in U.S. Pat. No. 3,308,067.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Soil Release Agents

The compositions according to the present invention may optionally comprise one or more soil release agents. If utilized, soil release agents will generally comprise from about 0.01%, preferably from about 0.1%, more preferably from about 0.2% to about 10%, preferably to about 5%, more preferably to about 3% by weight, of the composition. Nonlimiting examples of suitable soil release polymers are disclosed in: U.S. Pat. Nos. 5,728,671; 5,691,298; 5,599,782; 5,415,807; 5,182,043; 4,956,447; 4,976,879; 4,968,451; 4,925,577; 4,861,512; 4,877,896; 4,771,730; 4,711,730; 4,721,580; 4,000,093; 3,959,230; and 3,893,929; and European Patent Application 0 219 048.

Further suitable soil release agents are described in U.S. Pat. Nos. 4,201,824; 4,240,918; 4,525,524; 4,579,681; 4,220,918; and 4,787,989; EP 279,134 A; EP457,205 A; and DE 2,335,044.

Chelating Agents

The compositions of the present invention herein may also optionally contain a chelating agent which serves to chelate metal ions and metal impurities which would otherwise tend to deactivate the bleaching agent(s). Useful chelating agents can include amino carboxylates, phosphonates, amino phosphonates, polyfunctionally-substituted aromatic chelating agents and mixtures thereof. Further examples of suitable chelating agents and levels of use are described in U.S. Pat. Nos. 5,705,464, 5,710,115, 5,728,671 and 5,576,282.

The compositions herein may also contain water-soluble methyl glycine diacetic acid (MGDA) salts (or acid form) as a chelant or co-builder useful with, for example, insoluble builders such as zeolites, layered silicates and the like.

If utilized, these chelating agents will generally comprise from about 0.1% to about 15%, more preferably from about 0.1% to about 3.0% by weight of the detergent compositions herein.

Suds suppressor

Another optional ingredient is a suds suppressor, exemplified by silicones, and silica-silicone mixtures. Examples of suitable suds suppressors are disclosed in U.S. Pat. Nos. 5,707,950 and 5,728,671. These suds suppressors are normally employed at levels of from 0.001% to 2% by weight of the composition, preferably from 0.01% to 1% by weight.

Softening agents

Fabric softening agents can also be incorporated into laundry detergent compositions in accordance with the present invention. Inorganic softening agents are exemplified by the smectite clays disclosed in GB-A-1 400 898 and in U.S. Pat. No. 5,019,292. Organic softening agents include the water insoluble tertiary amines as disclosed in GB-A-1 514 276 and EP-B-011 340 and their combination with mono C12–C14 quaternary ammonium salts are disclosed in EP-B-026 527 and EP-B-026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Particularly suitable fabric softening agents are disclosed in U.S. Pat. Nos. 5,707,950 and 5,728,673.

Levels of smectite clay are normally in the range from 2% to 20%, more preferably from 5% to 15% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Biodegradable quaternary ammonium compounds as described in EP-A-040 562 and EP-A-239 910 have been presented as alternatives to the traditionally used di-long alkyl chain ammonium chlorides and methyl sulfates.

Non-limiting examples of softener-compatible anions for the quaternary ammonium compounds and amine precursors include chloride or methyl sulfate.

Dye transfer inhibition

The detergent compositions of the present invention can also include compounds for inhibiting dye transfer from one fabric to another of solubilized and suspended dyes encountered during fabric laundering and conditioning operations involving colored fabrics.

Polymeric Dye Transfer Inhibiting Agents

The detergent compositions according to the present invention can also comprise from 0.001% to 10%, preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash.

Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof. Examples of such dye transfer inhibiting agents are disclosed in U.S. Pat. Nos. 5,707,950 and 5,707,951.

Additional suitable dye transfer inhibiting agents include, but are not limited to, cross-linked polymers. Cross-linked polymers are polymers whose backbone are interconnected to a certain degree; these links can be of chemical or physical nature, possibly with active groups n the backbone or on branches; cross-linked polymers have been described in the Journal of Polymer Science, volume 22, pages 1035–1039.

In one embodiment, the cross-linked polymers are made in such a way that they form a three-dimensional rigid structure, which can entrap dyes in the pores formed by the three-dimensional structure. In another embodiment, the cross-linked polymers entrap the dyes by swelling. Such cross-linked polymers are described in the co-pending European patent application 94870213.9.

Addition of such polymers also enhances the performance of the enzymes according the invention.

pH and Buffering Variation

Many of the detergent and bleaching compositions described herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH-jump systems, dual compartment containers, etc., and are well known to those skilled in the art.

The preferred ADD compositions herein comprise a pH-adjusting component selected from water-soluble alkaline inorganic salts and water-soluble organic or inorganic builders as described in U.S. Pat. Nos. 5,705,464 and 5,710,115.

Material Care Agents

The preferred ADD compositions may contain one or more material care agents which are effective as corrosion inhibitors and/or anti-tarnish aids as described in U.S. Pat. Nos. 5,705,464, 5,710,115 and 5,646,101.

When present, such protecting materials are preferably incorporated at low levels, e.g., from about 0.01% to about 5% of the ADD composition.

Other Materials

Detersive ingredients or adjuncts optionally included in the instant compositions can include one or more materials for assisting or enhancing cleaning performance, treatment of the substrate to be cleaned, or designed to improve the aesthetics of the compositions. Adjuncts which can also be included in compositions of the present invention, at their conventional art-established levels for use (generally, adjunct materials comprise, in total, from about 30% to about 99.9%, preferably from about 70% to about 95%, by weight of the compositions), include other active ingredients such as non-phosphate builders, color speckles, silvercare, anti-tarnish and/or anti-corrosion agents, dyes, fillers, germicides, alkalinity sources, hydrotropes, anti-oxidants, perfumes, solubilizing agents, carriers, processing aids, pigments, and pH control agents as described in U.S. Pat. Nos. 5,705,464, 5,710,115, 5,698,504, 5,695,679, 5,686,014 and 5,646,101.

Methods of Cleaning

In addition to the methods for cleaning fabrics, dishes and other hard surfaces, and body parts by personal cleansing, described herein, the invention herein also encompasses a laundering pretreatment process for fabrics which have been soiled or stained comprising directly contacting said stains and/or soils with a highly concentrated form of the bleaching composition set forth above prior to washing such fabrics using conventional aqueous washing solutions. Preferably, the bleaching composition remains in contact with the soil/stain for a period of from about 30 seconds to 24 hours prior to washing the pretreated soiled/stained substrate in conventional manner. More preferably, pretreatment times will range from about 1 to 180 minutes.

The following examples are meant to exemplify compositions of the present invention, but are not necessarily meant to limit or otherwise define the scope of the invention.

In all of the following examples Protease[1] means a protease variant comprising substitution of amino acid residues with another naturally occurring amino acid residue at positions corresponding to positions 101G/103A/104I/159D/232V/236H/245R/248D/252K of *Bacillus amyloliquefaciens* subtilisin. Protease[1] can be substituted with any other additional protease variant of the present invention, with substantially similar results in the following examples.

In the cleaning composition examples of the present invention, the Protease[1] enzyme levels are expressed by pure enzyme by weight of the total composition, the other enzyme levels are expressed by raw material by weight of the total composition, and unless otherwise specified, the other ingredients are expressed by weight of the total composition.

Further, in the following examples some abbreviations known to those of ordinary skill in the art are used, consistent with the disclosure set forth herein.

EXAMPLE 1

Granular Automatic Dishwashing Composition

| Component | A | B | C |
|---|---|---|---|
| Citric Acid | 15.0 | — | — |
| Citrate | 4.0 | 29.0 | 15.0 |
| Acrylate/methacrylate copolymer | 6.0 | — | 6.0 |
| Acrylic acid maleic acid copolymer | — | 3.7 | — |
| Dry add carbonate | 9.0 | — | 20.0 |
| Alkali metal silicate | 8.5 | 17.0 | 9.0 |
| Paraffin | — | 0.5 | — |
| Benzotriazole | — | 0.3 | — |
| Termamyl 60T | 1.6 | 1.6 | 1.6 |
| Protease[1] | 0.2 | 0.1 | 0.06 |
| Percarbonate (AvO) | 1.5 | — | — |
| Perborate monohydrate | — | 0.3 | 1.5 |

EXAMPLE 1-continued

Granular Automatic Dishwashing Composition

| Component | A | B | C |
|---|---|---|---|
| Perborate tetrahydrate | — | 0.9 | — |
| NOBS | — | — | 2.40 |
| TAED | 3.8 | 4.4 | — |
| Diethylene triamine penta methyl phosphonic acid (Mg salt) | 0.13 | 0.13 | 0.13 |
| Alkyl ethoxy sulphate - 3 times ethoxylated | 3.0 | — | — |
| Alkyl ethoxy propoxy nonionic surfactant | — | 1.5 | — |
| Suds suppressor | 2.0 | — | — |
| Olin SLF 18 nonionic surfactant | — | — | 2.0 |
| Sulfate (Balance 100%) | | | |

EXAMPLE 2

Compact high density (0.96 Kg/l) dishwashing detergent compositions A to F in accordance with the invention:

| Component | A | B | C | D | E | F |
|---|---|---|---|---|---|---|
| STPP | — | 51.4 | 51.4 | — | — | 44.3 |
| Citrate | 17.05 | — | — | 49.6 | 40.2 | — |
| Carbonate | 17.50 | 14.0 | 20.0 | — | 8.0 | 33.6 |
| Bicarbonate | — | — | — | 26.0 | — | — |
| Silicate | 14.81 | 15.0 | 8.0 | — | 25.0 | 3.6 |
| Metasilicate | 2.50 | 4.5 | 4.5 | — | — | — |
| PB1 | 9.74 | 7.79 | 7.79 | — | — | — |
| PB4 | — | — | — | 9.6 | — | — |
| Percarbonate | — | — | — | — | 11.8 | 4.8 |
| Nonionic | 2.00 | 1.50 | 1.50 | 2.6 | 1.9 | 5.9 |
| TAED | 2.39 | — | — | 3.8 | — | 1.4 |
| HEDP | 1.00 | — | — | — | — | — |
| DETPMP | 0.65 | — | — | — | — | — |
| Mn TACN | — | — | — | — | 0.008 | — |
| NOBS | — | 2.40 | — | — | — | — |
| PAAC | — | — | 0.008 | — | — | — |
| Paraffin | 0.50 | 0.38 | 0.38 | 0.6 | — | — |
| Protease[1] | 0.1 | 0.06 | 0.05 | 0.03 | 0.07 | 0.01 |
| Amylase | 1.5 | 1.5 | 1.5 | 2.6 | 2.1 | 0.8 |
| BTA | 0.30 | 0.22 | 0.22 | 0.3 | 0.3 | 0.3 |
| Polycarboxylate | 6.0 | — | — | — | 4.2 | 0.9 |
| Perfume | 0.2 | 0.12 | 0.12 | 0.2 | 0.2 | 0.2 |
| Sulfate/Water | 20.57 | 1.97 | 2.97 | 3.6 | 4.5 | 3.9 |
| pH (1% solution) | 11.0 | 11.0 | 11.3 | 9.6 | 10.8 | 10.9 |

EXAMPLE 3

Granular dishwashing detergent compositions examples A to F of bulk density 1.02 Kg/L in accordance with the invention:

| Component | A | B | C | D | E | F |
|---|---|---|---|---|---|---|
| STPP | 30.00 | 33.5 | 27.9 | 29.62 | 33.8 | 22.0 |
| Carbonate | 30.50 | 30.50 | 30.5 | 23.00 | 34.5 | 45.0 |
| Silicate | 7.40 | 7.50 | 12.6 | 13.3 | 3.2 | 6.2 |
| Metasilicate | — | 4.5 | | | | |
| Percarbonate | — | — | | — | 4.0 | |
| PB1 | 4.4 | 4.5 | 4.3 | — | — | |
| NaDCC | — | — | | 2.00 | — | 0.9 |
| Nonionic | 1.0 | 0.75 | 1.0 | 1.90 | 0.7 | 0.5 |
| TAED | 1.00 | — | | — | — | — |
| NOBS | — | — | — | — | 2.0 | — |
| PAAC | — | 0.004 | | — | — | |
| Paraffin | 0.25 | 0.25 | | — | — | |
| Protease[1] | 0.05 | 0.06 | 0.025 | 0.1 | 0.02 | 0.07 |
| Amylase | 0.38 | 0.64 | 0.46 | — | 0.6 | |

-continued

| Component | A | B | C | D | E | F |
|---|---|---|---|---|---|---|
| BTA | 0.15 | 0.15 | — | — | 0.2 | — |
| Perfume | 0.2 | 0.2 | 0.05 | 0.1 | 0.2 | — |
| Sulfate/water | 23.45 | 16.87 | 22.26 | 30.08 | 21.7 | 25.4 |
| pH (1% solution) | 10.80 | 11.3 | 11.0 | 10.70 | 11.5 | 10.9 |

EXAMPLE 4

Tablet detergent composition examples A to H in accordance with the present invention are prepared by compression of a granular dishwashing detergent composition at a pressure of 13 KN/cm$^2$ using a standard 12 head rotary press:

| Component | A | B | C | D | E | F | G | H |
|---|---|---|---|---|---|---|---|---|
| STPP | — | 48.8 | 54.7 | 38.2 | — | 52.4 | 56.1 | 36.0 |
| Citrate | 20.0 | — | — | — | 35.9 | — | — | — |
| Carbonate | 20.0 | 5.0 | 14.0 | 15.4 | 8.0 | 23.0 | 20.0 | 28.0 |
| Silicate | 15.0 | 14.8 | 15.0 | 12.6 | 23.4 | 2.9 | 4.3 | 4.2 |
| Protease[1] | 0.05 | 0.09 | 0.05 | 0.03 | 0.06 | 0.03 | 0.03 | 0.1 |
| Amylase | 1.5 | 1.5 | 1.5 | 0.85 | 1.9 | 0.4 | 2.1 | 0.3 |
| PB1 | 14.3 | 7.8 | 11.7 | 12.2 | — | — | 6.7 | 8.5 |
| PB4 | — | — | — | — | 22.8 | — | 3.4 | — |
| Percarbonate | — | — | — | — | — | 10.4 | — | — |
| Nonionic | 1.5 | 2.0 | 2.0 | 2.2 | 1.0 | 4.2 | 4.0 | 6.5 |
| PAAC | — | — | 0.016 | 0.009 | — | — | — | — |
| MnTACN | — | — | — | — | 0.007 | — | — | — |
| TAED | 2.7 | 2.4 | — | — | — | 2.1 | 0.7 | 1.6 |
| HEDP | 1.0 | — | — | 0.93 | — | 0.4 | 0.2 | — |
| DETPMP | 0.7 | — | — | — | — | — | — | — |
| Paraffin | 0.4 | 0.5 | 0.5 | 0.55 | — | — | 0.5 | — |
| BTA | 0.2 | 0.3 | 0.3 | 0.33 | 0.3 | 0.3 | 0.3 | — |
| Polycarboxylate | 4.0 | — | — | — | 4.9 | 0.6 | 0.8 | — |
| PEG | — | — | — | — | — | 2.0 | — | 2.0 |
| Glycerol | — | — | — | — | — | 0.4 | — | 0.5 |
| Perfume | — | — | 0.05 | 0.20 | — | 0.2 | 0.2 | 0.2 |
| Sulfate/water | 17.4 | 14.7 | — | 15.74 | — | — | — | 11.3 |
| weight of tablet | 20 g | 25 g | 20 g | 30 g | 18 g | 20 g | 25 g | 24.0 |
| pH (1% solution) | 10.7 | 10.60 | 10.7 | 10.7 | 10.9 | 11.2 | 11.0 | 10.8 |

EXAMPLES 5

Granular Fabric Cleaning Compositions

| Components | A | B |
|---|---|---|
| Linear alkyl benzene sulphonate | 11.4 | 10.70 |
| Tallow alkyl sulphate | 1.80 | 2.40 |
| C$_{14-15}$ alkyl sulphate | 3.00 | 3.10 |
| C$_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Protease[1] | 0.1 | 0.01 |
| Lipase | 0.36 | 0.40 |
| Amylase | 0.30 | 0.30 |
| Sodium silicate | 2.00 | 2.50 |

EXAMPLES 5-continued

Granular Fabric Cleaning Compositions

| Components | A | B |
|---|---|---|
| Sodium sulphate | 3.50 | 5.20 |
| Polyvinyl pyrrolidone | 0.30 | 0.50 |
| Perborate | 0.5 | 1 |
| TAED | 1.0 | — |
| NOBS | — | 1.0 |
| Phenol sulphonate | 0.1 | — |
| Peroxidase | 0.1 | 0.1 |
| Minors | Up to 100 | Up to 100 |

EXAMPLES 6

Granular Fabric Cleaning Compositions

| Components | A | B |
|---|---|---|
| Sodium linear C$_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| TAED | 3.0 | — |
| NOBS | — | 2.4 |
| Boric acid | 4.0 | — |
| Perborate | 0.5 | 1 |
| Phenol sulphonate | 0.1 | — |
| Protease[1] | 0.02 | 0.05 |
| Fillers (e.g., silicates; carbonates; perfumes; water) | Up to 100 | Up to 100 |

EXAMPLE 7

Compact Granular Fabric Cleaning Composition

| Components | Weight % |
|---|---|
| Alkyl Sulphate | 8.0 |
| Alkyl Ethoxy Sulphate | 2.0 |
| Mixture of C25 and C45 alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly (4-vinylpyridine)-N-oxide | 0.1 |
| Copolymer of vinylimidazole and vinylpyrrolidone | 0.1 |
| PEG2000 | 0.2 |
| Protease[1] | 0.03 |
| Lipase | 0.2 |
| Cellulase | 0.2 |
| TAED | 6.0 |
| Percarbonate | 22.0 |
| Ethylene diamine disuccinic acid | 0.3 |
| Suds suppressor | 3.5 |
| Disodium-4,4'-bis (2-morpholino-4-anilino-s-triazin-6-ylamino) stilbene-2,2'-disulphonate | 0.25 |
| Disodium-4,4'-bis (2-sulfostyril) biphenyl | 0.05 |
| Water, Perfume and Minors | Up to 100 |

EXAMPLE 8

Granular Fabric Cleaning Composition

| Component | Weight % |
|---|---|
| Linear alkyl benzene sulphonate | 7.6 |
| $C_{16}$–$C_{18}$ alkyl sulfate | 1.3 |
| $C_{14-15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| TAED | 5.0 |
| Smectite clay | 10.0 |
| Poly (oxy ethylene) (MW 300,000) | 0.3 |
| Protease[1] | 0.02 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 9

Granular Fabric Cleaning Composition

| Component | Weight % |
|---|---|
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.6 |
| Zeolite | 20.2 |

EXAMPLE 9-continued

Granular Fabric Cleaning Composition

| Component | Weight % |
|---|---|
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Protease[1] | 0.1 |
| Lipase | 0.36 |
| Cellulase | 0.13 |
| Perborate tetrahydrate | 11.64 |
| Perborate monohydrate | 8.7 |
| TAED | 5.0 |
| Diethylene triamine penta methyl phosphonic acid | 0.38 |
| Magnesium sulfate | 0.40 |
| Brightener | 0.19 |
| Perfume, silicone, suds suppressors | 0.85 |
| Minors | Up to 100 |

EXAMPLE 10

Granular Fabric Cleaning Composition

| Component | A | B | C |
|---|---|---|---|
| Base Granule Components | | | |
| LAS/AS/AES (65/35) | 9.95 | — | — |
| LAS/AS/AES (70/30) | — | 12.05 | 7.70 |
| Alumino silicate | 14.06 | 15.74 | 17.10 |
| Sodium carbonate | 11.86 | 12.74 | 13.07 |
| Sodium silicate | 0.58 | 0.58 | 0.58 |
| NaPAA Solids | 2.26 | 2.26 | 1.47 |
| PEG Solids | 1.01 | 1.12 | 0.66 |
| Brighteners | 0.17 | 0.17 | 0.11 |
| DTPA | — | — | 0.70 |
| Sulfate | 5.46 | 6.64 | 4.25 |
| DC-1400 Deaerant | 0.02 | 0.02 | 0.02 |
| Moisture | 3.73 | 3.98 | 4.33 |
| Minors | 0.31 | 0.49 | 0.31 |
| B.O.T. Spray-on | | | |
| Nonionic surfactant | 0.50 | 0.50 | 0.50 |
| Agglomerate Components | | | |
| LAS/AS (25/75) | 11.70 | 9.60 | 10.47 |
| Alumino silicate | 13.73 | 11.26 | 12.28 |
| Carbonate | 8.11 | 6.66 | 7.26 |
| PEG 4000 | 0.59 | 0.48 | 0.52 |
| Moisture/Minors | 4.88 | 4.00 | 4.36 |
| Functional Additives | | | |
| Sodium carbonate | 7.37 | 6.98 | 7.45 |
| Perborate | 1.03 | 1.03 | 2.56 |
| AC Base Coating | — | 1.00 | — |
| NOBS | — | — | 2.40 |
| Soil release polymer | 0.41 | 0.41 | 0.31 |
| Cellulase | 0.33 | 0.33 | 0.24 |
| Protease[1] | 0.1 | 0.05 | 0.15 |
| AE-Flake | 0.40 | 0.40 | 0.29 |
| Liquid Spray-on | | | |
| Perfume | 0.42 | 0.42 | 0.42 |
| Noionic spray-on | 1.00 | 1.00 | 0.50 |
| Minors | Up to 100 | | |

EXAMPLE 11

Granular Fabric Cleaning Composition

|  | A | B |
|---|---|---|
| Surfactant | | |
| NaLAS | 6.40 | — |
| KLAS | — | 9.90 |
| AS/AE3S | 6.40 | 4.39 |
| TAS | 0.08 | 0.11 |
| C24AE5 | 3.48 | — |
| Genagen | — | 1.88 |
| N-cocoyl N-methyl glucamine (lin) | 1.14 | 2.82 |
| $C_{8-10}$ dimethyl hydroxyethyl ammonium chloride | 1.00 | 1.40 |
| Builder | | |
| Zeolite | 20.59 | 13.39 |
| SKS-6 | 10.84 | 10.78 |
| Citric Acid | 2.00 | — |
| Buffer | | |
| Carborate | 9.60 | 12.07 |
| Bicarbonate | 2.00 | 2.00 |
| Sulphate | 2.64 | — |
| Silicate | 0.61 | 0.16 |
| Polymer | | |
| Acrylic acid/maleic acid copolymer (Na) | 1.17 | 1.12 |
| CMC | 0.45 | 0.24 |
| Polymer | 0.34 | 0.18 |
| Hexamethylene-diamine tetra-E24 ethoxylate, diquaternized with methyl chloride | 1.00 | 1.00 |
| Enzyme | | |
| Protease[1] (% pure enzyme) | 0.03 | 0.03 |
| Cellulase | 0.26 | 0.26 |
| Amylase | 0.65 | 0.73 |
| Lipase | 0.27 | 0.15 |
| Bleach | | |
| TAED (100%) | 3.85 | 3.50 |
| Phenolsulfonate ester of N-nonanoyl-6-aminocaproic acid | — | 2.75 |
| Percarbonate | 16.20 | 18.30 |
| HEDP | 0.48 | 0.48 |
| EDDS | 0.30 | 0.30 |
| Miscellaneous | | |
| Malic particle | — | 2.20 + bicarb |
| Brightener 15/49 | 0.077/0.014 | 0.07/0.014 |
| Zinc phthalocyanine sulfonate | 0.0026 | 0.0026 |
| Polydimethylsiloxane with trimethylsilyl end blocking units | 0.25 | 0.24 |
| Soap | — | 1.00 |
| Perfume | 0.45 | 0.55 |
| TOTAL | 100 | 100 |

EXAMPLE 12

Granular Fabric Cleaning Composition

|  | A | B |
|---|---|---|
| Surfactant | | |
| NaLAS | 6.8 | 0.4 |
| KLAS | — | 10.9 |
| FAS | 0.9 | 0.1 |
| AS | 0.6 | 1.5 |
| C25AE3S | 0.1 | — |
| AE5 | 4.2 | — |
| N-Cocoyl-N-Methyl Glucamine | — | 1.8 |
| Genagen | — | 1.2 |
| $C_{8-10}$ dimethyl hydroxyethyl ammonium chloride | — | 1.0 |
| Builder | | |
| SKS-6 | 3.3 | 9.0 |
| Zeolite | 17.2 | 18.9 |
| Citric Acid | 1.5 | — |
| Buffer | | |
| Carbonate | 21.1 | 15.0 |
| Sodium Bicarbonate | — | 2.6 |
| Sulphate | 15.2 | 5.5 |
| Malic Acid | — | 2.9 |
| Silicate | 0.1 | — |
| Polymer | | |
| Acrylic acid/maleic acid copolymer (Na) | 2.2 | 0.9 |
| Hexamethylene-diamine tetra-E24 ethoxylate, diquaternized with methyl chloride | 0.5 | 0.7 |
| Polymer | 0.1 | 0.1 |
| CMC | 0.2 | 0.1 |
| Enzymes | | |
| Protease[1] (% pure enzyme) | 0.02 | 0.05 |
| Lipase | 0.18 | 0.14 |
| Amylase | 0.64 | 0.73 |
| Cellulase | 0.13 | 0.26 |
| Bleach | | |
| TAED | 2.2 | 2.5 |
| Phenolsulfonate ester of N-nonanoyl-6-aminocaproic acid | — | 1.96 |
| Sodium Percarbonate | — | 13.1 |
| PB4 | 15.6 | — |
| EDDS | 0.17 | 0.21 |
| MgSO4 | 0.35 | 0.47 |
| HEDP | 0.15 | 0.34 |
| Brightener | 0.06 | 0.04 |
| Zinc phthalocyanine sulfonate | 0.0015 | 0.0020 |
| Polydimethylsiloxane with trimethylsilyl end blocking units | 0.04 | 0.14 |
| Soap | 0.5 | 0.7 |
| Perfume | 0.35 | 0.45 |
| Speckle | 0.5 | 0.6 |

EXAMPLES 13

Granular laundry detergent compositions 13A–C in accordance with the present invention are of particular utility under European machine wash conditions:

| Component | A | B | C |
|---|---|---|---|
| LAS | 7.0 | 5.61 | 4.76 |
| TAS | — | — | 1.57 |
| C45AS | 6.0 | 2.24 | 3.89 |
| C25E3S | 1.0 | 0.76 | 1.18 |
| C45E7 | — | — | 2.0 |
| C25E3 | 4.0 | 5.5 | — |
| QAS | 0.8 | 2.0 | 2.0 |

-continued

| Component | A | B | C |
|---|---|---|---|
| STPP | — | — | — |
| Zeolite A | 25.0 | 19.5 | 19.5 |
| Citric acid | 2.0 | 2.0 | 2.0 |
| NaSKS-6 | 8.0 | 10.6 | 10.6 |
| Carbonate I | 8.0 | 10.0 | 8.6 |
| MA/AA | 1.0 | 2.6 | 1.6 |
| CMC | 0.5 | 0.4 | 0.4 |
| PB4 | — | 12.7 | — |
| Percarbonate | — | — | 19.7 |
| TAED | — | 3.1 | 5.0 |
| Citrate | 7.0 | — | — |
| DTPMP | 0.25 | 0.2 | 0.2 |
| HEDP | 0.3 | 0.3 | 0.3 |
| QEA 1 | 0.9 | 1.2 | 1.0 |
| Protease[1] | 0.02 | 0.05 | 0.035 |
| Lipase | 0.15 | 0.25 | 0.15 |
| Cellulase | 0.28 | 0.28 | 0.28 |
| Amylase | 0.4 | 0.7 | 0.3 |
| PVPI/PVNO | 0.4 | — | 0.1 |
| Photoactivated bleach (ppm) | 15 ppm | 27 ppm | 27 ppm |
| Brightener 1 | 0.08 | 0.19 | 0.19 |
| Brightener 2 | — | 0.04 | 0.04 |
| Perfume | 0.3 | 0.3 | 0.3 |
| Effervescent granules (malic acid 40%, sodium bicarbonate 40%, sodium carbonate 20%) | 15 | 15 | 5 |
| Silicone antifoam | 0.5 | 2.4 | 2.4 |
| Minors/inerts to 100% | | | |

EXAMPLE 14

The following formulations are examples of compositions in accordance with the invention, which may be in the form of granules or in the form of a tablet.

| Component | 14 |
|---|---|
| C45 AS/TAS | 3.0 |
| LAS | 8.0 |
| C25AE3S | 1.0 |
| NaSKS-6 | 9.0 |
| C25AE5/AE3 | 5.0 |
| Zeolite A | 10.0 |
| SKS-6 (I) (dry add) | 2.0 |
| MA/AA | 2.0 |
| Citric acid | 1.5 |
| EDDS | 0.5 |
| HEDP | 0.2 |
| PB1 | 10.0 |
| NACA OBS | 2.0 |
| TAED | 2.0 |
| Carbonate | 8.0 |
| Sulphate | 2.0 |
| Amylase | 0.3 |
| Lipase | 0.2 |
| Protease[1] | 0.02 |
| Minors (Brightener/SRP1/CMC/Photobleach/MgSO4/PVPVI/Suds suppressor/PEG) | 0.5 |
| Perfume | 0.5 |

EXAMPLE 15

Liquid Fabric Cleaning Compositions

| Component | EXAMPLE No. A | B |
|---|---|---|
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Protease[1] | 0.01 | 0.02 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100% | |

EXAMPLE 16

Liquid Fabric Cleaning Compositions

| Component | EXAMPLE No. 17 |
|---|---|
| NaLAS (100% am) | 16 |
| Neodol | 21.5 |
| EDDS | 1.2 |
| Dispersant | 1.3 |
| Perborate | 12 |
| Phenolsulfonate ester of N-nonanoyl-6-aminocaproic acid | 6 |
| Protease[1] (% pure enzyme) | 0.03 |
| Cellulase | 0.03 |
| Solvent (BPP) | 18.5 |
| Polymer | 0.1 |
| Carbonate | 10 |
| FWA 15 | 0.2 |
| $TiO_2$ | 0.5 |
| PEG 8000 | 0.4 |
| Perfume | 1.0–1.2 |
| Suds suppressor | 0.06 |
| Waters and minors | up to 100% |

EXAMPLE 17

Two-layer Effervescent Denture Cleansing Tablet

| Component | Example No. A | B | C | D |
|---|---|---|---|---|
| Acidic Layer | | | | |
| Protease[1] | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| Tetracetylethylene diamine | 7.0 | 7.0 | 7.00 | 7.00 |
| Flavor | 1.0 | 1.0 | 1.00 | 1.00 |

EXAMPLE 17-continued

Two-layer Effervescent Denture Cleansing Tablet

| | Example No. | | | |
|---|---|---|---|---|
| Component | A | B | C | D |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

EXAMPLE 18

Granular laundry detergent compositions 18 A–E are of particular utility under Japanese machine wash conditions and are prepared in accordance with the invention:

| Component | A | B | C | D | E |
|---|---|---|---|---|---|
| LAS | 23.57 | 23.57 | 21.67 | 21.68 | 21.68 |
| FAS | 4.16 | 4.16 | 3.83 | 3.83 | 3.83 |
| Nonionic surfactant | 3.30 | 3.30 | 2.94 | 3.27 | 3.27 |
| Bis (hydroxyethyl) methyl alkyl alkyl ammonium chloride | 0.47 | 0.47 | 1.20 | 1.20 | 1.20 |
| SKS-6 | 7.50 | 7.5C | 5.17 | 5.76 | 5.06 |
| Polyacrylate copolymer (MW 11000) (maleic/acrylate ratio of 4:6) | 7.03 | 7.03 | 14.36 | 14.36 | 14.36 |
| Zeolite | 11.90 | 11.40 | 10.69 | 11.34 | 11.34 |
| Carbonate | 14.90 | 14.82 | 11.71 | 11.18 | 11.18 |
| Silicate | 12.00 | 12.00 | 12.37 | 12.38 | 12.38 |
| Protease[1] | 0.016 | 0.016 | 0.046 | 0.046 | 0.046 |
| Lipase | — | — | 0.28 | — | — |
| Amylase | — | — | 0.62 | — | — |
| Cellulase | — | — | 0.48 | — | 0.70 |

-continued

| Component | A | B | C | D | E |
|---|---|---|---|---|---|
| NOBS | 3.75 | 3.75 | 2.70 | 2.70 | 2.70 |
| PB1 | 3.53 | — | 2.60 | — | — |
| Sodium percarbonate | — | 4.21 | — | 3.16 | 3.16 |
| SRP | 0.52 | 0.52 | 0.70 | 0.70 | 0.70 |
| Brightener | 0.31 | 0.31 | 0.28 | 0.28 | 0.50 |
| AE-coflake | 0.17 | 0.20 | 0.17 | 0.17 | 0.17 |
| Polydimethyl-siloxane | — | — | 0.68 | 0.68 | 0.68 |
| Perfume | 0.06 | 0.06 | 0.08 | — | — |
| Perfume | — | — | — | 0.23 | 0.23 |
| Hydrophobic precipitate silica | 0.30 | 0.30 | 0.30 | 0.30 | 0.30 |
| PEG4000 | 0.19 | 0.19 | 0.17 | 0.17 | 0.17 |
| Minors/inerts to 100% | | | | | |

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

The compositions of the present invention can be suitably prepared by any process chosen by the formulator, non-limiting examples of which are described in U.S. Pat. Nos. 5,691,297; 5,574,005; 5,569,645; 5,565,422; 5,516,448; 5,489,392; and 5,486,303.

In addition to the above examples, the bleaching compositions of the present invention can be formulated into any suitable laundry detergent composition, non-limiting examples of which are described in U.S. Pat. Nos. 5,679,630; 5,565,145; 5,478,489; 5,476,507; 5,466,802; 5,460,752; 5,458,810; 5,458,809; and 5,288,431.

Having described the invention in detail with reference to preferred embodiments and the examples, it will be clear to those skilled in the art that various changes and modifications may be made without departing from the scope of the invention and the invention is not to be considered limited to what is described in the specification.

What is claimed is:

1. A bleaching composition comprising:
(a) an effective amount of a protease variant wherein said protease variant includes a substitution of an amino acid residue with another naturally occurring amino acid residue at an amino acid residue position corresponding to position 103 of Bacillus amyloliquefaciens subtilisin in combination with a substitution of an amino acid residue with another naturally occurring amino acid residue at one or more amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of Bacillus amyloliquefaciens subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 of Bacillus amyloliquefaciens subtilisin;
(b) a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and
(c) one or more cleaning adjunct materials further wherein said protease variant includes substitutions of the amino acid residues at one or more positions selected from the group consisting of:
1) position 62 and at one or more of the following positions 103, 104, 109, 159, 213, 232, 236, 245, 248 and 252;
2) position 212 and at one or more of the following positions 12, 98, 102, 103, 104, 159, 232, 236, 245, 248 and 252;
3) position 230 and at one or more of the following positions 68, 103, 104, 159, 232, 236 and 245;
4) position 232 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;
5) position 232 and at one or more of the following positions 103, 104, 236 and 245;
6) positions 232 and 103 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;
7) positions 232 and 104 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;
8) positions 232 and 236 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;
9) positions 232 and 245 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;
10) positions 232, 103, 104, 236 and 245 and at one or more of the following positions 12, 61, 62, 68, 76, 97, 98, 101, 102, 103, 104, 109, 130, 131, 159, 183, 185, 205, 209, 210, 212, 213, 217, 230, 236, 245, 248, 252, 257, 260, 270 and 275;
11) position 252 and at one or more of the following positions 12, 61, 62, 68, 97, 98, 101, 102, 103, 104, 109, 130, 131, 159, 183, 185, 210, 212, 213, 217, 230, 236, 245, 248, and 270;
12) position 252 and at one or more of the following positions 103, 104, 236 and 245;
13) positions 252 and 103 and at one or more of the following positions 12, 61, 62, 68, 97, 98, 101, 102, 103, 104, 109, 130, 131, 159, 183, 185, 210, 212, 213, 217, 232, 236, 245, 248, and 270;
14) positions 252 and 104 and at one or more of the following positions 12, 61, 62, 68, 97, 98, 101, 102, 103, 104, 109, 130, 131, 159, 183, 185, 210, 212, 213, 217, 232, 236, 245, 248, and 270;
15) positions 252 and 236 and at one or more of the following positions 12, 61, 62, 68, 97, 98, 101, 102, 103, 104, 109, 130, 131, 159, 183, 185, 210, 212, 213, 217, 232, 236, 245, 248, and 270;
16) positions 252 and 245 and at one or more of the following positions 12, 61, 62, 68, 97, 98, 101, 102, 103, 104, 109, 130, 131, 159, 183, 185, 210, 212, 213, 217, 232, 236, 245, 248, and 270;
17) positions 252, 103, 104, 236 and 245 and at one or more of the following positions 12, 61, 62, 68, 97, 98, 101, 102, 103, 104, 109, 130, 131, 159, 183, 185, 210, 212, 213, 217, 232, 236, 245, 248, and 270; and
18) position 257 and at one or more of the following positions 68, 103, 104, 205, 209, 210, 232, 236, 245 and 275.

2. The bleaching composition according to claim 1 wherein said protease variant is derived from a Bacillus subtilisin.

3. The bleaching composition according to claim 1 wherein said protease variant includes substitutions of the amino acid residues at position 103 and at one or more of the following positions 236 and 246 and at one or more of the following positions 12, 61, 62, 68, 76, 97, 98, 101, 102, 104, 109, 130, 131, 159, 183, 185, 205, 209, 210, 211, 212, 213, 215, 217, 230, 232, 248, 252, 257, 260, 270 and 275 or at positions 103 and 245 and at one or more of the following positions 12, 61, 62, 68, 76, 97, 98, 101, 102, 104, 109, 130, 131, 159, 170, 183, 185, 205, 209, 210, 211, 212, 213, 215, 217, 222, 230, 232, 248, 252, 257, 260, 261, 270 and 275, and at one or more of the following positions 12, 61, 62, 68, 76, 97, 98, 101, 102, 104, 109, 130, 131, 159, 183, 185, 205, 209, 210, 211, 212, 213, 215, 217, 230, 232, 248, 252, 257, 260, 270 and 275.

4. The bleaching composition according to claim 1 wherein said protease variant includes a substitution set selected from the group consisting of:

12/102/103/104/159/212/232/236/245/248/252;

12/76/103/104/130/170/185/222/243/245;

12/76/103/104/130/222/245/261; 12/76/103/104/222/245;

12/76/103/104/222/245;

61/68/103/104/159/232/236/245/248/252; 62/103/104/159/213/232/236/245/248/252;

62/103/104/109/159/213/232/236/245/248/252; 62/103/104/159/232/236/245/248/252;

62/101/103/104/159/212/213/232/236/245/248/252;

62/103/104/130/159/213/232/236/245/248/252;

68/103/104/159/232/236/245/248/252/270;

68/103/104/159/185/232/236/245/248/252; 68/103/104/159/210/232/236/245/248/252;

68/103/104/159/185/210/232/236/245/248/252;

68/103/104/159/213/232/236/245/248/252;

68/103/104/159/230/232/236/245; 68/76/103/104/159/209/232/236/245;

68/103/104/232/236/245/248/257/275; 68/103/104/213/232/236/245/248/252;

68/103/104/159/232/236/245/248/252; 68/103/104/159/209/232/236/245;

68/76/103/104/159/236; 68/76/103/104/159/236/245;

68/76/103/104/159/232/236/245; 68/103/104/159/232/236/245/252;

68/103/104/159/232/236/245; 68/103/104/159/232/236/245/257;

68/76/103/104/159/211/232/236/245; 68/76/103/104/159/215/232/236/245;

68/103/104/159/210/232/236/245; 68/103/104/159/213/232/236/245/260;

68/76/103/104/159/213/232/236/245/260; 68/103/104/159/236;

68/76/103/104/159/210/232/236/245/260; 68/103/104/159/236/245;

68/103/104/159/183/232/236/245/248/252; 68/76/103/104/159/236/245;

68/103/104/232/236/245/257/275; 68/103/104/159/213/232/236/245;

76/103/222/245; 76/103/159/232/236/245;

76/103/104/159/213/232/236/245/260; 76/103/104/159;

76/103/104/131/159/232/236/245/248/252; 76/103/104/222/245;

97/103/104/159/232/236/245/248/252;

98/102/103/104/159/212/232/236/245/248/252; 98/103/104/159/232/236/245/248/252;

101/103/104/159/232/236/245/248/252; 102/103/104/159/232/236/245/248/252;

103/104/159/232/236/245; 103/104/159/232/236/245/248/252;

103/104/159/205/209/232/236/245/257 103/104/159/232/245/248/252;

103/104/159/205/209/210/232/236/245/257; 103/104/159/213/232/236/245/248/252;

103/104/159/217/232/236/245/248/252; 103/104/130/159/232/236/245/248/252;

103/104/159/230/236/245; 103/104/159/236/245;

103/104/159/248/252/270; 103/104/131/159/232/236/245/248/252;

103/104/159/205/209/232/236/245; and 103/104/159/232/236/245/257.

5. The bleaching composition according to claim 4 wherein said protease variant includes a substitution set selected from the group consisting of:

12R/76D/103A/104T/130T/222S/245R;

12R/76D/103A/104I/222S/245R;

12R/102A/103A/104I/159D/212G/232V/236H/245R/248D/252K;

12R/76D/103A/104T/130G/222S/245R/261D;

12R/76D/103A/104T/130G/170S/185D/222S/243D/245R;

61E/68A/103A/104I/159D/232V/236H/245R/248D/252K;

62D/103A/104I/109R/159D/213R/232V/236H/245R/248D/252K;

62D/103A/104I/159D/213R/232V/236H/245R/248D/252K;

62D/103A/104I/159D/232V/236H/245R/248D/252K;

62D/103A/104I/130G/159D/213R/232V/236H/245R/248D/252K;

62D/101G/103A/104I/159D/212G/213R/232V/236H/245R/248D/252K;

68A/76D/103A/104I/159D/213R/232V/236H/245R/260A;

68A/103A/104I/159D/236H;

68A/103A/104I/159D/236H/245R;

68A/76D/103A/104I/159D/210I/232V/236H/245R/260A;

68A/103A/104I/159D/183D/232V/236H/245R/248D/252K;

68A/103A/104I/159D/209W/232V/236H/245R;

68A/76D/103A/104I/159D/211R/232V/236H/245R;

68A/76D/103A/104I/159D/215R/232V/236H/245R;

68A/103A/104I/159D/213R/232V/236H/245R/260A;

68A/76D/103A/104I/159D/236H;

68A/76D/103A/104I/159D/236H/245R;

68A/76D/103A/104I/159D/232V/236H/245R;

68A/103A/104I/159D/232V/236V/245R/252K;

68A/103A/104I/159D/232V/236H/245R;

68A/103A/104I/159D/232V/236H/245R/257V;

68A/103A/104I/159D/185D/232V/236H/245R/248D/252K;

68A/103A/104I/159D/210L/232V/236H/245R/248D/252K;

68A/103A/104I/159D/185D/210L/232V/236H/245R/248D/252K;

68A/103A/104I/159D/213E/232V/236H/245R/248D/ 252K;
68A/103A/104I/159D/230V/232V/236H/245R;
68A/76D/103A/104I/159D/209W/232V/236H/245R;
68A/103A/104I/232V/236H/245R/248D/257V/275H;
68A/103A/104I/232V/236H/245R/257V/275H;
68A/103A/104I/213E/232V/236H/245R/248D/252K;
68A/103A/104I/159D/232V/236H/245R/248D/252K;
68A/103A/104I/159D/210I/232V/236H/245R;
68A/103A/104I/159D/210L/232V/236H/245R;
68A/103A/104I/159D/213G/232V/236H/245R;
68A/103A/104I/159D/232V/236H/245R/248D/252K/ 270A;
76D/103A/222S/245R;
76D/103A/104I/159D/232V/236H/245R;
76D/103A/104I/159D;
76D/103A/104I/222S/245R;
76D/103A/104I/159D/232V/236V/245H/248R/252K;
76D/103A/104I/159D/213R/232V/236H/245R/260A;
97E/103A/104I/159D/232V/236H/245R/248D/252K;
98L/103A/104I/159D/232V/236H/245R/248D/252K;
98L/102A/103A/104I/159D/212G/232V/236H/245R/ 248D/252K;
101G/103A/104I/159D/232V/236H/245R/248D/252K;
102A/103A/104I/159D/232V/236H/245R/248D/252K;
103A/104I/159D/232V/236H/245R/248D/252K;
103A/104I/159D/213R/232V/236H/245R/248D/252K;
103A/104I/130G/159D/232V/236H/245R/248D/252K;
103A/104I/159D/230V/236H/245R;
103A/104I/159D/217E/232V/236H/245R/248D/252K;
103A/104I/159D/236H/245R;
103A/104I/159D/248D/252K/270V;
103A/104I/159D/232V/236H/245R;
103A/104I/159D/205I/209W/232V/236H/245R;
103A/104I/159D/232V/236H/245R/257V;
103A/104I/159D/205I/209W/232V/236H/245R/257V;
103A/104I/131V/159D/232V/236H/245R/248D/252K;
103A/104I/159D/205I/209W/210I/232V/236H/245R/ 257V; and
103A/104I/159D/232V/245R/248D/252K.

6. The bleaching composition according to claim 1 wherein said bleaching agent is selected from the group consisting of:
(i) an organic peroxyacid selected from the group consisting of organic peroxyacids of the formula:

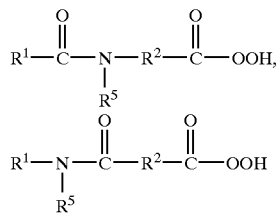

wherein $R^1$ is an alkyl, aryl, or alkaryl group containing from about 1 to about 14 carbon atoms, $R^2$ is an alkylene, arylene or alkarylene group containing from about 1 to about 14 carbon atoms, and $R^5$ is H or an alkyl, aryl, or alkaryl group containing from about 1 to about 10 carbon atoms; E-phthalimido peroxycaproic acids; and mixtures thereof; and (ii) a combination of a bleach activator and a peroxygen compound capable of yielding hydrogen peroxide that can react with the activator to form an organic peroxyacid in situ in a bleaching solution formed from the composition, wherein said bleach activator has the general formula:

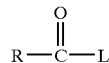

wherein R is an alkyl group containing from about 5 to about 18 carbon atoms wherein the longest linear alkyl chain extending from and including the carbonyl carbon contains from about 6 to about 10 carbon atoms and L is a leaving group, the conjugate acid of which has a pKa in the range of from about 4 to about 13; said bleach activator having the general formula:

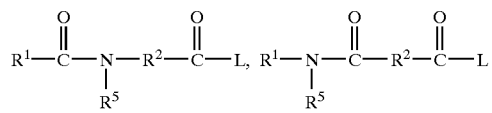

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, or alkaryl group containing from about 1 to about 10 carbon atoms, and L is a leaving group.

7. The bleaching composition according to claim 6 wherein $R^1$ is an alkyl group containing from about 7 to about 10 carbon atoms, $R^2$ contains from about 4 to about 5 carbon atoms, and wherein L to selected from the group consisting of:

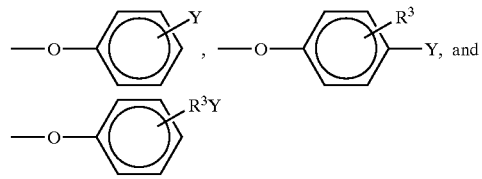

wherein $R^3$ is an alkyl chain containing from about 1 to about 8 carbon atoms, and Y is —$SO_3$—$M^+$ or —$CO_2^-M^+$ wherein M is sodium or potassium.

8. The bleaching composition according to claim 1 wherein said bleaching agent comprises a bleach activator selected from the group consisting of tetraacetyl ethylene diamine (TAED), benzoylcaprolactam (BzCL), 4-nitrobenzoylcaprolactam, 3-chlorobenzoyl-caprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters, 4-[N-(nonaoyl) amino hexanoyloxy]-benzene sulfonate sodium, salt (NACA-OBS), lauryloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA) and mixtures thereof, and further optionally comprises a bleach catalyst, preferably 3-(3,4-dihydroisoquinolinium)propane sulfonate.

9. The bleaching composition according to claim 1 wherein said bleaching agent comprises at least about 0.1% by weight of the bleaching agent of a peroxygen bleaching compound capable of yielding hydrogen peroxide in an aqueous liquor and at least 0.1% by weight of the bleaching agent of one or more bleach activators, wherein said bleach activators are members selected from the group consisting of:

(a) a bleach activator at the general formula:

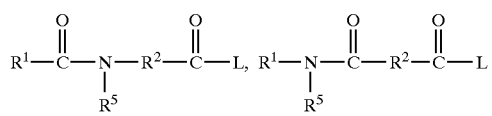

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, or alkaryl group containing from about 1 to about 10 carbon atoms, and L is a leaving group:

b) a benzoxazin-type bleach activator of the formula:

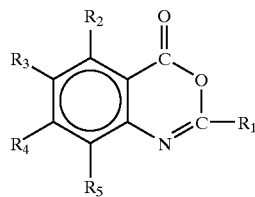

wherein R1 H, alkyl, alkaryl, aryl, arylalkyl, and wherein R2, R3, R4, and R5 may be the same or different substituents selected from H, halogen, alkyl, alkenyl, aryl, hydroxyl, alkoxyl, amino, alkylamino, —COOR$_6$, wherein $R^6$ is H or an alkyl group and carbonyl functions;

c) a N-acyl caprolactam bleach activator of the formula:

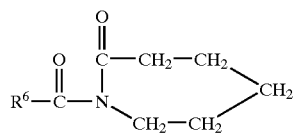

wherein $R^6$ is H or an alkyl, aryl, alkoxyaryl, or a group containing from 1 to 12 carbons; and d) mixture of a), b) and c).

10. The bleaching composition according to claim 1 wherein the corresponding carboxylic acid of the organic peroxyacid bleaching agent has a Hydrophillic-Lipophilic Balance value within the range of from about 3 to about 6.5.

11. The bleaching composition according to claim 1 wherein said cleaning adjunct materials are selected from the group consisting of surfactants, solvents, buffers, enzymes, soil release agents, clay soil removal agents, dispersing agents, brighteners, suds suppressors, fabric softeners, suds boosters, enzyme stabilizers, builders, other bleaching agents, dyes, perfumes, chelants and mixtures thereof.

12. The bleaching composition according to claim 11 wherein said cleaning adjunct materials comprise at least one detersive surfactant.

13. The bleaching composition according to claim 11 wherein the cleaning adjunct materials comprise at least about 0.1% surfactant by weight of the composition, said surfactant comprising materials selected from the group consisting of alkyl benzene sulfonates, primary alkyl sulfates, secondary alkyl sulfates, alkyl alkoxy sulfates, alkyl alkoxy carboxylates, alkyl polyglycosides and their corresponding sulfated polyglycosides, alpha-sulfonated fatty acid esters, alkyl and alkyl phenol alkoxylates, betaines and sulfobetaines, amine oxides, N-methyl gluamides, non-oinic primary alcohol ethoxylates, nonionic primary alcohol mixed ethoxy/propoxy, and mixtures thereof.

14. The bleaching composition according to claim 13 further comprising at least about 6% builder selected from the group consisting of zeolites, polycarboxylates, layered silicates, phosphates, and mixtures thereof.

15. The bleaching composition according to claim 11 wherein said cleaning adjunct materials comprise at least one detersive enzyme selected from the group consisting of cellulases, lipases, amylases, phospholipases, other proteases, peroxidases and mixtures thereof.

16. The bleaching composition according to claim 1 wherein said bleaching composition is a fabric bleaching composition, in the form of a liquid, granule, tablet, powder or bar, comprising at least about 5% surfactant and at least about 5% builder by weight of the composition.

17. The bleaching composition according to claim 1 wherein said bleaching composition is a fabric bleaching composition comprising:

(a) from about 0.0001% to about 10% by weight of said protease variant;

(b) from about 0.5% to about 20% by weight of said bleaching agent;

(c) at least about 5% by weight of a surfactant selected from the group consisting of alkyl benzene sulfonates, primary alkyl sulfates, secondary alkyl sulfates, alkyl alkoxy sulfates, alkyl alkoxy carboxylates, alkyl polyglycosides and their corresponding sulfated polyglycosides, alpha-sulfonated fatty acid esters, alkyl and alkyl phenol alkoxylates, betaines and sulfobetaines, amine oxides, N-methyl glucamides, nonionic primary alcohol ethoxylates, nonionic primary alcohol mixed ethoxy/propoxy, and, mixtures thereof; and (d) at least about 5% by weight of a builder selected from the group consisting of zeolites, polycarboxylates, layered silicates, phosphates, and mixtures thereof.

18. The bleaching composition according to claim 17 is in the form of a concentrated granular fabric bleaching composition comprising at least about 15% surfactant.

19. A method for cleaning fabric, said method comprising contacting a fabric in need of cleaning with a bleaching composition according to claim 16 or 17.

20. The bleaching composition according to claim 1 wherein said bleaching composition is a dishwashing bleaching composition, in the form of a liquid, granule, powder or tablet, comprising:

(a) from about 0.0001% to about 10% by weight of the dishwashing bleaching composition of said protease variant;

(b) from about 0.5% to about 20% by weight of the dishwashing bleaching composition of said bleaching agent (c) from about 0.1% to about 10% by weight of the dishwashing bleaching composition of a surfactant.

21. A method for cleaning dishes, said method comprising contacting a dish in need of cleaning with a bleaching composition according to claim 20.

22. The bleaching composition according to claim 1 wherein said bleaching composition is a personal cleansing composition comprising:
(a) from about 0.001% to about 5%, by weight of the personal cleansing composition of a protease variant wherein said proteases variant includes a substitution of an amino acid residue with another naturally occurring amino acid residue at an amino acid residue position corresponding to position 103 of *Bacillus amyloliquefaciens* subtilisin in combination with a substitution of an amino acid residue with another naturally occurring amino acid residue at one or more amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 66, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 148, 147, 158, 159, 160, 168, 167, 170, 173, 174, 177, 181, 182, 183, 184, 185, 188, 192, 194, 198, 203, 204, 205, 208, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 268, 259, 260, 261, 262, 263, 265, 268, 269, 270, 271, 272, 274 and 275 of *Bacillus amyloliquefaciens* subtilisin; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 218, 217, 218, 222, 280, 265 or 274 of *Bacillus amyloliquefaciens* subtillsin;
(b) from about 0.5% to about 20% by weight of the personal cleansing composition of a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and
(c) from about 0.1% to about 95% by weight of the personal cleansing composition of a surfactant system comprising one or more surfactants selected from the group consisting of anionic carboxylates, amine oxides, alkyl glucosides, glucose amides, alkyl sulfates, alkyl ether sulfates, acyl isethionates, alkyl sulfosuccinates, alkyl phosphate esters, ethoxylated phosphate esters, alkyl glyceryl ether sulfonates and mixtures thereof,
(d) optionally, from about 0.05% to about 50% by weight of the personal cleaning composition of an enzyme stabilizer.

23. The bleaching composition according to claim 22 wherein said surfactant is soap at a level of at least about 2% by weight of the bleaching composition.

24. The bleaching composition according to claim 23 wherein the ratio of soap to protease variant is from about 2,000:1 to about 8:1.

25. A method for personal cleansing, said method comprising contacting a part of the human or lower animal body in need of cleaning with a bleaching composition according to claim 22.

26. A method for pretreating a fabric in need of cleaning, said method comprising contacting said fabric prior to washing said fabric with an aqueous solution containing a surfactant with a bleaching composition according to claim 16 or 17.

27. The cleaning composition according to claim 1 wherein said protease variant includes a substitution set selected from the group consisting of:
12/102/103/104/159/212/232/236/245/248/252;
61/68/103/104/159/232/236/245/248/252;
62/103/104/130/159/213/232/236/245/248/252;
62/103/104/159/232/236/245/248/252;
62/103/104/109/159/213/232/236/245/248/252; 62/103/104/159/232/236/245/248/252;
62/101/103/104/159/212/213/232/236/245/248/252;
68/103/104/159/232/236/245/248/252/270;
68/103/104/159/185/232/236/245/248/252; 68/103/104/159/210/232/236/245/248/252;
68/103/104/159/185/210/232/236/245/248/252;
68/103/104/159/213/232/236/245/248/252;
68/103/104/159/230/232/236/245; 68/78/103/104/159/209/232/236/245;
68/103/104/232/236/245/248/257/275; 68/103/104/213/232/236/245/248/252;
68/103/104/159/232/236/245/248/252; 68/103/104/159/209/232/236/245;
68/76/103/104/159/232/236/245; 68/103/104/159/232/236/245/252;
68/103/104/159/232/236/245; 68/103/104/159/232/236/245/257;
68/76/103/104/159/211/232/236/245; 68/76/103/104/159/215/232/236/245;
68/103/104/159/210/232/236/245; 68/103/104/159/213/232/236/245/260;
68/76/103/104/159/213/232/236/245/260; 68/76/103/104/159/210/232/236/245/260;
68/103/104/159/183/232/236/245/248/252; 68/103/104/232/236/245/257/275;
68/103/104/159/213/232/236/245; 76/103/104/159/232/236/245;
76/103/104/159/213/232/236/245/260; 76/103/104/131/159/232/236/245/248/252;
97/103/104/159/232/236/245/248/252; 98/103/104/159/232/236/245/248/252;
98/102/103/104/159/212/232/236/245/248/252; 101/103/104/159/232/236/245/248/252;
102/103/104/159/232/236/245/248/252; 103/104/159/232/236/245;
103/104/159/248/252/270; 103/104/159/232/236/245/248/252;
103/104/159/205/209/232/236/245/257 103/104/159/232/245/248/252;
103/104/159/205/209/210/232/236/245/257; 103/104/159/213/232/236/245/248/252;
103/104/159/217/232/236/245/248/252; 103/104/130/159/232/236/245/248/252;
103/104/131/159/232/236/245/248/252; 103/104/159/205/209/232/236/245; and
103/104/159/232/236/245/257.

28. The cleaning composition according to claim 27 wherein said protease variant includes a substitution set selected from the group consisting of:
12R/102A/103A/104I/159D/212G/232V/236H/245R/248D/252K;
61E/68A/103A/104I/159D/232V/236H/245R/248D/252K;

62D/103A/104I/109R/159D/213R/232V/236H/245R/ 248D/252K;
62D/103A/104I/159D/213R/232V/236H/245R/248D/ 252K;
62D/103A/104I/159D/232V/236H/245R/248D/252K;
62D/103A/104I/130G/159D/213R/232V/236H/245R/ 248D/252K;
62D/101G/103A/104I/159D/212G/213R/232V/236H/ 245R/248D/252K;
68A/76D/103A/104I/159D/213R/232V/236H/245R/ 260A;
68A/76D/103A/104I/159D/210I/232V/236H/245R/ 260A;
68A/103A/104I/159D/183D/232V/236H/245R/248D/ 252K;
68A/103A/104I/159D/209W/232V/236H/245R;
68A/76D/103A/104I/159D/211R/232V/236H/245R;
68A/76D/103A/104I/159D/215R/232V/236H/245R;
68A/103A/104I/159D/236H/245R/260A;
68A/76D/103A/104I/159D/232V/236H/245R;
68A/103A/104I/159D/232V/236H/245R/252K;
68A/103A/104I/159D/232V/236H/245R;
68A/103A/104I/159D/232V/236H/245R/257V;
68A/103A/104I/159D/185D/232V/236H/245R/248D/ 252K;
68A/103A/104I/159D/210R/232V/236H/245R/248D/ 252K;
68A/103A/104I/159D/185D/210L/232V/236H/245R/ 248D/252K;
68A/103A/104I/159D/213E/232V/236H/245R/248D/ 252K;
68A/103A/104I/159D/230V/232V/236H/245R;
68A/76D/103A/104I/159D/209W/232V/236H/245R;
68A/103A/104I/232V/236H/245R/248D/257V/275H;
68A/103A/104I/232V/236H/245R/257V/275H;
68A/103A/104I/213E/232V/236H/245R/248D/252K;
68A/103A/104I/159D/232V/236H/245R/248D/252K;
68A/103A/104I/159D/210I/232V/236H/245R;
68A/103A/104I/159D/210L/232V/236H/245R;
68A/103A/104I/159D/213E/232V/236H/245R;
68A/103A/104I/159D/232V/236H/245R/248D/252K/ 270A;
76D/103A/104I/159D/232V/236H/245R;
76D/103A/104I/131V/159D/232V/236V/245R/248D/ 252K;
76D/103A/104I/159D/213R/232V/236H/245R/260A;
97E/103A/104I/159D/232V/236H/245R/248D/252K;
98L/103A/104I/159D/232V/236H/245R/248D/252K;
98L/102A/103A/104I/159D/212G/232V/236H/245R/ 248D/252K;
101G/103A/104I/159D/232V/236H/245R/248D/252K;
102A/103A/104I/159D/232V/236H/245R/248D/252K;
103A/104I/159D/232V/236H/245R/248D/252K;
103A/104I/159D/213R/232V/236H/245R/248D/252K;
103A/104I/130G/159D/232V/236H/245R/248D/252K;
103A/104I/159D/217E/232V/236H/245R/248D/252K;
103A/104I/159D/248D/252K/270V;
103A/104I/159D/232V/236H/245R;
103A/104I/159D/205I/209W/232V/236H/245R;
103A/104I/159D/232V/236H/245R/257V;
103A/104I/159D/205I/209W/232V/236H/245R/257V;
103A/104I/131V/159D/232V/236H/245R/246D/252K;
103A/104I/159D/205I/209W/210I/232V/236H/245R/ 257V; and
103A/104I/159D/232V/245R/248D/252K.

29. The bleaching composition according to claim 1 wherein said bleaching agent is selected from the group consisting of:

(i) an organic peroxyacid selected from the group consisting of organic peroxyacids of the formula:

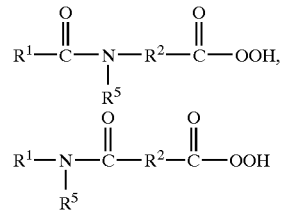

wherein $R^1$ is an alkyl, aryl, or alkaryl group containing from about 1 to about 14 carbon atoms, $R^2$ is an alkylene, arylene or alkarylene group containing from about 1 to about 14 carbon atoms, and $R^5$ is H or an alkyl, aryl, or alkaryl group containing from about 1 to about 10 carbon atoms; E-phthalimido peroxycaproic acids; and mixtures thereof; and (ii) a combination of a bleach activator and a peroxygen compound capable of yielding hydrogen peroxide that can react with the activator to form an organic peroxyacid in situ in a bleaching solution formed from the composition, wherein said bleach activator the general formula:

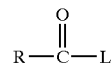

wherein R is an alkyl group containing from about 5 to about 18 carbon atoms wherein the longest linear alkyl chain extending from and including the carbonyl carbon contains from about 6 to about 10 carbon atoms and L is a leaving group, the conjugate acid of which has a pKa in the range of from about 4 to about 13;

said bleach activator having the general formula:

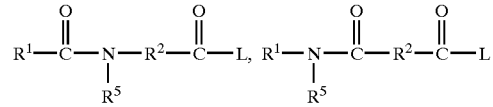

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, at alkaryl group containing from about 1 to about 10 carbon atoms, and L is a leaving group.

30. The bleaching composition according to claim 29 wherein $R^1$ is an alkyl group containing from about 7 to about 10 carbon atoms, $R^2$ contains from about 4 to about 5 carbon atoms, and wherein L is selected from the group consisting of;

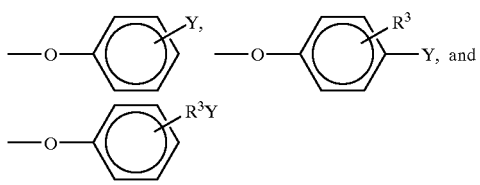

wherein $R^3$ is an alkyl chain containing from about 1 to about 6 carbon atoms, and Y is $-SO_3^+$ or $-CO_2^-M^+$ wherein M is sodium or potassium.

31. The bleaching composition according to claim 1 wherein said bleaching agent comprises a bleach activator selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBs), benzoylvalerolactam (BZVL), octanoyloxybenzenesulphonate, ($C_8$-OBS), perhydrolyzable esters, 4-[N-(nonaoyl)amino hexanoyloxy]-benzene sulfonate sodium salt (NACA-OBS), lauryloxybenzenesulphonate (LOBS or $C_{12}$-OBS), 10-undecenoyloxybenzenesulfonate (UDOBS or $C_{11}$-OBS with unsaturation in the 10 position), and decanoyloxybenzolo acid (DOBA) and mixtures thereof, and further optionally comprises a bleach catalyst.

32. The bleaching composition according to claim 1 wherein said bleaching agent comprises at least about 0.1% by weight of the bleaching agent of a peroxygen bleaching compound capable of yielding hydrogen peroxide in an aqueous liquor and at least 0.1% by weight of the bleaching agent of one or more bleach activator, wherein said bleach activators are members selected from the group consisting of:

a) a bleach activator of the general formula:

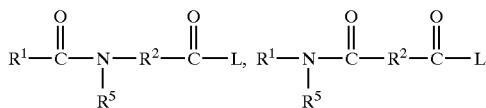

or mixtures thereof, wherein $R^1$ is an alkyl, aryl, or alkaryl group containing from about 1 to about 14 carbon atoms, $R^2$ is an alkylene, arylene or alkarylene group containing from about 1 to about 14 carbon atoms, $R^5$ is H or an alkyl, aryl, or alkaryl group containing from about 1 to about 10 carbon atoms, and L is a leaving group;

b) a benzoxazin-type bleach activator of the formula:

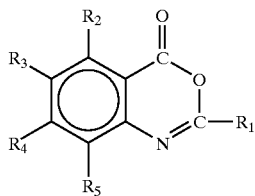

wherein $R^1$ is H, alkyl, alkaryl, aryl, arylalkyl, and wherein R2, R3, R4, and R5 may be the same or different substituents selected from H, halogen, alkyl, alkenyl, aryl, hydroxyl, alkoxyl, amino, alkylamino, $-COOR_6$, wherein $R^6$ is H or an alkyl group and carbonyl functions;

c) a N-acyl caprolactam bleach activator of the formula:

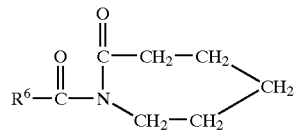

wherein $R^6$ is H or an alkyl, aryl, alkoxyaryl, or alkaryl group containing from 1 to 12 carbons; and d) mixtures of a), b) and c).

33. The bleaching composition according to claim 1 wherein the corresponding carboxylic acid of the organic peroxyacid bleaching agent has a Hydrophilic-Lipophillic Balance value within the range of from about 3 to about 6.5.

34. The bleaching composition according to claim 1 wherein said cleaning adjunct materials are selected from the group consisting of surfactants, solvents, buffers, enzymes, soil release agents, clay removal agents, dispersing agents, brighteners, suds suppressors, fabric softeners, suds boosters, enzyme stabilizers, builders, other bleaching agents, dyes, perfumes, chelants and mixtures thereof.

35. The bleaching composition according to claim 34 wherein said cleaning adjunct materials comprise at least one detersive surfactant.

36. The bleaching composition according to claim 34 wherein the cleaning adjunct materials comprise at least about 0.1% surfactant by weight of the composition, said surfactant comprising materials selected from the group consisting of alkyl benzene sulfonates, primary alkyl sulfates, secondary alkyl sulfates, alkyl alkoxy sulfates, alkyl alkoxy carboxylates, alkyl polyglycosides and their corresponding sulfated polyglycosides, alpha-sulfonated fatty acid esters, alkyl and alkyl phenol alkoxylates, betaines and sulfobetaines, amine oxides, N-methyl glucamides, nonionic primary alcohol ethoxylates, nonionic primary alcohol mixed ethoxy/propoxy, and mixtures thereof.

37. The bleaching composition according to claim 36 further comprising at least about 5% builder selected from the group consisting of zeolites, polycarboxylates, layered silicates, phosphates, and mixtures thereof.

38. The bleaching composition according to claim 34 wherein said cleaning adjunct materials comprise at least one detersive enzyme selected from the group consisting of cellulases, lipases, amylases, phospholipases, other proteases, peroxidases and mixtures thereof.

39. The bleaching composition according to claim 1 wherein said bleaching composition is a fabric bleaching composition, preferably in the form of a liquid, granule, tablet, powder or bar, comprising at least about 5% surfactant and at least about 5% builder by weight of the composition.

40. The bleaching composition according to claim 1 wherein said bleaching composition is a fabric bleaching composition comprising:

(a) from about 0.0001% to about 10% by weight of said protease variant;
(b) from about 0.5% to about 20% by weight of said bleaching agent;
(c) at least about 5% by weight of a surfactant selected from the group consisting of alkyl benzene sulfonates, primary alkyl sulfates, secondary alkyl sulfates, alkyl alkoxy sulfates, alkyl alkoxy carboxylates, alkyl polyglycosides and their corresponding sulfated polyglycosides, alpha-sulfonated fatty add esters, alkyl and alkyl phenol alkoxylates, betaines and sulfobetaines, amine oxides, N-methyl glucamides, nonionic primary alcohol ethoxylates, nonionic primary alcohol mixed ethoxy/propoxy, and mixtures thereof; and (d) at least about 6% by weight of a builder selected from the group consisting of zeolites, polycarboxylates, layered silicates, phosphates, and mixtures thereof.

41. The bleaching composition according to claim 40 in the form of a concentrated granular fabric bleaching composition comprising at least about 15% surfactant.

42. A method for cleaning fabric, said method comprising contacting a fabric in need of cleaning with a bleaching composition according to claims 39 or 40.

43. The bleaching composition according to claim 1 wherein said bleaching composition is a dishwashing bleaching composition, in the form of a liquid, granule, powder or tablet, comprising:

(a) from about 0.0001% to about 10% by weight of the dishwashing bleaching composition of said protease variant;

(b) from about 0.5% to about 20% by weight of the dishwashing bleaching composition of said bleaching agent (c) from about 0.1% to about 10% by weight of the dishwashing bleaching composition of a surfactant.

44. A method for cleaning dishes, said method comprising contacting a dish in need of cleaning with a bleaching composition according to claim 43.

45. A personal cleansing composition comprising:

(a) from about 0.001% to about 5% by weight of the personal cleansing composition of a protease variant wherein said protease variant includes a substitution of an amino acid residue with another naturally occurring amino acid residue at one or more amino acid residue positions corresponding to positions 62, 212, 230, 232, 252 and 257 of *Bacillus amyloliquefaciens* subtilisin;

(b) from about 0.5% to about 20% by weight of the personal cleansing composition of a bleaching agent which either is an organic peroxyacid or is a combination of a bleach activator and a peroxygen compound capable of yielding hydrogen peroxide that can react with the activator to form an organic peroxyacid in situ in a bleaching solution formed from the composition; and (c) from about 0.1% to about 95% by weight of the personal cleansing composition of a surfactant system comprising one or more surfactants selected from the group consisting of anionic carboxylates, amine oxides, alkyl glucosides, glucose amides, alkyl sulfates, alkyl ether sulfates, acyl isothiaonates, alkyl sulfosuccinates, alkyl phosphate esters, ethoxylated phosphate easters, alkyl glyceryl ether sulfonates and mixtures thereof; and (d) optionally, from about 0.05% to about 50% by weight of the personal cleansing composition of an enzyme stabilizer.

46. The bleaching composition according to claim 45 wherein said surfactant is soap at a level of at least about 2% by weight of the bleaching composition.

47. The bleaching composition according to claim 46 wherein the ratio of soap to protease variant is from about 2,000:1 to about 8:1.

48. A method for personal cleansing, said method comprising contacting a part of the human or lower animal body in need of cleaning with a bleaching composition according to claim 45.

49. A method for pretreating a fabric in need of cleaning, said method comprising contacting said fabric prior to washing said fabric with an aqueous solution containing a surfactant with a bleaching composition according to claim 39 or 40.

* * * * *

UNITED STATES PATENT AND TRADEMARK OFFICE
CERTIFICATE OF CORRECTION

PATENT NO. : 6,831,053 B1
APPLICATION NO. : 09/529904
DATED : December 14, 2004
INVENTOR(S) : Chanchal Kumar Ghosh et al.

It is certified that error appears in the above-identified patent and that said Letters Patent is hereby corrected as shown below:

Column 42, line 49, delete "Table II" and insert therefor --Table VII--.

Column 85, line 53, delete "Manganese(I)" and insert therefor --Manganese(II)--.

Column 85, lie 59, delete "Manganese(III)" and insert therefor --Manganese(II)--.

Column 108, lines 14-16, delete "Hydrophobic precipitate silica" and insert therefor --Hydrophobic precipitated silica--.

Column 108, line 37, delete "5,476,507" and insert therefor --5,470,507--.

Column 128, line 35, delete "230" and insert therefor --232--.

Column 129, line 2, delete "246" and insert therefor --245--.

Column 129, line 21, delete "12/76/103/104/222/245;" and insert therefor --12/76/103/104/130/222/245;--.

Column 129, line 60, delete "76/103/159/232/236/245;" and insert therefor --76/103/104/159/232/236/245;--.

Column 130, line 58, delete "68/103A/104I/159D/232V/236V/245R/252K;" and insert therefor --68A/103A/104I/159D/232V/236H/245R/252K;--.

Column 131, line 21, delete "76D/103A/104I/159D/232V/236V/245H/248R/252K;" and insert therefor --76D/103A/104I/131V/159D/232V/236H/245R/248D/252K;--.

Column 132, line 37, delete "to" and insert therefor --is--.

Column 133, line 35, delete "wherein R1 H," and insert therefor --wherein R1 is H--.

Column 133, line 50, delete "or a group" and insert therefor --or alkaryl group--.

Column 133, line 52, delete "mixture of a), b) and c)." and insert therefor --mixtures of a), b) and c)--.

Column 133, line 55, delete "Hydrophillic" and insert therefor --Hydrophilic--.

Column 134, lines 10-11, delete "gluamides, nonoinic" and insert therefor --glucamides, nonionic--.

UNITED STATES PATENT AND TRADEMARK OFFICE
CERTIFICATE OF CORRECTION

| | |
|---|---|
| PATENT NO. | : 6,831,053 B1 |
| APPLICATION NO. | : 09/529904 |
| DATED | : December 14, 2004 |
| INVENTOR(S) | : Chanchal Kumar Ghosh et al. |

It is certified that error appears in the above-identified patent and that said Letters Patent is hereby corrected as shown below:

Column 134, line 14, delete "6% builder" and insert therefor --5% builder--.

Column 135, line 6, delete "proteases" and insert therefor --protease--.

Column 135, line 15, delete "66" and insert therefor --68--.

Column 135, line 18, delete "148" and insert therefor --146--.

Column 135, line 18, delete "168" and insert therefor --166--.

Column 135, line 20, delete "208" and insert therefor --206--.

Column 135, line 23, delete "268" and insert therefor --258--.

Column 135, line 32, delete "218" and insert therefor --216--.

Column 135, line 32, delete "280" and insert therefor --260--.

Column 135, line 51, delete "cleaning" and insert therefor --cleansing--.

Column 136, line 7, delete "62/103/104/159/232/236/245/248/252;" and insert therefor --62/103/104/159/213/232/236/245/248/252;--.

Column 137, line 19, delete "68A/103A/104I/159D/236H/245R/260A" and insert therefor --68A/103A/104I/159D/213R/232V/236H/245R/260A --.

Column 138, line 35, delete "wherein said bleach activator the general" and insert therefor --wherein said bleach activator has the general--.

Column 138, line 60, delete "at alkaryl group" and insert therefor --or alkaryl group--.

Column 139, line 25, delete "decanoyloxybenzolo acid" and insert therefor --decanoyloxybenzoic acid--.

Column 139, line 33, delete "bleach activator" and insert therefor --bleach activators--.

Column 140, line 15, delete "Hydrophilic-Lipophillic" and insert therefor --Hydrophilic-Lipophilic--.

Column 140, line 20, delete "clay removal agents" and insert therefor --clay soil removal agents--.

UNITED STATES PATENT AND TRADEMARK OFFICE
CERTIFICATE OF CORRECTION

PATENT NO. : 6,831,053 B1
APPLICATION NO. : 09/529904
DATED : December 14, 2004
INVENTOR(S) : Chanchal Kumar Ghosh et al.

It is certified that error appears in the above-identified patent and that said Letters Patent is hereby corrected as shown below:

Column 141, line 5, delete "6%" and insert therefor --5%--.

Column 142, line 14, delete "acyl isothianonates," and insert therefor --acyl isethionates,--.

Signed and Sealed this

Thirty-first Day of July, 2007

JON W. DUDAS
*Director of the United States Patent and Trademark Office*

SEQUENCE LISTING

<160> NUMBER OF SEQ ID NOS: 7

<210> SEQ ID NO 1
<211> LENGTH: 1497
<212> TYPE: DNA
<213> ORGANISM: Bacillus amyloliquefaciens
<220> FEATURE:
<221> NAME/KEY: CDS
<222> LOCATION: (96)..(1241)

<400> SEQUENCE: 1
ggtctactaa aatattattc catactatac aattaataca cagaataatc tgtctattgg      60
ttattctgca aatgaaaaaa aggagaggat aaaga gtg aga ggc aaa aaa gta      113
                                       Val Arg Gly Lys Lys Val
                                        1               5 tgg atc agt ttg ctg ttt gct tta gcg tta atc ttt acg atg gcg ttc    161
Trp Ile Ser Leu Leu Phe Ala Leu Ala Leu Ile Phe Thr Met Ala Phe

```
                10              15              20
ggc agc aca tcc tct gcc cag gcg gca ggg aaa tca aac ggg gaa aag        209
Gly Ser Thr Ser Ser Ala Gln Ala Ala Gly Lys Ser Asn Gly Glu Lys
        25              30              35 aaa tat att gtc ggg ttt aaa cag aca atg agc acg atg agc gcc gct        257
Lys Tyr Ile Val Gly Phe Lys Gln Thr Met Ser Thr Met Ser Ala Ala
    40              45              50 aag aag aaa gat gtc att tct gaa aaa ggc ggg aaa gtg caa aag caa        305
Lys Lys Lys Asp Val Ile Ser Glu Lys Gly Gly Lys Val Gln Lys Gln
 55              60              65              70 ttc aaa tat gta gac gca gct tca gtc aca tta aac gaa aaa gct gta        353
Phe Lys Tyr Val Asp Ala Ala Ser Val Thr Leu Asn Glu Lys Ala Val
            75              80              85 aaa gaa ttg aaa aaa gac ccg agc gtc gct tac gtt gaa gaa gat cac        401
Lys Glu Leu Lys Lys Asp Pro Ser Val Ala Tyr Val Glu Glu Asp His
        90              95              100 gta gca cat gcg tac gcg cag tcc gtg cct tac ggc gta tca caa att        449
Val Ala His Ala Tyr Ala Gln Ser Val Pro Tyr Gly Val Ser Gln Ile
        105             110             115 aaa gcc cct gct ctg cac tct caa ggc tac act gga tca aat gtt aaa        497
Lys Ala Pro Ala Leu His Ser Gln Gly Tyr Thr Gly Ser Asn Val Lys
120             125             130 gta gcg gtt atc gac agc ggt atc gat tct tct cat cct gat tta aag        545
Val Ala Val Ile Asp Ser Gly Ile Asp Ser Ser His Pro Asp Leu Lys
135             140             145             150 gta gca agc gga gcc agc atg gtt cct tct gaa aca aat cct ttc caa        593
Val Ala Ser Gly Ala Ser Met Val Pro Ser Glu Thr Asn Pro Phe Gln
            155             160             165 gac aac aac tct cac gga act cac gtt gcc ggc aca gtt gcg gct ctt        641
Asp Asn Asn Ser His Gly Thr His Val Ala Gly Thr Val Ala Ala Leu
        170             175             180 aat aac tca atc ggt gta tta ggc gtt gcg cca agc gca tca ctt tac        689
Asn Asn Ser Ile Gly Val Leu Gly Val Ala Pro Ser Ala Ser Leu Tyr
        185             190             195 gct gta aaa gtt ctc ggt gct gac ggt tcc ggc caa tac agc tgg atc        737
Ala Val Lys Val Leu Gly Ala Asp Gly Ser Gly Gln Tyr Ser Trp Ile
200             205             210 att aac gga atc gag tgg gcg atc gca aac aat atg gac gtt att aac        785
Ile Asn Gly Ile Glu Trp Ala Ile Ala Asn Asn Met Asp Val Ile Asn
215             220             225             230 atg agc ctc ggc gga cct tct ggt tct gct gct tta aaa gcg gca gtt        833
Met Ser Leu Gly Gly Pro Ser Gly Ser Ala Ala Leu Lys Ala Ala Val
            235             240             245 gat aaa gcc gtt gca tcc ggc gtc gta gtc gtt gcg gca gcc ggt aac        881
Asp Lys Ala Val Ala Ser Gly Val Val Val Ala Ala Ala Gly Asn
        250             255             260 gaa ggc act tcc ggc agc tca agc aca gtg ggc tac cct ggt aaa tac        929
Glu Gly Thr Ser Gly Ser Ser Ser Thr Val Gly Tyr Pro Gly Lys Tyr
        265             270             275 cct tct gtc att gca gta ggc gct gtt gac agc agc aac caa aga gca        977
Pro Ser Val Ile Ala Val Gly Ala Val Asp Ser Ser Asn Gln Arg Ala
    280             285             290 tct ttc tca agc gta gga cct gag ctt gat gtc atg gca cct ggc gta       1025
Ser Phe Ser Ser Val Gly Pro Glu Leu Asp Val Met Ala Pro Gly Val
295             300             305             310 tct atc caa agc acg ctt cct gga aac aaa tac ggg gcg tac aac ggt       1073
Ser Ile Gln Ser Thr Leu Pro Gly Asn Lys Tyr Gly Ala Tyr Asn Gly
            315             320             325 acg tca atg gca tct ccg cac gtt gcc gga gcg gct gct ttg att ctt       1121
```

-continued

```
Thr Ser Met Ala Ser Pro His Val Ala Gly Ala Ala Ala Leu Ile Leu
            330                 335                 340
tct aag cac ccg aac tgg aca aac act caa gtc cgc agc agt tta gaa      1169
Ser Lys His Pro Asn Trp Thr Asn Thr Gln Val Arg Ser Ser Leu Glu
            345                 350                 355
aac acc act aca aaa ctt ggt gat tct ttg tac tat gga aaa ggg ctg      1217
Asn Thr Thr Thr Lys Leu Gly Asp Ser Leu Tyr Tyr Gly Lys Gly Leu
        360                 365                 370
atc aac gta caa gcg gca gct cag taaaacataa aaaaccggcc ttggccccgc     1271
Ile Asn Val Gln Ala Ala Ala Gln
375                 380 cggttttta ttattttct tcctccgcat gttcaatccg ctccataatc gacggatggc      1331
tccctctgaa aattttaacg agaaacggcg ggttgacccg gctcagtccc gtaacggcca    1391
actcctgaaa cgtctcaatc gccgcttccc ggtttccggt cagctcaatg ccataacggt    1451
cggcggcgtt ttcctgatac cgggagacgg cattcgtaat cggatc                   1497
```

<210> SEQ ID NO 2
<211> LENGTH: 382
<212> TYPE: PRT
<213> ORGANISM: Bacillus amyloliquefaciens

<400> SEQUENCE: 2

```
Val Arg Gly Lys Lys Val Trp Ile Ser Leu Leu Phe Ala Leu Ala Leu
  1               5                  10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Val Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255
```

-continued

```
Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Leu
        355                 360                 365

Tyr Tyr Gly Lys Gly Leu Ile Asn Val Gln Ala Ala Gln
370                 375                 380
```

<210> SEQ ID NO 3
<211> LENGTH: 1497
<212> TYPE: PRT
<213> ORGANISM: Bacillus amyloliquefaciens

<400> SEQUENCE: 3

```
Gly Gly Thr Cys Thr Ala Cys Thr Ala Ala Ala Thr Ala Thr Thr
  1               5                  10                  15

Ala Thr Thr Cys Cys Ala Thr Ala Cys Thr Ala Thr Cys Ala Ala
            20                  25                  30

Thr Thr Ala Ala Thr Ala Cys Ala Cys Ala Gly Ala Ala Thr Ala Ala
            35                  40                  45

Thr Cys Thr Gly Thr Cys Thr Ala Thr Thr Gly Thr Thr Ala Thr
        50                  55                  60

Thr Cys Thr Gly Cys Ala Ala Ala Thr Gly Ala Ala Ala Ala Ala
 65                 70                  75                  80

Ala Gly Gly Ala Gly Ala Gly Gly Ala Thr Ala Ala Gly Ala Gly
            85                  90                  95

Thr Gly Ala Gly Ala Gly Gly Cys Ala Ala Ala Ala Ala Gly Thr
        100                 105                 110

Ala Thr Gly Gly Ala Thr Cys Ala Gly Thr Thr Thr Gly Cys Thr Gly
        115                 120                 125

Thr Thr Thr Gly Cys Thr Thr Ala Gly Cys Gly Thr Thr Ala Ala
        130                 135                 140

Thr Cys Thr Thr Thr Ala Cys Gly Ala Thr Gly Gly Cys Gly Thr Thr
145                 150                 155                 160

Cys Gly Gly Cys Ala Gly Cys Ala Cys Thr Cys Thr Cys Thr
            165                 170                 175

Gly Cys Cys Cys Ala Gly Cys Gly Gly Cys Ala Gly Gly Ala
        180                 185                 190

Ala Ala Thr Cys Ala Ala Cys Gly Gly Gly Ala Ala Ala Ala
        195                 200                 205

Gly Ala Ala Ala Thr Ala Thr Ala Thr Thr Gly Thr Cys Gly Gly
210                 215                 220

Thr Thr Thr Ala Ala Ala Cys Ala Gly Ala Cys Ala Ala Thr Gly Ala
225                 230                 235                 240

Gly Cys Ala Cys Gly Ala Thr Gly Ala Gly Cys Gly Cys Gly Cys
                245                 250                 255
```

```
Thr Ala Ala Gly Ala Ala Gly Ala Ala Ala Gly Ala Thr Gly Thr Cys
            260                 265                 270

Ala Thr Thr Thr Cys Thr Gly Ala Ala Ala Ala Gly Gly Cys Gly
            275                 280                 285

Gly Gly Ala Ala Ala Gly Thr Gly Cys Ala Ala Ala Gly Cys Ala
            290                 295                 300

Ala Thr Thr Cys Ala Ala Ala Thr Ala Thr Gly Thr Ala Gly Ala Cys
305                 310                 315                 320

Gly Cys Ala Gly Cys Thr Thr Cys Ala Gly Thr Cys Ala Cys Ala Thr
                325                 330                 335

Thr Ala Ala Cys Gly Ala Ala Ala Gly Cys Thr Gly Thr
            340                 345                 350

Ala Ala Ala Ala Gly Ala Ala Thr Gly Ala Ala Ala Ala Ala
            355                 360                 365

Gly Ala Cys Cys Cys Gly Ala Gly Cys Gly Thr Cys Gly Cys Thr Thr
            370                 375                 380

Ala Cys Gly Thr Thr Gly Ala Ala Gly Ala Ala Gly Ala Thr Cys Ala
385                 390                 395                 400

Cys Gly Thr Ala Gly Cys Ala Cys Ala Thr Gly Cys Gly Thr Ala Cys
                405                 410                 415

Gly Cys Gly Cys Ala Gly Thr Cys Cys Gly Thr Gly Cys Cys Thr Thr
            420                 425                 430

Ala Cys Gly Gly Cys Gly Thr Ala Thr Cys Ala Cys Ala Ala Ala Thr
            435                 440                 445

Thr Ala Ala Gly Cys Cys Cys Thr Gly Cys Thr Cys Thr Gly
450                 455                 460

Cys Ala Cys Thr Cys Thr Cys Ala Ala Gly Gly Cys Thr Ala Cys Ala
465                 470                 475                 480

Cys Thr Gly Gly Ala Thr Cys Ala Ala Ala Thr Gly Thr Thr Ala Ala
            485                 490                 495

Ala Gly Thr Ala Gly Cys Gly Gly Thr Thr Ala Thr Cys Gly Ala Cys
            500                 505                 510

Ala Gly Cys Gly Gly Thr Ala Thr Cys Gly Ala Thr Thr Cys Thr Thr
            515                 520                 525

Cys Thr Cys Ala Thr Cys Cys Thr Gly Ala Thr Thr Ala Ala Ala
            530                 535                 540

Gly Gly Thr Ala Gly Cys Ala Ala Gly Cys Gly Gly Ala Gly Cys Cys
545                 550                 555                 560

Ala Gly Cys Ala Thr Gly Gly Thr Thr Cys Cys Thr Cys Thr Gly
            565                 570                 575

Ala Ala Ala Cys Ala Ala Ala Thr Cys Cys Thr Thr Cys Cys Ala
            580                 585                 590

Ala Gly Ala Cys Ala Ala Cys Ala Ala Cys Thr Cys Thr Cys Ala Cys
            595                 600                 605

Gly Gly Ala Ala Cys Thr Cys Ala Cys Gly Thr Thr Gly Cys Gly
            610                 615                 620

Gly Cys Ala Cys Ala Gly Thr Thr Gly Cys Gly Gly Cys Thr Cys Thr
625                 630                 635                 640

Thr Ala Ala Thr Ala Cys Thr Cys Ala Ala Thr Cys Gly Gly Thr
            645                 650                 655

Gly Thr Ala Thr Thr Ala Gly Gly Cys Gly Thr Thr Gly Cys Gly Cys
            660                 665                 670
```

-continued

```
Cys Ala Ala Gly Cys Gly Cys Ala Thr Cys Ala Cys Thr Thr Ala
        675                 680                 685
Cys Gly Cys Thr Gly Thr Ala Ala Ala Gly Thr Thr Cys Thr Cys
        690                 695                 700
Gly Gly Thr Gly Cys Thr Gly Ala Cys Gly Thr Thr Cys Cys Gly
705                 710                 715                 720
Gly Cys Cys Ala Ala Thr Ala Cys Ala Gly Cys Thr Gly Gly Ala Thr
            725                 730                 735
Cys Ala Thr Thr Ala Ala Cys Gly Gly Ala Ala Thr Cys Gly Ala Gly
        740                 745                 750
Thr Gly Gly Gly Cys Gly Ala Thr Cys Gly Cys Ala Ala Cys Ala
        755                 760                 765
Ala Thr Ala Thr Gly Gly Ala Cys Gly Thr Thr Ala Thr Thr Ala Ala
        770                 775                 780
Cys Ala Thr Gly Ala Gly Cys Cys Thr Cys Gly Gly Cys Gly Gly Ala
785                 790                 795                 800
Cys Cys Thr Thr Cys Thr Gly Gly Thr Thr Cys Thr Gly Cys Thr Gly
        805                 810                 815
Cys Thr Thr Ala Ala Ala Gly Cys Gly Gly Cys Ala Gly Thr
        820                 825                 830
Thr Gly Ala Thr Ala Ala Gly Cys Cys Gly Thr Thr Gly Cys Ala
        835                 840                 845
Thr Cys Cys Gly Gly Cys Gly Thr Cys Gly Thr Ala Gly Thr Cys Gly
        850                 855                 860
Thr Thr Gly Cys Gly Gly Cys Ala Cys Cys Gly Gly Thr Ala Ala
865                 870                 875                 880
Cys Gly Ala Ala Gly Cys Ala Cys Thr Thr Cys Cys Gly Gly Cys
            885                 890                 895
Ala Gly Cys Thr Cys Ala Ala Gly Cys Ala Cys Ala Gly Thr Gly Gly
        900                 905                 910
Gly Cys Thr Ala Cys Cys Cys Thr Gly Gly Thr Ala Ala Ala Thr Ala
        915                 920                 925
Cys Cys Cys Thr Thr Cys Thr Gly Thr Cys Ala Thr Thr Gly Cys Ala
        930                 935                 940
Gly Thr Ala Gly Gly Cys Gly Cys Thr Gly Thr Thr Gly Ala Cys Ala
945                 950                 955                 960
Gly Cys Ala Gly Cys Ala Ala Cys Cys Ala Ala Gly Ala Gly Cys
            965                 970                 975
Ala Thr Cys Thr Thr Thr Cys Thr Ala Ala Gly Cys Gly Thr Ala
        980                 985                 990
Gly Gly Ala Cys Cys Thr Gly Ala Gly Cys Thr Thr Gly Ala Thr Gly
        995                 1000                1005
Thr Cys Ala Thr Gly Gly Cys Ala Cys Cys Thr Gly Gly Cys Gly Thr
    1010                1015                1020
Ala Thr Cys Thr Ala Thr Cys Cys Ala Ala Ala Gly Cys Ala Cys Gly
1025                1030                1035                1040
Cys Thr Thr Cys Cys Thr Gly Gly Ala Ala Ala Cys Ala Ala Ala Thr
            1045                1050                1055
Ala Cys Gly Gly Gly Gly Cys Gly Thr Ala Cys Ala Ala Cys Gly Gly
        1060                1065                1070
Thr Ala Cys Gly Thr Cys Ala Ala Thr Gly Gly Cys Ala Thr Cys Thr
    1075                1080                1085
Cys Cys Gly Cys Ala Cys Gly Thr Thr Gly Cys Cys Gly Gly Ala Gly
```

-continued

```
                1090                1095                1100
Cys Gly Gly Cys Thr Gly Cys Thr Thr Gly Ala Thr Thr Cys Thr
1105                1110                1115                1120
Thr Thr Cys Thr Ala Ala Gly Cys Ala Cys Cys Cys Gly Ala Ala Cys
                1125                1130                1135
Thr Gly Gly Ala Cys Ala Ala Cys Ala Cys Thr Cys Ala Ala Gly
        1140                1145                1150
Thr Cys Cys Gly Cys Ala Gly Cys Ala Gly Thr Thr Thr Ala Gly Ala
        1155                1160                1165
Ala Ala Ala Cys Ala Cys Cys Ala Cys Thr Ala Cys Ala Ala Ala Ala
    1170                1175                1180
Cys Thr Thr Gly Gly Thr Gly Ala Thr Thr Cys Thr Thr Thr Gly Thr
1185                1190                1195                1200
Ala Cys Thr Ala Thr Gly Gly Ala Ala Ala Gly Gly Gly Cys Thr
            1205                1210                1215
Gly Ala Thr Cys Ala Ala Cys Gly Thr Ala Cys Ala Ala Gly Cys Gly
        1220                1225                1230
Gly Cys Ala Gly Cys Thr Cys Ala Gly Thr Ala Ala Ala Cys Ala
    1235                1240                1245
Thr Ala Ala Ala Ala Ala Cys Cys Gly Gly Cys Cys Thr Thr Gly
1250                1255                1260
Gly Cys Cys Cys Cys Gly Cys Cys Gly Gly Thr Thr Thr Thr Thr
1265                1270                1275                1280
Ala Thr Thr Ala Thr Thr Thr Thr Thr Cys Thr Thr Cys Cys Thr Cys
            1285                1290                1295
Cys Gly Cys Ala Thr Gly Thr Thr Cys Ala Ala Thr Cys Cys Gly Cys
        1300                1305                1310
Thr Cys Cys Ala Thr Ala Ala Thr Cys Gly Ala Cys Gly Gly Ala Thr
            1315                1320                1325
Gly Gly Cys Thr Cys Cys Cys Thr Cys Thr Gly Ala Ala Ala Ala Thr
        1330                1335                1340
Thr Thr Thr Ala Ala Cys Gly Ala Gly Ala Ala Ala Cys Gly Gly Cys
1345                1350                1355                1360
Gly Gly Gly Thr Thr Gly Ala Cys Cys Cys Gly Gly Cys Thr Cys Ala
            1365                1370                1375
Gly Thr Cys Cys Cys Gly Thr Ala Ala Cys Gly Gly Cys Cys Ala Ala
        1380                1385                1390
Cys Thr Cys Cys Thr Gly Ala Ala Ala Cys Gly Thr Cys Thr Cys Ala
    1395                1400                1405
Ala Thr Cys Gly Cys Cys Gly Cys Thr Thr Cys Cys Cys Gly Gly Thr
    1410                1415                1420
Thr Thr Cys Cys Gly Gly Thr Cys Ala Gly Cys Thr Cys Ala Ala Thr
1425                1430                1435                1440
Gly Cys Cys Ala Thr Ala Ala Cys Gly Gly Thr Cys Gly Gly Cys Gly
            1445                1450                1455
Gly Cys Gly Thr Thr Thr Thr Cys Cys Thr Gly Ala Thr Ala Cys Cys
        1460                1465                1470
Gly Gly Gly Ala Gly Ala Cys Gly Gly Cys Ala Thr Thr Cys Gly Thr
        1475                1480                1485
Ala Ala Thr Cys Gly Gly Ala Thr Cys
    1490                1495

<210> SEQ ID NO 4
```

```
<211> LENGTH: 275
<212> TYPE: PRT
<213> ORGANISM: Bacillus amyloliquefaciens

<400> SEQUENCE: 4

Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
 65                 70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly Ser
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 5
<211> LENGTH: 275
<212> TYPE: PRT
<213> ORGANISM: Bacillus subtilis

<400> SEQUENCE: 5

Ala Gln Ser Val Pro Tyr Gly Ile Ser Gln Ile Lys Ala Pro Ala Leu
 1               5                  10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
    50                  55                  60
```

-continued

```
Gly Thr His Val Ala Gly Thr Ile Ala Ala Leu Asn Asn Ser Ile Gly
 65                  70                  75                  80

Val Leu Gly Val Ser Pro Ser Ala Ser Leu Tyr Ala Val Lys Val Leu
                 85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
    275

<210> SEQ ID NO 6
<211> LENGTH: 274
<212> TYPE: PRT
<213> ORGANISM: Bacillus licheniformis

<400> SEQUENCE: 6

Ala Gln Thr Val Pro Tyr Gly Ile Pro Leu Ile Lys Ala Asp Lys Val
  1               5                  10                  15

Gln Ala Gln Gly Phe Lys Gly Ala Asn Val Lys Val Ala Val Leu Asp
                 20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
        50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Asn Ser Gly Ser
```

```
                145                 150                 155                 160
Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 7
<211> LENGTH: 269
<212> TYPE: PRT
<213> ORGANISM: Bacillus lentus

<400> SEQUENCE: 7

Ala Gln Ser Val Pro Trp Gly Ile Ser Arg Val Gln Ala Pro Ala Ala
  1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
         50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240
```

```
-continued

Arg Asn His Leu Lys Asn Thr Ala Thr Ser Leu Gly Ser Thr Asn Leu
            245             250                 255

Tyr Gly Ser Gly Leu Val Asn Ala Glu Ala Ala Thr Arg
            260             265
```